(12) United States Patent
Gearing

(10) Patent No.: US 9,328,164 B2
(45) Date of Patent: May 3, 2016

(54) ANTI-NERVE GROWTH FACTOR ANTIBODIES AND METHODS OF PREPARING AND USING THE SAME

(75) Inventor: David Gearing, Southbank (AU)

(73) Assignee: NVIP PTY LTD, Melbourne (AU)

( * ) Notice: Subject to any disclaimer, the term of this patent is extended or adjusted under 35 U.S.C. 154(b) by 19 days.

(21) Appl. No.: 14/115,787

(22) PCT Filed: May 8, 2012

(86) PCT No.: PCT/GB2012/051003
§ 371 (c)(1),
(2), (4) Date: Feb. 11, 2014

(87) PCT Pub. No.: WO2012/153122
PCT Pub. Date: Nov. 15, 2012

(65) Prior Publication Data
US 2014/0147439 A1 May 29, 2014

Related U.S. Application Data

(60) Provisional application No. 61/483,488, filed on May 6, 2011, provisional application No. 61/531,439, filed on Sep. 6, 2011.

(51) Int. Cl.
*C07K 16/22* (2006.01)
*C07K 16/46* (2006.01)

(52) U.S. Cl.
CPC .............. *C07K 16/22* (2013.01); *C07K 16/467* (2013.01); *C07K 2317/24* (2013.01)

(58) Field of Classification Search
CPC ... C07K 16/22; C07K 16/467; C07K 2317/24
USPC .............. 424/133.1, 158.1; 530/387.1, 387.3, 530/389.2
See application file for complete search history.

(56) References Cited

FOREIGN PATENT DOCUMENTS

| EP | 2 138 512 B1 | 12/2009 |
|---|---|---|
| WO | WO-93/16192 | 8/1993 |
| WO | WO-01/77332 A2 | 10/2001 |
| WO | WO-03/002607 A1 | 1/2003 |
| WO | WO-03/060080 A2 | 7/2003 |
| WO | WO-2004/020579 A2 | 3/2004 |
| WO | WO 2004/073653 A2 | 9/2004 |
| WO | WO-2005/061540 A2 | 7/2005 |
| WO | WO 2006/050491 A2 | 5/2006 |
| WO | WO-2006/131951 A2 | 12/2006 |
| WO | WO-2010/027488 A2 | 3/2010 |
| WO | WO-2010/110838 A2 | 9/2010 |
| WO | WO-2010/117448 A2 | 10/2010 |
| WO | WO-2012/024650 A2 | 2/2012 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Gorman and Clark, "Humanisation of monoclonal antibodies for therapy," Seminars in Immunology, vol. 2, pp. 457-466, Nov. 1990.
Gorman et al., "Reshaping a therapeutic CD4 antibody," Proc. Natl. Acad. Sci USA, vol. 88, pp. 4181-4185, May 1991.
Riechmann et al., "Reshaping human antibodies for therapy," Nature, vol. 332, pp. 323-327, Mar. 1988.
Abe et al., "Protective Role of Nerve Growth Factor Against Postischemic Dysfunction of Sympathetic Coronary Innervation," Circulation, vol. 95, No. 1, Jan. 7, 1997.
Cattaneo et al., "Humanized alpha D11 antibody heavy chain variable region SEQ ID No. 17," Database Accension No. AEB12537, Sep. 8, 2005.
U.S. Appl. No. 14/115,772, filed Feb. 5, 2014, David Gearing.
U.S. Appl. No. 14/115,779, filed Feb. 6, 2014, David Gearing.
U.S. Appl. No. 14/115,784, filed Nov. 5, 2013, David Gearing.
U.S. Appl. No. 14/241,616, filed Feb. 27, 2014, David Gearing.
U.S. Appl. No. 14/342,943, filed Mar. 5, 2014, David Gearing.
Cattaneo, "Method for the humanization of antibodies and humanized antibodies thereby obtained Patent No. WO2005/061540-A2," Database Accesion No. CS126835, Jul. 20, 2005.
Covaceuszach et al., "Dissecting NGF Interactions with TrkA and p75 Receptors by Structural and Functional Studies of an Anti-NGF Neutralizing Antibody," Journal of Molecular Biology, Academic Press, vol. 381, No. 4, Sep. 12, 2008.
International Search Report mailed Aug. 1, 2012 issued in connection with International Application No. PCT/GB2012/051008.
International Search Report mailed Aug. 20, 2012 issued in connection with International Application No. PCT/GB2012/051004.
International Search Report mailed Aug. 30, 2012 issued in connection with International Application No. PCT/GB2012/051003.
International Search Report mailed Sep. 4, 2012 issued in connection with International Application No. PCT/GB2012/051002.

(Continued)

*Primary Examiner* — Lynn Bristol
(74) *Attorney, Agent, or Firm* — Foley & Lardner LLP

(57) ABSTRACT

A method of preparing an antibody suitable for use in a feline is provided. Also provided are chimeric and felinized antibodies which specifically bind to feline neuronal growth factor (NGF) and neutralize the ability of feline NGF to bind to the p75 or TrkA feline NGF receptor. The invention extends to nucleic acids encoding same and to methods of treating pain and arthritis in a feline using said antibodies and/or nucleic acids.

19 Claims, 17 Drawing Sheets

(56) References Cited

OTHER PUBLICATIONS

International Search Report mailed Dec. 3, 2012 issued in connection with International Application No. PCT/GB2012/052115.
International Search Report mailed Dec. 4, 2012 issued in connection with International Application No. PCT/GB2012/052174.
Karampetsou et al., "TNF-α antagonists beyond approved indications: stories of success and prospects for the future", QJM, vol. 103, No. 12, pp. 917-928, Aug. 27, 2010.
Pelat et al., "Non-human primate immune libraries combined with germline humanization: an (almost) new, and powerful approach for the isolation of therapeutic antibodies," mAbs, vol. 1, No. 4, pp. 377-381, Jul. 1, 2009.
Pelat et al., "Obtention and engineering of non-human primate (NHP) antibodies for therapeutics," Mini Reviews in Medicinal Chemistry, vol. 9, No. 14, pp. 1633-1638, Dec. 1, 2009.
Presta, "Engineering of therapeutic antibodies to minimize immunogenicity and optimize function," Advanced Drug Delivery Reviews, Elsevier vol. 58, No. 5-6, pp. 640-656, Aug. 7, 2006.
Tang et al., "Cloning and characterization of cDNAs encoding four different canine immunoglobulin γ chains", Vet. Immunol. Immunopathal., 80:259-270, Aug. 2001.
Fan et al., "Investigating TrkA Expression in Canine Appendicular Osteosarcoma," J. Vet. Intern. Med., vol. 22, pp. 1181-1188, 2008.
Hanai, "Establishment of Humanized Antibody," Biotherapy, vol. 10, No. 11, pp. 1384-1391, Nov. 1996.
Richter et al., "Animal Pharmacokinetics of the Tumor Necrosis Factor Receptor-Immunoglobulin Fusion Protein Lenercept and their Extrapolation to Humans, Drug Metabolism and Disposition," vol. 27, No. 1, pp. 21-25, Jan. 1999.
Gearing et al., "A fully caninised anti-NGF monoclonal antibody for pain relief in dogs," BMC Veterinary Research, vol. 9, No. 226, pp. 1-11, Jan. 2013.

\* cited by examiner

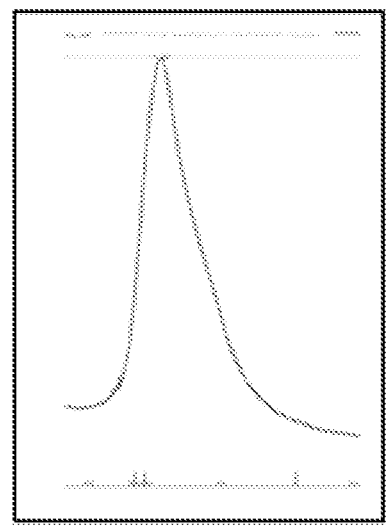
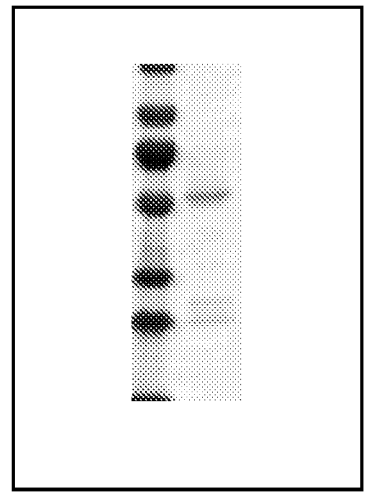
Figure 4

MGVPTQLLGLLLLWITDAIC**DIQMTQSPASLSASLGETVTIECR
ASEDIYNALAWYQQKPGKSPQLLIYNTDTLHTGVPSRFSGSG
SGTQYSLKINSLQSEDVASYFCQHYFHYPRTFGGGTKLELK**R
SDAQPSVFLFQPSLDELHTGSASIVCILNDFYPKEVNVKWKVD
GVVQTKASKESTTEQNSKDSTYSLSSTLTMSRTEYQSHEKFSC
EVTHKSLASTLVKSFNRSECQRE**

Figure 7 – Chimeric light chain

MAVLVLLLCLVTFPTCVLS**QVQLKESGPGLVQPSQTLSLTCTVSGFS
LTNNNVNWVRQATGRGLEWMGGVWAGGATDYNSALKSRLTITRD
TSKSQVFLKMHSLQSEDTATYYCARDGGYSSSTLYAMDAWGQGT
SVTVSS**ASTTAPSVFPLAPSCGTTSGATVALACLVLGYFPEPVTVSW
NSGALTSGVHTFPAVLQASGLYSLSSMVTVPSSRWLSDTFTCNVAH
PPSNTKVDKTVRKTDHPPGPKPCDCPKCPPPEMLGGPSIFIFPPKPK
DTLSISRTPEVTCLVVDLGPDDSDVQITWFVDNTQVYTAKTSPREEQ
FNSTYRVVSVLPILHQDWLKGKEFKCKVNSKSLPSPIERTISKAKGQP
HEPQVYVLPPAQEELSRNKVSVTCLIKSFHPPDIAVEWEITGQPEPE
NNYRTTPPQLDSDGTYFVYSKLSVDRSHWQRGNTYTCSVSHEALH
SHHTQKSLTQSPGK**

Figure 8 – Chimeric heavy chain

```
    *    *  *    ***    *** *                      *
DIVMTQTPLSLSVTPGEPASISCRASEDIYNALAWYLQKP  40

*  **                *           *** *  *****
GQSPRRLIYNTDTLHTGVPDRFSGSGSGTDFTLRISRVEA  80

*  **                     *      *
DDVGVYFCQHYFHYPRTFGPGTKLEIK  107
```

Figure 9 – Light chain variable domain

```
          *    **      *** *      **
QVQLVESGGDLVQPGGSLRLTCAASGFSLTNNNVNWVRQA  40

*  *                       *  *   *  **  ****
PGKGLEWMGGVWAGGATDYNSALKGRFTISRDNAKNTLYL  80

82ABC                  100ABCDEF
*  *   **                                 *
QMNSLKTEDTATYYCARDGGYSSSTLYAMDAWGQGTLVTVSS  113
```

Figure 10 – Heavy chain variable domain

**DIVMTQTPLSLSVTPGEPASISCRASEDIYNALAWYLQKPGQSP
RRLIYNTDTLHTGVPDRFSGSGSGTDFTLRISRVEADDVGVYFC
QHYFHYPRTFGPGTKLEIK**RSDAQPSVFLFQPSLDELHTGSASI
VCILNDFYPKEVNVKWKVDGVVQTKASKESTTEQNSKDSTYSL
SSTLTMSRTEYQSHEKFSCEVTHKSLASTLVKSFNRSECQRE

Figure 11 – Felinised anti-NGF VL kappa light chain

**QVQLVESGGDLVQPGGSLRLTCAASGFSLTNNNVNWVRQAPGK
GLEWMGGVWAGGATDYNSALKGRFTISRDNAKNTLYLQMNSLKT
EDTATYYCARDGGYSSSTLYAMDAWGQGTLVTVSS**ASTTAPSVF
PLAPSCGTTSGATVALACLVLGYFPEPVTVSWNSGALTSGVHTFPA
VLQASGLYSLSSMVTVPSSRWLSDTFTCNVAHPPSNTKVDKTVRK
TDHPPGPKPCDCPKCPPPEMLGGPSIFIFPPKPKDTLSISRTPEVTC
LVVDLGPDDSDVQITWFVDNTQVYTAKTSPREEQFNSTYRVVSVLP
ILHQDWLKGKEFKCKVNSKSLPSPIERTISKAKGQPHEPQVYVLPPA
QEELSRNKVSVTCLIKSFHPPDIAVEWEITGQPEPENNYRTTPPQLD
SDGTYFVYSKLSVDRSHWQRGNTYTCSVSHEALHSHHTQKSLTQS
PGK

Figure 12 –Felinised anti-NGF VH heavy chain

QVQLVESGAELVQPGESLRLTCAASGF<u>SLT
NNNVN</u>WVRQAPGKGLEWMGG<u>VWAGGATD
YNSALKS</u>RLTITRDTSKNTVFLQMHSLQSED
TATYYCAR<u>DGGYSSSTLYAMDA</u>WGQGTTV
TVSA

Figure 13 – Alternative felinised anti-NGF VH heavy chain (feN2-VH)

DIEMTQSPLSLSVTPGESVSISC<u>RASEDIYNA
LA</u>WYLQKPGRSPRLLIY<u>NTDTLHT</u>GVPDRFS
GSGSGTDFTLKISRVQTEDVGVYFC<u>QHYFH
YPRT</u>FGQGTKLELK

Figure 14 – Alternative felinised anti-NGF Vk light chain (feN2-Vk)

*MAVLVLLLCLVTFPTCVLS*QVQLVESGAELV
QPGESLRLTCAASGFSLTNNNVNWVRQAP
GKGLEWMGGVWAGGATDYNSALKSRLTIT
RDTSKNTVFLQMHSLQSEDTATYYCARDGG
YSSSTLYAMDAWGQGTTVTVSAASTTAPSV
FPLAPSCGTTSGATVALACLVLGYFPEPVTV
SWNSGALTSGVHTFPAVLQASGLYSLSSMV
TVPSSRWLSDTFTCNVAHPPSNTKVDKTVR
KTDHPPGPKPCDCPKCPPPEMLGGPSIFIFP
PKPKDTLSISRTPEVTCLVVDLGPDDSDVQIT
WFVDNTQVYTAKTSPREEQFNSTYRVVSVL
PILHQDWLKGKEFKCKVNSKSLPSPIERTISK
AKGQPHEPQVYVLPPAQEELSRNKVSVTCLI
KSFHPPDIAVEWEITGQPEPENNYRTTPPQL
DSDGTYFVYSKLSVDRSHWQRGNTYTCSV
SHEALHSHHTQKSLTQSPGK

Figure 15 – Alternative complete feline anti-NGF IgG
heavy chain (feN2-HC2)

*MGVPTQLLGLLLLWITDAIC*DIEMTQSPLSLS
VTPGESVSISCRASEDIYNALAWYLQKPGRS
PRLLIYNTDTLHTGVPDRFSGSGSGTDFTLKI
SRVQTEDVGVYFCQHYFHYPRTFGQGTKLE
LKRSDAQPSVFLFQPSLDELHTGSASIVCILN
DFYPKEVNVKWKVDGVVQTKASKESTTEQN
SKDSTYSLSSTLTMSRTEYQSHEKFSCEVT
HKSLASTLVKSFNRSECQRE

Figure 16 – Alternative complete feline anti-NGF IgG
kappa light chain (feN2-kLC)

SEQUENCE LISTING

```
<160> NUMBER OF SEQ ID NOS: 64

<210> SEQ ID NO 1
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full V+C light chain from chimeric

<400> SEQUENCE: 1

Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Asn Ala
            20                  25                  30
```

```
Leu Ala Trp Tyr Gln Gln Lys Pro Gly Lys Ser Pro Gln Leu Leu Ile
            35                  40                  45

Tyr Asn Thr Asp Thr Leu His Thr Gly Val Pro Ser Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Val Ala Ser Tyr Phe Cys Gln His Tyr Phe His Tyr Pro Arg
                 85                  90                  95

Thr Phe Gly Gly Gly Thr Lys Leu Glu Leu Lys Arg Ser Asp Ala Gln
            100                 105                 110

Pro Ser Val Phe Leu Phe Gln Pro Ser Leu Asp Glu Leu His Thr Gly
        115                 120                 125

Ser Ala Ser Ile Val Cys Ile Leu Asn Asp Phe Tyr Pro Lys Glu Val
    130                 135                 140

Asn Val Lys Trp Lys Val Asp Gly Val Val Gln Thr Lys Ala Ser Lys
145                 150                 155                 160

Glu Ser Thr Thr Glu Gln Asn Ser Lys Asp Ser Thr Tyr Ser Leu Ser
                165                 170                 175

Ser Thr Leu Thr Met Ser Arg Thr Glu Tyr Gln Ser His Glu Lys Phe
            180                 185                 190

Ser Cys Glu Val Thr His Lys Ser Leu Ala Ser Thr Leu Val Lys Ser
        195                 200                 205

Phe Asn Arg Ser Glu Cys Gln Arg Glu
    210                 215

<210> SEQ ID NO 2
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full V+C heavy chain from chimeric

<400> SEQUENCE: 2

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Asn Val Asn Trp Val Arg Gln Ala Thr Gly Arg Gly Leu Glu Trp Met
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Gln Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Ser Val Thr Val Ser Ser Ala Ser Thr Thr Ala Pro
        115                 120                 125

Ser Val Phe Pro Leu Ala Pro Ser Cys Gly Thr Thr Ser Gly Ala Thr
    130                 135                 140

Val Ala Leu Ala Cys Leu Val Leu Gly Tyr Phe Pro Glu Pro Val Thr
145                 150                 155                 160
```

```
Val Ser Trp Asn Ser Gly Ala Leu Thr Ser Gly Val His Thr Phe Pro
            165                 170                 175

Ala Val Leu Gln Ala Ser Gly Leu Tyr Ser Leu Ser Ser Met Val Thr
        180                 185                 190

Val Pro Ser Ser Arg Trp Leu Ser Asp Thr Phe Thr Cys Asn Val Ala
    195                 200                 205

His Pro Pro Ser Asn Thr Lys Val Asp Lys Thr Val Arg Lys Thr Asp
210                 215                 220

His Pro Pro Gly Pro Lys Pro Cys Asp Cys Pro Lys Cys Pro Pro Pro
225                 230                 235                 240

Glu Met Leu Gly Gly Pro Ser Ile Phe Ile Phe Pro Pro Lys Pro Lys
                245                 250                 255

Asp Thr Leu Ser Ile Ser Arg Thr Pro Glu Val Thr Cys Leu Val Val
            260                 265                 270

Asp Leu Gly Pro Asp Asp Ser Asp Val Gln Ile Thr Trp Phe Val Asp
        275                 280                 285

Asn Thr Gln Val Tyr Thr Ala Lys Thr Ser Pro Arg Glu Glu Gln Phe
    290                 295                 300

Asn Ser Thr Tyr Arg Val Val Ser Val Leu Pro Ile Leu His Gln Asp
305                 310                 315                 320

Trp Leu Lys Gly Lys Glu Phe Lys Cys Lys Val Asn Ser Lys Ser Leu
                325                 330                 335

Pro Ser Pro Ile Glu Arg Thr Ile Ser Lys Ala Lys Gly Gln Pro His
            340                 345                 350

Glu Pro Gln Val Tyr Val Leu Pro Pro Ala Gln Glu Glu Leu Ser Arg
        355                 360                 365

Asn Lys Val Ser Val Thr Cys Leu Ile Lys Ser Phe His Pro Pro Asp
    370                 375                 380

Ile Ala Val Glu Trp Glu Ile Thr Gly Gln Pro Glu Pro Glu Asn Asn
385                 390                 395                 400

Tyr Arg Thr Thr Pro Pro Gln Leu Asp Ser Asp Gly Thr Tyr Phe Val
                405                 410                 415

Tyr Ser Lys Leu Ser Val Asp Arg Ser His Trp Gln Arg Gly Asn Thr
            420                 425                 430

Tyr Thr Cys Ser Val Ser His Glu Ala Leu His Ser His His Thr Gln
        435                 440                 445

Lys Ser Leu Thr Gln Ser Pro Gly Lys
    450                 455

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable domain from felinised

<400> SEQUENCE: 3

Asp Ile Val Met Thr Gln Thr Pro Leu Ser Leu Ser Val Thr Pro Gly
1               5                   10                  15

Glu Pro Ala Ser Ile Ser Cys Arg Ala Ser Glu Asp Ile Tyr Asn Ala
            20                  25                  30

Leu Ala Trp Tyr Leu Gln Lys Pro Gly Gln Ser Pro Arg Arg Leu Ile
        35                  40                  45
```

```
Tyr Asn Thr Asp Thr Leu His Thr Gly Val Pro Asp Arg Phe Ser Gly
         50                  55                  60

Ser Gly Ser Gly Thr Asp Phe Thr Leu Arg Ile Ser Arg Val Glu Ala
 65                  70                  75                  80

Asp Asp Val Gly Val Tyr Phe Cys Gln His Tyr Phe His Tyr Pro Arg
                 85                  90                  95

Thr Phe Gly Pro Gly Thr Lys Leu Glu Ile Lys
            100                 105

<210> SEQ ID NO 4
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable domain from felinised (HC
      derived from BAA32229.1)

<400> SEQUENCE: 4

Gln Val Gln Leu Val Glu Ser Gly Gly Asp Leu Val Gln Pro Gly Gly
 1               5                  10                  15

Ser Leu Arg Leu Thr Cys Ala Ala Ser Gly Phe Ser Leu Thr Asn Asn
                 20                  25                  30

Asn Val Asn Trp Val Arg Gln Ala Pro Gly Lys Gly Leu Glu Trp Met
             35                  40                  45

Gly Gly Val Trp Ala Gly Gly Ala Thr Asp Tyr Asn Ser Ala Leu Lys
         50                  55                  60

Gly Arg Phe Thr Ile Ser Arg Asp Asn Ala Lys Asn Thr Leu Tyr Leu
 65                  70                  75                  80

Gln Met Asn Ser Leu Lys Thr Glu Asp Thr Ala Thr Tyr Tyr Cys Ala
                 85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser
        115                 120

<210> SEQ ID NO 5
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full light chain from felinised

<400> SEQUENCE: 5

Asp Ile Val Met Thr Gln Thr Pro Leu Ser Leu Ser Val Thr Pro Gly
 1               5                  10                  15

Glu Pro Ala Ser Ile Ser Cys Arg Ala Ser Glu Asp Ile Tyr Asn Ala
                 20                  25                  30

Leu Ala Trp Tyr Leu Gln Lys Pro Gly Gln Ser Pro Arg Arg Leu Ile
             35                  40                  45

Tyr Asn Thr Asp Thr Leu His Thr Gly Val Pro Asp Arg Phe Ser Gly
         50                  55                  60

Ser Gly Ser Gly Thr Asp Phe Thr Leu Arg Ile Ser Arg Val Glu Ala
 65                  70                  75                  80
```

Asp Asp Val Gly Val Tyr Phe Cys Gln His Tyr Phe His Tyr Pro Arg
                85                  90                  95

Thr Phe Gly Pro Gly Thr Lys Leu Glu Ile Lys Arg Ser Asp Ala Gln
            100                 105                 110

Pro Ser Val Phe Leu Phe Gln Pro Ser Leu Asp Glu Leu His Thr Gly
            115                 120                 125

Ser Ala Ser Ile Val Cys Ile Leu Asn Asp Phe Tyr Pro Lys Glu Val
        130                 135                 140

Asn Val Lys Trp Lys Val Asp Gly Val Val Gln Thr Lys Ala Ser Lys
145                 150                 155                 160

Glu Ser Thr Thr Glu Gln Asn Ser Lys Asp Ser Thr Tyr Ser Leu Ser
                165                 170                 175

Ser Thr Leu Thr Met Ser Arg Thr Glu Tyr Gln Ser His Glu Lys Phe
            180                 185                 190

Ser Cys Glu Val Thr His Lys Ser Leu Ala Ser Thr Leu Val Lys Ser
        195                 200                 205

Phe Asn Arg Ser Glu Cys Gln Arg Glu
    210                 215

<210> SEQ ID NO 6
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full heavy chain from felinised (HC derived
      from BAA32229.1)

<400> SEQUENCE: 6

Gln Val Gln Leu Val Glu Ser Gly Gly Asp Leu Val Gln Pro Gly Gly
1               5                   10                  15

Ser Leu Arg Leu Thr Cys Ala Ala Ser Gly Phe Ser Leu Thr Asn Asn
            20                  25                  30

Asn Val Asn Trp Val Arg Gln Ala Pro Gly Lys Gly Leu Glu Trp Met
        35                  40                  45

Gly Gly Val Trp Ala Gly Gly Ala Thr Asp Tyr Asn Ser Ala Leu Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Thr Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Thr Thr Ser Gly Ala Thr
    130                 135                 140

Val Ala Leu Ala Cys Leu Val Leu Gly Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ala Ser Gly Leu Tyr Ser Leu Ser Ser Met Val Thr
            180                 185                 190

Val Pro Ser Ser Arg Trp Leu Ser Asp Thr Phe Thr Cys Asn Val Ala
        195                 200                 205

His Pro Pro Ser Asn Thr Lys Val Asp Lys Thr Val Arg Lys Thr Asp
    210                 215                 220

His Pro Pro Gly Pro Lys Pro Cys Asp Cys Pro Lys Cys Pro Pro Pro
225                 230                 235                 240

Glu Met Leu Gly Gly Pro Ser Ile Phe Ile Phe Pro Pro Lys Pro Lys
                245                 250                 255

Asp Thr Leu Ser Ile Ser Arg Thr Pro Glu Val Thr Cys Leu Val Val
                260                 265                 270

Asp Leu Gly Pro Asp Asp Ser Asp Val Gln Ile Thr Trp Phe Val Asp
            275                 280                 285

Asn Thr Gln Val Tyr Thr Ala Lys Thr Ser Pro Arg Glu Glu Gln Phe
    290                 295                 300

Asn Ser Thr Tyr Arg Val Val Ser Val Leu Pro Ile Leu His Gln Asp
305                 310                 315                 320

Trp Leu Lys Gly Lys Glu Phe Lys Cys Lys Val Asn Ser Lys Ser Leu
                325                 330                 335

Pro Ser Pro Ile Glu Arg Thr Ile Ser Lys Ala Lys Gly Gln Pro His
            340                 345                 350

Glu Pro Gln Val Tyr Val Leu Pro Pro Ala Gln Glu Glu Leu Ser Arg
    355                 360                 365

Asn Lys Val Ser Val Thr Cys Leu Ile Lys Ser Phe His Pro Pro Asp
370                 375                 380

Ile Ala Val Glu Trp Glu Ile Thr Gly Gln Pro Glu Pro Glu Asn Asn
385                 390                 395                 400

Tyr Arg Thr Thr Pro Pro Gln Leu Asp Ser Asp Gly Thr Tyr Phe Val
                405                 410                 415

Tyr Ser Lys Leu Ser Val Asp Arg Ser His Trp Gln Arg Gly Asn Thr
            420                 425                 430

Tyr Thr Cys Ser Val Ser His Glu Ala Leu His Ser His His Thr Gln
    435                 440                 445

Lys Ser Leu Thr Gln Ser Pro Gly Lys
    450                 455

<210> SEQ ID NO 7
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Aglycosylated full heavy chain from felinised
      (modified HC from BAA32229.1)

<400> SEQUENCE: 7

Gln Val Gln Leu Val Glu Ser Gly Gly Asp Leu Val Gln Pro Gly Gly
1               5                   10                  15

Ser Leu Arg Leu Thr Cys Ala Ala Ser Gly Phe Ser Leu Thr Asn Asn
            20                  25                  30

Asn Val Asn Trp Val Arg Gln Ala Pro Gly Lys Gly Leu Glu Trp Met
        35                  40                  45

Gly Gly Val Trp Ala Gly Gly Ala Thr Asp Tyr Asn Ser Ala Leu Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Thr Glu Asp Thr Ala Thr Tyr Tyr Cys Ala

```
                    85                  90                  95
Arg Asp Gly Gly Tyr Ser Ser Thr Leu Tyr Ala Met Asp Ala Trp
                100                 105                 110

Gly Gln Gly Thr Leu Val Thr Val Ser Ser Ala Ser Thr Ala Pro
                115                 120                 125

Ser Val Phe Pro Leu Ala Pro Ser Cys Gly Thr Thr Ser Gly Ala Thr
130                 135                 140

Val Ala Leu Ala Cys Leu Val Leu Gly Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ala Ser Gly Leu Tyr Ser Leu Ser Ser Met Val Thr
                180                 185                 190

Val Pro Ser Ser Arg Trp Leu Ser Asp Thr Phe Thr Cys Asn Val Ala
                195                 200                 205

His Pro Pro Ser Asn Thr Lys Val Asp Lys Thr Val Arg Lys Thr Asp
                210                 215                 220

His Pro Pro Gly Pro Lys Pro Cys Asp Cys Pro Lys Cys Pro Pro Pro
225                 230                 235                 240

Glu Met Leu Gly Gly Pro Ser Ile Phe Ile Phe Pro Pro Lys Pro Lys
                245                 250                 255

Asp Thr Leu Ser Ile Ser Arg Thr Pro Glu Val Thr Cys Leu Val Val
                260                 265                 270

Asp Leu Gly Pro Asp Asp Ser Asp Val Gln Ile Thr Trp Phe Val Asp
                275                 280                 285

Asn Thr Gln Val Tyr Thr Ala Lys Thr Ser Pro Arg Glu Glu Gln Phe
                290                 295                 300

Ala Ser Thr Tyr Arg Val Val Ser Val Leu Pro Ile Leu His Gln Asp
305                 310                 315                 320

Trp Leu Lys Gly Lys Glu Phe Lys Cys Lys Val Asn Ser Lys Ser Leu
                325                 330                 335

Pro Ser Pro Ile Glu Arg Thr Ile Ser Lys Ala Lys Gly Gln Pro His
                340                 345                 350

Glu Pro Gln Val Tyr Val Leu Pro Pro Ala Gln Glu Glu Leu Ser Arg
                355                 360                 365

Asn Lys Val Ser Val Thr Cys Leu Ile Lys Ser Phe His Pro Pro Asp
                370                 375                 380

Ile Ala Val Glu Trp Glu Ile Thr Gly Gln Pro Glu Pro Glu Asn Asn
385                 390                 395                 400

Tyr Arg Thr Thr Pro Pro Gln Leu Asp Ser Asp Gly Thr Tyr Phe Val
                405                 410                 415

Tyr Ser Lys Leu Ser Val Asp Arg Ser His Trp Gln Arg Gly Asn Thr
                420                 425                 430

Tyr Thr Cys Ser Val Ser His Glu Ala Leu His Ser His His Thr Gln
                435                 440                 445

Lys Ser Leu Thr Gln Ser Pro Gly Lys
450                 455

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Light chain FR1

<400> SEQUENCE: 8

Asp Ile Val Met Thr Gln Thr Pro Leu Ser Leu Ser Val Thr Pro Gly
1               5                   10                  15

Glu Pro Ala Ser Ile Ser Cys
            20

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Light chain FR2

<400> SEQUENCE: 9

Trp Tyr Leu Gln Lys Pro Gly Gln Ser Pro Arg Arg Leu Ile Tyr
1               5                   10                  15

<210> SEQ ID NO 10
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain FR3

<400> SEQUENCE: 10

Gly Val Pro Asp Arg Phe Ser Gly Ser Gly Ser Gly Thr Asp Phe Thr
1               5                   10                  15

Leu Arg Ile Ser Arg Val Glu Ala Asp Asp Val Gly Val Tyr Phe Cys
            20                  25                  30

Gln

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Light chain FR4

<400> SEQUENCE: 11

Phe Gly Pro Gly Thr Lys Leu Glu Ile Lys
1               5                   10

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain FR1

<400> SEQUENCE: 12

Gln Val Gln Leu Val Glu Ser Gly Gly Asp Leu Val Gln Pro Gly Gly
1               5                   10                  15
```

Ser Leu Arg Leu Thr Cys Ala Ala Ser Gly Phe Ser Leu Thr
            20                  25                  30

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Heavy chain FR2

<400> SEQUENCE: 13

Trp Val Arg Gln Ala Pro Gly Lys Gly Leu Glu Trp Met Gly
1               5                   10

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain FR3

<400> SEQUENCE: 14

Arg Phe Thr Ile Ser Arg Asp Asn Ala Lys Asn Thr Leu Tyr Leu Gln
1               5                   10                  15

Met Asn Ser Leu Lys Thr Glu Asp Thr Ala Thr Tyr Tyr Cys Ala Arg
            20                  25                  30

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Heavy chain FR4

<400> SEQUENCE: 15

Trp Gly Gln Gly Thr Leu Val Thr Val Ser Ser
1               5                   10

<210> SEQ ID NO 16
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Alternate full V+C heavy chain chimera
      (Chimeric anti-NGF alternate HC constant domain from BAA32230.1)

<400> SEQUENCE: 16

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Asn Val Asn Trp Val Arg Gln Ala Thr Gly Arg Gly Leu Glu Trp Met
        35                  40                  45

Gly Gly Val Trp Ala Gly Gly Ala Thr Asp Tyr Asn Ser Ala Leu Lys

```
            50                  55                  60
Ser Arg Leu Thr Ile Thr Arg Asp Thr Ser Lys Ser Gln Val Phe Leu
 65                  70                  75                  80

Lys Met His Ser Leu Gln Ser Glu Asp Thr Ala Thr Tyr Tyr Cys Ala
                 85                  90                  95

Arg Asp Gly Gly Tyr Ser Ser Thr Leu Tyr Ala Met Asp Ala Trp
            100                 105                 110

Gly Gln Gly Thr Ser Val Thr Val Ser Ser Ala Ser Thr Thr Ala Pro
            115                 120                 125

Ser Val Phe Pro Leu Ala Pro Ser Cys Gly Thr Thr Ser Gly Ala Thr
            130                 135                 140

Val Ala Leu Ala Cys Leu Val Leu Gly Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ala Ser Gly Leu Tyr Ser Leu Ser Ser Met Val Thr
                180                 185                 190

Val Pro Ser Ser Arg Trp Leu Ser Asp Thr Phe Thr Cys Asn Val Ala
                195                 200                 205

His Pro Pro Ser Asn Thr Lys Val Asp Lys Thr Val Arg Lys Thr Asp
210                 215                 220

His Pro Pro Gly Pro Lys Pro Cys Asp Cys Pro Lys Cys Pro Pro Pro
225                 230                 235                 240

Glu Met Leu Gly Gly Pro Ser Ile Phe Ile Phe Pro Pro Lys Pro Lys
                245                 250                 255

Asp Thr Leu Ser Ile Ser Arg Thr Pro Glu Val Thr Cys Leu Val Val
                260                 265                 270

Asp Leu Gly Pro Asp Asp Ser Asp Val Gln Ile Thr Trp Phe Val Asp
                275                 280                 285

Asn Thr Gln Val Tyr Thr Ala Lys Thr Ser Pro Arg Glu Glu Gln Phe
290                 295                 300

Asn Ser Thr Tyr Arg Val Val Ser Val Leu Pro Ile Leu His Gln Asp
305                 310                 315                 320

Trp Leu Lys Gly Lys Glu Phe Lys Cys Lys Val Asn Ser Lys Ser Leu
                325                 330                 335

Pro Ser Pro Ile Glu Arg Thr Ile Ser Lys Asp Lys Gly Gln Pro His
                340                 345                 350

Glu Pro Gln Val Tyr Val Leu Pro Pro Ala Gln Glu Glu Leu Ser Arg
                355                 360                 365

Asn Lys Val Ser Val Thr Cys Leu Ile Glu Gly Phe Tyr Pro Ser Asp
370                 375                 380

Ile Ala Val Glu Trp Glu Ile Thr Gly Gln Pro Glu Pro Glu Asn Asn
385                 390                 395                 400

Tyr Arg Thr Thr Pro Pro Gln Leu Asp Ser Asp Gly Thr Tyr Phe Leu
                405                 410                 415

Tyr Ser Arg Leu Ser Val Asp Arg Ser Arg Trp Gln Arg Gly Asn Thr
                420                 425                 430

Tyr Thr Cys Ser Val Ser His Glu Ala Leu His Ser His His Thr Gln
                435                 440                 445

Lys Ser Leu Thr Gln Ser Pro Gly Lys
        450                 455

<210> SEQ ID NO 17
```

```
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Alternate full heavy chain from felinised
      (Felinised anti-NGF V domain fused to alternate HC constant domain
      from BAA32230.1)

<400> SEQUENCE: 17
```

Gln Val Gln Leu Val Glu Ser Gly Gly Asp Leu Val Gln Pro Gly Gly
1               5                   10                  15

Ser Leu Arg Leu Thr Cys Ala Ala Ser Gly Phe Ser Leu Thr Asn Asn
            20                  25                  30

Asn Val Asn Trp Val Arg Gln Ala Pro Gly Lys Gly Leu Glu Trp Met
        35                  40                  45

Gly Gly Val Trp Ala Gly Gly Ala Thr Asp Tyr Asn Ser Ala Leu Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Thr Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Thr Thr Ser Gly Ala Thr
    130                 135                 140

Val Ala Leu Ala Cys Leu Val Leu Gly Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ala Ser Gly Leu Tyr Ser Leu Ser Ser Met Val Thr
            180                 185                 190

Val Pro Ser Ser Arg Trp Leu Ser Asp Thr Phe Thr Cys Asn Val Ala
        195                 200                 205

His Pro Pro Ser Asn Thr Lys Val Asp Lys Thr Val Arg Lys Thr Asp
    210                 215                 220

His Pro Pro Gly Pro Lys Pro Cys Asp Cys Pro Lys Cys Pro Pro Pro
225                 230                 235                 240

Glu Met Leu Gly Gly Pro Ser Ile Phe Ile Phe Pro Pro Lys Pro Lys
                245                 250                 255

Asp Thr Leu Ser Ile Ser Arg Thr Pro Glu Val Thr Cys Leu Val Val
            260                 265                 270

Asp Leu Gly Pro Asp Asp Ser Asp Val Gln Ile Thr Trp Phe Val Asp
        275                 280                 285

Asn Thr Gln Val Tyr Thr Ala Lys Thr Ser Pro Arg Glu Glu Gln Phe
    290                 295                 300

Asn Ser Thr Tyr Arg Val Val Ser Val Leu Pro Ile Leu His Gln Asp
305                 310                 315                 320

Trp Leu Lys Gly Lys Glu Phe Lys Cys Lys Val Asn Ser Lys Ser Leu
                325                 330                 335

Pro Ser Pro Ile Glu Arg Thr Ile Ser Lys Asp Lys Gly Gln Pro His
            340                 345                 350

```
Glu Pro Gln Val Tyr Val Leu Pro Pro Ala Gln Glu Leu Ser Arg
            355                 360                 365

Asn Lys Val Ser Val Thr Cys Leu Ile Glu Gly Phe Tyr Pro Ser Asp
    370                 375                 380

Ile Ala Val Glu Trp Glu Ile Thr Gly Gln Pro Glu Pro Glu Asn Asn
385                 390                 395                 400

Tyr Arg Thr Thr Pro Pro Gln Leu Asp Ser Asp Gly Thr Tyr Phe Leu
                405                 410                 415

Tyr Ser Arg Leu Ser Val Asp Arg Ser Arg Trp Gln Arg Gly Asn Thr
                420                 425                 430

Tyr Thr Cys Ser Val Ser His Glu Ala Leu His Ser His His Thr Gln
            435                 440                 445

Lys Ser Leu Thr Gln Ser Pro Gly Lys
    450                 455

<210> SEQ ID NO 18
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Aglycosyl Alternate full heavy chain from
      felinised (Felinised anti-NGF V domain fused to alternate HC
      constant domain from BAA32230.1, with N-glycolylation site
      substituted)

<400> SEQUENCE: 18

Gln Val Gln Leu Val Glu Ser Gly Gly Asp Leu Val Gln Pro Gly Gly
1               5                   10                  15

Ser Leu Arg Leu Thr Cys Ala Ala Ser Gly Phe Ser Leu Thr Asn Asn
            20                  25                  30

Asn Val Asn Trp Val Arg Gln Ala Pro Gly Lys Gly Leu Glu Trp Met
        35                  40                  45

Gly Gly Val Trp Ala Gly Gly Ala Thr Asp Tyr Asn Ser Ala Leu Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Thr Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Thr Thr Ser Gly Ala Thr
    130                 135                 140

Val Ala Leu Ala Cys Leu Val Leu Gly Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ala Ser Gly Leu Tyr Ser Leu Ser Ser Met Val Thr
            180                 185                 190

Val Pro Ser Ser Arg Trp Leu Ser Asp Thr Phe Thr Cys Asn Val Ala
        195                 200                 205

His Pro Pro Ser Asn Thr Lys Val Asp Lys Thr Val Arg Lys Thr Asp
    210                 215                 220
```

His Pro Pro Gly Pro Lys Pro Cys Asp Cys Pro Lys Cys Pro Pro Pro
225                 230                 235                 240

Glu Met Leu Gly Gly Pro Ser Ile Phe Ile Phe Pro Pro Lys Pro Lys
            245                 250                 255

Asp Thr Leu Ser Ile Ser Arg Thr Pro Glu Val Thr Cys Leu Val Val
        260                 265                 270

Asp Leu Gly Pro Asp Asp Ser Asp Val Gln Ile Thr Trp Phe Val Asp
    275                 280                 285

Asn Thr Gln Val Tyr Thr Ala Lys Thr Ser Pro Arg Glu Glu Gln Phe
290                 295                 300

Ala Ser Thr Tyr Arg Val Val Ser Val Leu Pro Ile Leu His Gln Asp
305                 310                 315                 320

Trp Leu Lys Gly Lys Glu Phe Lys Cys Lys Val Asn Ser Lys Ser Leu
            325                 330                 335

Pro Ser Pro Ile Glu Arg Thr Ile Ser Lys Asp Lys Gly Gln Pro His
        340                 345                 350

Glu Pro Gln Val Tyr Val Leu Pro Pro Ala Gln Glu Glu Leu Ser Arg
    355                 360                 365

Asn Lys Val Ser Val Thr Cys Leu Ile Glu Gly Phe Tyr Pro Ser Asp
370                 375                 380

Ile Ala Val Glu Trp Glu Ile Thr Gly Gln Pro Glu Pro Glu Asn Asn
385                 390                 395                 400

Tyr Arg Thr Thr Pro Pro Gln Leu Asp Ser Asp Gly Thr Tyr Phe Leu
            405                 410                 415

Tyr Ser Arg Leu Ser Val Asp Arg Ser Arg Trp Gln Arg Gly Asn Thr
        420                 425                 430

Tyr Thr Cys Ser Val Ser His Glu Ala Leu His Ser His His Thr Gln
    435                 440                 445

Lys Ser Leu Thr Gln Ser Pro Gly Lys
450                 455

<210> SEQ ID NO 19
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Aglycosyl chimeric HC (derived from SEQ ID
      NO:2)

<400> SEQUENCE: 19

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Asn Val Asn Trp Val Arg Gln Ala Thr Gly Arg Gly Leu Glu Trp Met
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Gln Val Phe Leu
65                  70                  75                  80

Lys Met His Ser Leu Gln Ser Glu Asp Thr Ala Thr Tyr Tyr Cys Ala
            85                  90                  95

Arg Asp Gly Gly Tyr Ser Ser Ser Thr Leu Tyr Ala Met Asp Ala Trp
        100                 105                 110

Gly Gln Gly Thr Ser Val Thr Val Ser Ser Ala Ser Thr Ala Pro
            115                 120                 125

Ser Val Phe Pro Leu Ala Pro Ser Cys Gly Thr Thr Ser Gly Ala Thr
130                 135                 140

Val Ala Leu Ala Cys Leu Val Leu Gly Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ala Ser Gly Leu Tyr Ser Leu Ser Ser Met Val Thr
            180                 185                 190

Val Pro Ser Ser Arg Trp Leu Ser Asp Thr Phe Thr Cys Asn Val Ala
            195                 200                 205

His Pro Pro Ser Asn Thr Lys Val Asp Lys Thr Val Arg Lys Thr Asp
210                 215                 220

His Pro Pro Gly Pro Lys Pro Cys Asp Cys Pro Lys Cys Pro Pro Pro
225                 230                 235                 240

Glu Met Leu Gly Gly Pro Ser Ile Phe Ile Phe Pro Pro Lys Pro Lys
                245                 250                 255

Asp Thr Leu Ser Ile Ser Arg Thr Pro Glu Val Thr Cys Leu Val Val
            260                 265                 270

Asp Leu Gly Pro Asp Asp Ser Asp Val Gln Ile Thr Trp Phe Val Asp
            275                 280                 285

Asn Thr Gln Val Tyr Thr Ala Lys Thr Ser Pro Arg Glu Glu Gln Phe
290                 295                 300

Ala Ser Thr Tyr Arg Val Val Ser Val Leu Pro Ile Leu His Gln Asp
305                 310                 315                 320

Trp Leu Lys Gly Lys Glu Phe Lys Cys Lys Val Asn Ser Lys Ser Leu
                325                 330                 335

Pro Ser Pro Ile Glu Arg Thr Ile Ser Lys Ala Lys Gly Gln Pro His
            340                 345                 350

Glu Pro Gln Val Tyr Val Leu Pro Pro Ala Gln Glu Glu Leu Ser Arg
            355                 360                 365

Asn Lys Val Ser Val Thr Cys Leu Ile Lys Ser Phe His Pro Pro Asp
370                 375                 380

Ile Ala Val Glu Trp Glu Ile Thr Gly Gln Pro Glu Pro Glu Asn Asn
385                 390                 395                 400

Tyr Arg Thr Thr Pro Pro Gln Leu Asp Ser Asp Gly Thr Tyr Phe Val
                405                 410                 415

Tyr Ser Lys Leu Ser Val Asp Arg Ser His Trp Gln Arg Gly Asn Thr
            420                 425                 430

Tyr Thr Cys Ser Val Ser His Glu Ala Leu His Ser His His Thr Gln
            435                 440                 445

Lys Ser Leu Thr Gln Ser Pro Gly Lys
    450                 455

<210> SEQ ID NO 20
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain of chimeric feline-rat antibody
      with leader sequence

<400> SEQUENCE: 20

```
Met Gly Val Pro Thr Gln Leu Gly Leu Leu Leu Trp Ile Thr
1               5                   10                  15

Asp Ala Ile Cys Asp Ile Gln Met Thr Gln Ser Pro Ala Ser Leu Ser
            20                  25                  30

Ala Ser Leu Gly Glu Thr Val Thr Ile Glu Cys Arg Ala Ser Glu Asp
        35                  40                  45

Ile Tyr Asn Ala Leu Ala Trp Tyr Gln Gln Lys Pro Gly Lys Ser Pro
    50                  55                  60

Gln Leu Leu Ile Tyr Asn Thr Asp Thr Leu His Thr Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Ser Tyr Phe Cys Gln His Tyr Phe
            100                 105                 110

His Tyr Pro Arg Thr Phe Gly Gly Gly Thr Lys Leu Glu Leu Lys Arg
        115                 120                 125

Ser Asp Ala Gln Pro Ser Val Phe Leu Phe Gln Pro Ser Leu Asp Glu
    130                 135                 140

Leu His Thr Gly Ser Ala Ser Ile Val Cys Ile Leu Asn Asp Phe Tyr
145                 150                 155                 160

Pro Lys Glu Val Asn Val Lys Trp Lys Val Asp Gly Val Val Gln Thr
                165                 170                 175

Lys Ala Ser Lys Glu Ser Thr Thr Glu Gln Asn Ser Lys Asp Ser Thr
            180                 185                 190

Tyr Ser Leu Ser Ser Thr Leu Thr Met Ser Arg Thr Glu Tyr Gln Ser
        195                 200                 205

His Glu Lys Phe Ser Cys Glu Val Thr His Lys Ser Leu Ala Ser Thr
    210                 215                 220

Leu Val Lys Ser Phe Asn Arg Ser Glu Cys Gln Arg Glu
225                 230                 235
```

<210> SEQ ID NO 21
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain of chimeric feline-rat antibody
      with leader sequence

<400> SEQUENCE: 21

```
Met Ala Val Leu Val Leu Leu Cys Leu Val Thr Phe Pro Thr Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Asn Asn Asn Val Asn Trp Val Arg Gln Ala Thr Gly Arg Gly Leu
    50                  55                  60

Glu Trp Met Gly Gly Val Trp Ala Gly Gly Ala Thr Asp Tyr Asn Ser
65                  70                  75                  80

Ala Leu Lys Ser Arg Leu Thr Ile Thr Arg Asp Thr Ser Lys Ser Gln
                85                  90                  95
```

```
Val Phe Leu Lys Met His Ser Leu Gln Ser Glu Asp Thr Ala Thr Tyr
            100                 105                 110

Tyr Cys Ala Arg Asp Gly Gly Tyr Ser Ser Thr Leu Tyr Ala Met
        115                 120                 125

Asp Ala Trp Gly Gln Gly Thr Ser Val Thr Val Ser Ser Ala Ser Thr
    130                 135                 140

Thr Ala Pro Ser Val Phe Pro Leu Ala Pro Ser Cys Gly Thr Thr Ser
145                 150                 155                 160

Gly Ala Thr Val Ala Leu Ala Cys Leu Val Leu Gly Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ala Ser Gly Leu Tyr Ser Leu Ser Ser
        195                 200                 205

Met Val Thr Val Pro Ser Ser Arg Trp Leu Ser Asp Thr Phe Thr Cys
        210                 215                 220

Asn Val Ala His Pro Pro Ser Asn Thr Lys Val Asp Lys Thr Val Arg
225                 230                 235                 240

Lys Thr Asp His Pro Pro Gly Pro Lys Pro Cys Asp Cys Pro Lys Cys
                245                 250                 255

Pro Pro Pro Glu Met Leu Gly Gly Pro Ser Ile Phe Ile Phe Pro Pro
                260                 265                 270

Lys Pro Lys Asp Thr Leu Ser Ile Ser Arg Thr Pro Glu Val Thr Cys
                275                 280                 285

Leu Val Val Asp Leu Gly Pro Asp Asp Ser Asp Val Gln Ile Thr Trp
        290                 295                 300

Phe Val Asp Asn Thr Gln Val Tyr Thr Ala Lys Thr Ser Pro Arg Glu
305                 310                 315                 320

Glu Gln Phe Asn Ser Thr Tyr Arg Val Val Ser Val Leu Pro Ile Leu
                325                 330                 335

His Gln Asp Trp Leu Lys Gly Lys Glu Phe Lys Cys Lys Val Asn Ser
                340                 345                 350

Lys Ser Leu Pro Ser Pro Ile Glu Arg Thr Ile Ser Lys Ala Lys Gly
        355                 360                 365

Gln Pro His Glu Pro Gln Val Tyr Val Leu Pro Pro Ala Gln Glu Glu
        370                 375                 380

Leu Ser Arg Asn Lys Val Ser Val Thr Cys Leu Ile Lys Ser Phe His
385                 390                 395                 400

Pro Pro Asp Ile Ala Val Glu Trp Glu Ile Thr Gly Gln Pro Glu Pro
                405                 410                 415

Glu Asn Asn Tyr Arg Thr Thr Pro Pro Gln Leu Asp Ser Asp Gly Thr
                420                 425                 430

Tyr Phe Val Tyr Ser Lys Leu Ser Val Asp Arg Ser His Trp Gln Arg
        435                 440                 445

Gly Asn Thr Tyr Thr Cys Ser Val Ser His Glu Ala Leu His Ser His
        450                 455                 460

His Thr Gln Lys Ser Leu Thr Gln Ser Pro Gly Lys
465                 470                 475

<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
```

-continued

```
         polypeptide
<220> FEATURE:
<223> OTHER INFORMATION: Alternative felinised anti-NGF VH heavy chain
      (feN2-VH)

<400> SEQUENCE: 22

Gln Val Gln Leu Val Glu Ser Gly Ala Glu Leu Val Gln Pro Gly Glu
1               5                   10                  15

Ser Leu Arg Leu Thr Cys Ala Ala Ser Gly Phe Ser Leu Thr Asn Asn
            20                  25                  30

Asn Val Asn Trp Val Arg Gln Ala Pro Gly Lys Gly Leu Glu Trp Met
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Asn Thr Val Phe Leu
65                  70                  75                  80

Gln Met His Ser Leu Gln Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Thr Val Thr Val Ser Ala
        115                 120

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Alternative felinised anti-NGF Vk light chain
      (feN2-Vk)

<400> SEQUENCE: 23

Asp Ile Glu Met Thr Gln Ser Pro Leu Ser Leu Ser Val Thr Pro Gly
1               5                   10                  15

Glu Ser Val Ser Ile Ser Cys Arg Ala Ser Glu Asp Ile Tyr Asn Ala
            20                  25                  30

Leu Ala Trp Tyr Leu Gln Lys Pro Gly Arg Ser Pro Arg Leu Leu Ile
        35                  40                  45

Tyr Asn Thr Asp Thr Leu His Thr Gly Val Pro Asp Arg Phe Ser Gly
    50                  55                  60

Ser Gly Ser Gly Thr Asp Phe Thr Leu Lys Ile Ser Arg Val Gln Thr
65                  70                  75                  80

Glu Asp Val Gly Val Tyr Phe Cys Gln His Tyr Phe His Tyr Pro Arg
                85                  90                  95

Thr Phe Gly Gln Gly Thr Lys Leu Glu Leu Lys
            100                 105

<210> SEQ ID NO 24
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Alternative complete feline anti-NGF IgG heavy
      chain (feN2-HC2)

<400> SEQUENCE: 24
```

-continued

```
Met Ala Val Leu Val Leu Leu Cys Leu Val Thr Phe Pro Thr Cys
1               5                   10                  15

Val Leu Ser Gln Val Gln Leu Val Glu Ser Gly Ala Glu Leu Val Gln
            20                  25                  30

Pro Gly Glu Ser Leu Arg Leu Thr Cys Ala Ala Ser Gly Phe Ser Leu
            35                  40                  45

Thr Asn Asn Val Asn Trp Val Arg Gln Ala Pro Gly Lys Gly Leu
    50                  55                  60

Glu Trp Met Gly Gly Val Trp Ala Gly Gly Ala Thr Asp Tyr Asn Ser
65                  70                  75                  80

Ala Leu Lys Ser Arg Leu Thr Ile Thr Arg Asp Thr Ser Lys Asn Thr
                85                  90                  95

Val Phe Leu Gln Met His Ser Leu Gln Ser Glu Asp Thr Ala Thr Tyr
                100                 105                 110

Tyr Cys Ala Arg Asp Gly Gly Tyr Ser Ser Ser Thr Leu Tyr Ala Met
        115                 120                 125

Asp Ala Trp Gly Gln Gly Thr Thr Val Thr Val Ser Ala Ala Ser Thr
130                 135                 140

Thr Ala Pro Ser Val Phe Pro Leu Ala Pro Ser Cys Gly Thr Thr Ser
145                 150                 155                 160

Gly Ala Thr Val Ala Leu Ala Cys Leu Val Leu Gly Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ala Ser Gly Leu Tyr Ser Leu Ser Ser
            195                 200                 205

Met Val Thr Val Pro Ser Ser Arg Trp Leu Ser Asp Thr Phe Thr Cys
            210                 215                 220

Asn Val Ala His Pro Ser Asn Thr Lys Val Asp Lys Thr Val Arg
225                 230                 235                 240

Lys Thr Asp His Pro Pro Gly Pro Lys Pro Cys Asp Cys Pro Lys Cys
                245                 250                 255

Pro Pro Pro Glu Met Leu Gly Gly Pro Ser Ile Phe Ile Phe Pro Pro
            260                 265                 270

Lys Pro Lys Asp Thr Leu Ser Ile Ser Arg Thr Pro Glu Val Thr Cys
    275                 280                 285

Leu Val Val Asp Leu Gly Pro Asp Asp Ser Asp Val Gln Ile Thr Trp
    290                 295                 300

Phe Val Asp Asn Thr Gln Val Tyr Thr Ala Lys Thr Ser Pro Arg Glu
305                 310                 315                 320

Glu Gln Phe Asn Ser Thr Tyr Arg Val Val Ser Val Leu Pro Ile Leu
                325                 330                 335

His Gln Asp Trp Leu Lys Gly Lys Glu Phe Lys Cys Lys Val Asn Ser
            340                 345                 350

Lys Ser Leu Pro Ser Pro Ile Glu Arg Thr Ile Ser Lys Ala Lys Gly
            355                 360                 365

Gln Pro His Glu Pro Gln Val Tyr Val Leu Pro Pro Ala Gln Glu Glu
        370                 375                 380

Leu Ser Arg Asn Lys Val Ser Val Thr Cys Leu Ile Lys Ser Phe His
385                 390                 395                 400

Pro Pro Asp Ile Ala Val Glu Trp Glu Ile Thr Gly Gln Pro Glu Pro
                405                 410                 415
```

```
Glu Asn Asn Tyr Arg Thr Thr Pro Pro Gln Leu Asp Ser Asp Gly Thr
                420                 425                 430

Tyr Phe Val Tyr Ser Lys Leu Ser Val Asp Arg Ser His Trp Gln Arg
        435                 440                 445

Gly Asn Thr Tyr Thr Cys Ser Val Ser His Glu Ala Leu His Ser His
    450                 455                 460

His Thr Gln Lys Ser Leu Thr Gln Ser Pro Gly Lys
465                 470                 475

<210> SEQ ID NO 25
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Alternative complete feline anti-NGF IgG kappa
      light chain (feN2-kLC)

<400> SEQUENCE: 25

Met Gly Val Pro Thr Gln Leu Leu Gly Leu Leu Leu Trp Ile Thr
1               5                   10                  15

Asp Ala Ile Cys Asp Ile Glu Met Thr Gln Ser Pro Leu Ser Leu Ser
                20                  25                  30

Val Thr Pro Gly Glu Ser Val Ser Ile Ser Cys Arg Ala Ser Glu Asp
        35                  40                  45

Ile Tyr Asn Ala Leu Ala Trp Tyr Leu Gln Lys Pro Gly Arg Ser Pro
    50                  55                  60

Arg Leu Leu Ile Tyr Asn Thr Asp Thr Leu His Thr Gly Val Pro Asp
65                  70                  75                  80

Arg Phe Ser Gly Ser Gly Ser Gly Thr Asp Phe Thr Leu Lys Ile Ser
                85                  90                  95

Arg Val Gln Thr Glu Asp Val Gly Val Tyr Phe Cys Gln His Tyr Phe
            100                 105                 110

His Tyr Pro Arg Thr Phe Gly Gln Gly Thr Lys Leu Glu Leu Lys Arg
        115                 120                 125

Ser Asp Ala Gln Pro Ser Val Phe Leu Phe Gln Pro Ser Leu Asp Glu
    130                 135                 140

Leu His Thr Gly Ser Ala Ser Ile Val Cys Ile Leu Asn Asp Phe Tyr
145                 150                 155                 160

Pro Lys Glu Val Asn Val Lys Trp Lys Val Asp Gly Val Val Gln Thr
                165                 170                 175

Lys Ala Ser Lys Glu Ser Thr Thr Glu Gln Asn Ser Lys Asp Ser Thr
            180                 185                 190

Tyr Ser Leu Ser Ser Thr Leu Thr Met Ser Arg Thr Glu Tyr Gln Ser
        195                 200                 205

His Glu Lys Phe Ser Cys Glu Val Thr His Lys Ser Leu Ala Ser Thr
    210                 215                 220

Leu Val Lys Ser Phe Asn Arg Ser Glu Cys Gln Arg Glu
225                 230                 235

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Alternative light chain FR1 (feN2-kLC)

<400> SEQUENCE: 26

Asp Ile Glu Met Thr Gln Ser Pro Leu Ser Leu Ser Val Thr Pro Gly
1               5                   10                  15

Glu Ser Val Ser Ile Ser Cys
            20

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alternative light chain FR2 (feN2-kLC)

<400> SEQUENCE: 27

Trp Tyr Leu Gln Lys Pro Gly Arg Ser Pro Arg Leu Leu Ile Tyr
1               5                   10                  15

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Alternative light chain FR3 (feN2-kLC)

<400> SEQUENCE: 28

Gly Val Pro Asp Arg Phe Ser Gly Ser Gly Ser Gly Thr Asp Phe Thr
1               5                   10                  15

Leu Lys Ile Ser Arg Val Gln Thr Glu Asp Val Gly Val Tyr Phe Cys
            20                  25                  30

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alternative light chain FR4 (feN2-kLC)

<400> SEQUENCE: 29

Phe Gly Gln Gly Thr Lys Leu Glu Leu Lys
1               5                   10

<210> SEQ ID NO 30
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alternative heavy chain FR1 (feN2-VH)

<400> SEQUENCE: 30

Gln Val Gln Leu Val Glu Ser Gly Ala Glu Leu Val Gln Pro Gly Glu
1               5                   10                  15

Ser Leu Arg Leu Thr Cys Ala Ala Ser Gly
```

20                  25

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alternative heavy chain FR2 (feN2-VH)

<400> SEQUENCE: 31

Trp Val Arg Gln Ala Pro Gly Lys Gly Leu Glu Trp Met Gly
1               5                   10

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Alternative heavy chain FR3 (feN2-VH)

<400> SEQUENCE: 32

Arg Leu Thr Ile Thr Arg Asp Thr Ser Lys Asn Thr Val Phe Leu Gln
1               5                   10                  15

Met His Ser Leu Gln Ser Glu Asp Thr Ala Thr Tyr Tyr Cys Ala Arg
                20                  25                  30

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alternative heavy chain FR4 (feN2-VH)

<400> SEQUENCE: 33

Trp Gly Gln Gly Thr Thr Val Thr Val Ser Ala
1               5                   10

<210> SEQ ID NO 34
<211> LENGTH: 335
<212> TYPE: PRT
<213> ORGANISM: Felis catus

<400> SEQUENCE: 34

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ala Ser Gly Leu Tyr Ser
        50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ile Val Met Thr Gln Thr Pro Leu Ser Leu Ser Val Thr Pro Gly
1               5                   10                  15

Glu Pro Ala Ser Ala Ser Cys
            20

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Val Pro Asp Arg Phe Ser Gly Ser Gly Ser Gly Thr Asp Phe Thr
1               5                   10                  15

Leu Arg Ile Ser Arg Val Glu Ala Asp Asp Val Gly Val Tyr Phe Cys
            20                  25                  30

```
<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Val Pro Asp Arg Phe Ser Gly Ser Gly Ser Gly Thr Asp Phe Thr
1               5                   10                  15

Leu Arg Ile Ser Arg Val Glu Ala Asp Asp Val Gly Val Tyr Tyr Cys
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: G or A
<220> FEATURE:
<221> NAME/KEY: MOD_RES
<222> LOCATION: (10)..(10)
<223> OTHER INFORMATION: D or E
<220> FEATURE:
<221> NAME/KEY: MOD_RES
<222> LOCATION: (15)..(15)
<223> OTHER INFORMATION: G or E
<220> FEATURE:
<221> NAME/KEY: MOD_RES
<222> LOCATION: (16)..(16)
<223> OTHER INFORMATION: G or A
<220> FEATURE:
<221> NAME/KEY: MOD_RES
<222> LOCATION: (19)..(19)
<223> OTHER INFORMATION: R or K
<220> FEATURE:
<221> NAME/KEY: MOD_RES
<222> LOCATION: (23)..(23)
<223> OTHER INFORMATION: A, V or M

<400> SEQUENCE: 38

Gln Val Gln Leu Val Glu Ser Gly Xaa Xaa Leu Val Gln Pro Xaa Xaa
1               5                   10                  15

Ser Leu Xaa Leu Thr Cys Xaa Ala Ser Gly Phe Ser Leu Thr
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: D or H
<220> FEATURE:
<221> NAME/KEY: MOD_RES
<222> LOCATION: (10)..(10)
<223> OTHER INFORMATION: D or E
<220> FEATURE:
<221> NAME/KEY: MOD_RES
<222> LOCATION: (12)..(12)
<223> OTHER INFORMATION: R or S
<220> FEATURE:
```

```
<221> NAME/KEY: MOD_RES
<222> LOCATION: (15)..(15)
<223> OTHER INFORMATION: G or E
<220> FEATURE:
<221> NAME/KEY: MOD_RES
<222> LOCATION: (16)..(16)
<223> OTHER INFORMATION: G or A
<220> FEATURE:
<221> NAME/KEY: MOD_RES
<222> LOCATION: (21)..(21)
<223> OTHER INFORMATION: F or S
<220> FEATURE:
<221> NAME/KEY: MOD_RES
<222> LOCATION: (27)..(27)
<223> OTHER INFORMATION: Y or L
<220> FEATURE:
<221> NAME/KEY: MOD_RES
<222> LOCATION: (28)..(28)
<223> OTHER INFORMATION: T or N
<220> FEATURE:
<221> NAME/KEY: MOD_RES
<222> LOCATION: (29)..(29)
<223> OTHER INFORMATION: F or V
<220> FEATURE:
<221> NAME/KEY: MOD_RES
<222> LOCATION: (30)..(30)
<223> OTHER INFORMATION: S, G or R

<400> SEQUENCE: 39

Xaa Glu Leu Leu Val Gln Ser Gly Arg Xaa Val Xaa Lys Pro Xaa Xaa
1               5                   10                  15

Ser Val Ser Ile Xaa Cys Lys Thr Ser Gly Xaa Xaa Xaa Xaa
            20                  25                  30

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L, W, F or A
<220> FEATURE:
<221> NAME/KEY: MOD_RES
<222> LOCATION: (5)..(5)
<223> OTHER INFORMATION: P or T
<220> FEATURE:
<221> NAME/KEY: MOD_RES
<222> LOCATION: (7)..(7)
<223> OTHER INFORMATION: E or A
<220> FEATURE:
<221> NAME/KEY: MOD_RES
<222> LOCATION: (8)..(8)
<223> OTHER INFORMATION: Q or T
<220> FEATURE:
<221> NAME/KEY: MOD_RES
<222> LOCATION: (12)..(12)
<223> OTHER INFORMATION: E or T
<220> FEATURE:
<221> NAME/KEY: MOD_RES
<222> LOCATION: (13)..(13)
<223> OTHER INFORMATION: V or L
<220> FEATURE:
<221> NAME/KEY: MOD_RES
<222> LOCATION: (14)..(14)
<223> OTHER INFORMATION: A, T or S

<400> SEQUENCE: 40

Trp Xaa Cys Gln Xaa Pro Xaa Xaa Gly Phe Gln Xaa Xaa Xaa
1               5                   10
```

```
<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: L or F
<220> FEATURE:
<221> NAME/KEY: MOD_RES
<222> LOCATION: (5)..(5)
<223> OTHER INFORMATION: S or T
<220> FEATURE:
<221> NAME/KEY: MOD_RES
<222> LOCATION: (8)..(8)
<223> OTHER INFORMATION: T or N
<220> FEATURE:
<221> NAME/KEY: MOD_RES
<222> LOCATION: (9)..(9)
<223> OTHER INFORMATION: A or S
<220> FEATURE:
<221> NAME/KEY: MOD_RES
<222> LOCATION: (11)..(11)
<223> OTHER INFORMATION: N or D
<220> FEATURE:
<221> NAME/KEY: MOD_RES
<222> LOCATION: (13)..(13)
<223> OTHER INFORMATION: L or A
<220> FEATURE:
<221> NAME/KEY: MOD_RES
<222> LOCATION: (21)..(21)
<223> OTHER INFORMATION: K or R
<220> FEATURE:
<221> NAME/KEY: MOD_RES
<222> LOCATION: (22)..(22)
<223> OTHER INFORMATION: S or T

<400> SEQUENCE: 41

Arg Xaa Thr Ile Xaa Arg Asp Xaa Xaa Lys Xaa Thr Xaa Tyr Leu Gln
1               5                   10                  15

Met Asn Ser Leu Xaa Xaa Glu Asp Thr Ala Thr Tyr Tyr Cys Ala Arg
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: L or F
<220> FEATURE:
<221> NAME/KEY: MOD_RES
<222> LOCATION: (4)..(4)
<223> OTHER INFORMATION: L or V
<220> FEATURE:
<221> NAME/KEY: MOD_RES
<222> LOCATION: (5)..(5)
<223> OTHER INFORMATION: S or T
<220> FEATURE:
<221> NAME/KEY: MOD_RES
<222> LOCATION: (6)..(6)
<223> OTHER INFORMATION: A or I
<220> FEATURE:
<221> NAME/KEY: MOD_RES
<222> LOCATION: (9)..(9)
<223> OTHER INFORMATION: G or T
<220> FEATURE:
<221> NAME/KEY: MOD_RES
<222> LOCATION: (10)..(10)
```

```
<223> OTHER INFORMATION: T, R, G or Q
<220> FEATURE:
<221> NAME/KEY: MOD_RES
<222> LOCATION: (11)..(11)
<223> OTHER INFORMATION: N or D
<220> FEATURE:
<221> NAME/KEY: MOD_RES
<222> LOCATION: (13)..(13)
<223> OTHER INFORMATION: L or A
<220> FEATURE:
<221> NAME/KEY: MOD_RES
<222> LOCATION: (14)..(14)
<223> OTHER INFORMATION: D or S
<220> FEATURE:
<221> NAME/KEY: MOD_RES
<222> LOCATION: (16)..(16)
<223> OTHER INFORMATION: E, L or R
<220> FEATURE:
<221> NAME/KEY: MOD_RES
<222> LOCATION: (17)..(17)
<223> OTHER INFORMATION: L or T
<220> FEATURE:
<221> NAME/KEY: MOD_RES
<222> LOCATION: (18)..(18)
<223> OTHER INFORMATION: S, D or T
<220> FEATURE:
<221> NAME/KEY: MOD_RES
<222> LOCATION: (19)..(19)
<223> OTHER INFORMATION: I, N, R or T
<220> FEATURE:
<221> NAME/KEY: MOD_RES
<222> LOCATION: (21)..(21)
<223> OTHER INFORMATION: G or T
<220> FEATURE:
<221> NAME/KEY: MOD_RES
<222> LOCATION: (22)..(22)
<223> OTHER INFORMATION: P or A
<220> FEATURE:
<221> NAME/KEY: MOD_RES
<222> LOCATION: (23)..(23)
<223> OTHER INFORMATION: T, A or D
<220> FEATURE:
<221> NAME/KEY: MOD_RES
<222> LOCATION: (27)..(27)
<223> OTHER INFORMATION: V or M
<220> FEATURE:
<221> NAME/KEY: MOD_RES
<222> LOCATION: (29)..(29)
<223> OTHER INFORMATION: C or F
<220> FEATURE:
<221> NAME/KEY: MOD_RES
<222> LOCATION: (31)..(31)
<223> OTHER INFORMATION: G, I, T, S or V
<220> FEATURE:
<221> NAME/KEY: MOD_RES
<222> LOCATION: (32)..(32)
<223> OTHER INFORMATION: K, S, T, I, V, P, N or G

<400> SEQUENCE: 42

Arg Xaa Ala Xaa Xaa Xaa Asp Ser Xaa Xaa Xaa Ala Xaa Xaa Met Xaa
1               5                   10                  15

Xaa Xaa Xaa Leu Xaa Xaa Xaa Asp Ala Ala Xaa Tyr Xaa Arg Xaa Xaa
            20                  25                  30

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: L or I
```

-continued

<400> SEQUENCE: 43

Trp Gly Gln Gly Thr Xaa Val Thr Val Ser Ser
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: P, V, H or R
<220> FEATURE:
<221> NAME/KEY: MOD_RES
<222> LOCATION: (5)..(5)
<223> OTHER INFORMATION: A, V, I or S
<220> FEATURE:
<221> NAME/KEY: MOD_RES
<222> LOCATION: (11)..(11)
<223> OTHER INFORMATION: Q, A or P

<400> SEQUENCE: 44

Arg Arg Xaa Gly Xaa Gln Val Thr Val Thr Xaa
1               5                   10

<210> SEQ ID NO 45
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E or N
<220> FEATURE:
<221> NAME/KEY: MOD_RES
<222> LOCATION: (2)..(2)
<223> OTHER INFORMATION: V, I, P or T
<220> FEATURE:
<221> NAME/KEY: MOD_RES
<222> LOCATION: (3)..(3)
<223> OTHER INFORMATION: V, E or M
<220> FEATURE:
<221> NAME/KEY: MOD_RES
<222> LOCATION: (4)..(4)
<223> OTHER INFORMATION: M, L or I
<220> FEATURE:
<221> NAME/KEY: MOD_RES
<222> LOCATION: (7)..(7)
<223> OTHER INFORMATION: T or S
<220> FEATURE:
<221> NAME/KEY: MOD_RES
<222> LOCATION: (10)..(10)
<223> OTHER INFORMATION: S or F
<220> FEATURE:
<221> NAME/KEY: MOD_RES
<222> LOCATION: (12)..(12)
<223> OTHER INFORMATION: S, P or A
<220> FEATURE:
<221> NAME/KEY: MOD_RES
<222> LOCATION: (14)..(14)
<223> OTHER INFORMATION: T, I or A
<220> FEATURE:
<221> NAME/KEY: MOD_RES
<222> LOCATION: (17)..(17)
<223> OTHER INFORMATION: E or D
<220> FEATURE:
<221> NAME/KEY: MOD_RES
<222> LOCATION: (18)..(18)
<223> OTHER INFORMATION: P, S or A

```
<220> FEATURE:
<221> NAME/KEY: MOD_RES
<222> LOCATION: (19)..(19)
<223> OTHER INFORMATION: A or V
<220> FEATURE:
<221> NAME/KEY: MOD_RES
<222> LOCATION: (21)..(21)
<223> OTHER INFORMATION: I or F
<220> FEATURE:
<221> NAME/KEY: MOD_RES
<222> LOCATION: (22)..(22)
<223> OTHER INFORMATION: S or F

<400> SEQUENCE: 45

Xaa Xaa Xaa Xaa Thr Gln Xaa Pro Leu Xaa Leu Xaa Val Xaa Pro Gly
1               5                   10                  15

Xaa Xaa Xaa Ser Xaa Xaa Cys
            20

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ile Gln Met Thr Gln Ser Pro Ala Ser Leu Ser Ala Ser Leu Gly
1               5                   10                  15

Glu Thr Val Thr Ile Glu Cys
            20

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Y or F
<220> FEATURE:
<221> NAME/KEY: MOD_RES
<222> LOCATION: (3)..(3)
<223> OTHER INFORMATION: L, F or R
<220> FEATURE:
<221> NAME/KEY: MOD_RES
<222> LOCATION: (5)..(5)
<223> OTHER INFORMATION: K or R
<220> FEATURE:
<221> NAME/KEY: MOD_RES
<222> LOCATION: (8)..(8)
<223> OTHER INFORMATION: Q or R
<220> FEATURE:
<221> NAME/KEY: MOD_RES
<222> LOCATION: (12)..(12)
<223> OTHER INFORMATION: R or L
<220> FEATURE:
<221> NAME/KEY: MOD_RES
<222> LOCATION: (14)..(14)
<223> OTHER INFORMATION: I or M
<220> FEATURE:
<221> NAME/KEY: MOD_RES
<222> LOCATION: (15)..(15)
<223> OTHER INFORMATION: Y, H or A

<400> SEQUENCE: 47

Trp Xaa Xaa Gln Xaa Pro Gly Xaa Ser Pro Arg Xaa Leu Xaa Xaa
1               5                   10                  15
```

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Tyr Gln Gln Lys Pro Gly Lys Ser Pro Gln Leu Leu Ile Tyr
1               5                   10                  15

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: G or R
<220> FEATURE:
<221> NAME/KEY: MOD_RES
<222> LOCATION: (6)..(6)
<223> OTHER INFORMATION: F or I
<220> FEATURE:
<221> NAME/KEY: MOD_RES
<222> LOCATION: (7)..(7)
<223> OTHER INFORMATION: S or T
<220> FEATURE:
<221> NAME/KEY: MOD_RES
<222> LOCATION: (13)..(13)
<223> OTHER INFORMATION: T, A or S
<220> FEATURE:
<221> NAME/KEY: MOD_RES
<222> LOCATION: (16)..(16)
<223> OTHER INFORMATION: T, I or A
<220> FEATURE:
<221> NAME/KEY: MOD_RES
<222> LOCATION: (18)..(18)
<223> OTHER INFORMATION: R, T or K
<220> FEATURE:
<221> NAME/KEY: MOD_RES
<222> LOCATION: (20)..(20)
<223> OTHER INFORMATION: S, A, G or T
<220> FEATURE:
<221> NAME/KEY: MOD_RES
<222> LOCATION: (21)..(21)
<223> OTHER INFORMATION: R or G
<220> FEATURE:
<221> NAME/KEY: MOD_RES
<222> LOCATION: (22)..(22)
<223> OTHER INFORMATION: V or M
<220> FEATURE:
<221> NAME/KEY: MOD_RES
<222> LOCATION: (23)..(23)
<223> OTHER INFORMATION: E or Q
<220> FEATURE:
<221> NAME/KEY: MOD_RES
<222> LOCATION: (24)..(24)
<223> OTHER INFORMATION: A, V, P or T
<220> FEATURE:
<221> NAME/KEY: MOD_RES
<222> LOCATION: (25)..(25)
<223> OTHER INFORMATION: D or E
<220> FEATURE:
<221> NAME/KEY: MOD_RES
<222> LOCATION: (29)..(29)
<223> OTHER INFORMATION: V, I, H or L
<220> FEATURE:
<221> NAME/KEY: MOD_RES
<222> LOCATION: (31)..(31)
<223> OTHER INFORMATION: Y or F

```
<400> SEQUENCE: 49

Xaa Val Pro Asp Arg Xaa Xaa Gly Ser Gly Ser Gly Xaa Asp Phe Xaa
1               5                   10                  15

Leu Xaa Ile Xaa Xaa Xaa Xaa Xaa Xaa Asp Val Gly Xaa Tyr Xaa Cys
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Val Pro Ser Arg Phe Ser Gly Ser Gly Ser Gly Thr Gln Tyr Ser
1               5                   10                  15

Leu Lys Ile Asn Ser Leu Gln Ser Glu Asp Val Ala Ser Tyr Phe Cys
            20                  25                  30

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F or S
<220> FEATURE:
<221> NAME/KEY: MOD_RES
<222> LOCATION: (3)..(3)
<223> OTHER INFORMATION: Q or P
<220> FEATURE:
<221> NAME/KEY: MOD_RES
<222> LOCATION: (6)..(6)
<223> OTHER INFORMATION: K, H, Q, E, S or T
<220> FEATURE:
<221> NAME/KEY: MOD_RES
<222> LOCATION: (8)..(8)
<223> OTHER INFORMATION: E or D
<220> FEATURE:
<221> NAME/KEY: MOD_RES
<222> LOCATION: (9)..(9)
<223> OTHER INFORMATION: I, V, M or L
<220> FEATURE:
<221> NAME/KEY: MOD_RES
<222> LOCATION: (10)..(10)
<223> OTHER INFORMATION: K, R, D or T

<400> SEQUENCE: 51

Xaa Gly Xaa Gly Thr Xaa Leu Xaa Xaa Xaa
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Gly Gly Gly Thr Lys Leu Glu Leu Lys
1               5                   10
```

```
<210> SEQ ID NO 53
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Q, D or H
<220> FEATURE:
<221> NAME/KEY: MOD_RES
<222> LOCATION: (2)..(2)
<223> OTHER INFORMATION: V or E
<220> FEATURE:
<221> NAME/KEY: MOD_RES
<222> LOCATION: (3)..(3)
<223> OTHER INFORMATION: Q or L
<220> FEATURE:
<221> NAME/KEY: MOD_RES
<222> LOCATION: (6)..(6)
<223> OTHER INFORMATION: E or Q
<220> FEATURE:
<221> NAME/KEY: MOD_RES
<222> LOCATION: (9)..(9)
<223> OTHER INFORMATION: G, A or R
<220> FEATURE:
<221> NAME/KEY: MOD_RES
<222> LOCATION: (10)..(10)
<223> OTHER INFORMATION: D or E
<220> FEATURE:
<221> NAME/KEY: MOD_RES
<222> LOCATION: (11)..(11)
<223> OTHER INFORMATION: L or V
<220> FEATURE:
<221> NAME/KEY: MOD_RES
<222> LOCATION: (12)..(12)
<223> OTHER INFORMATION: V, R or S
<220> FEATURE:
<221> NAME/KEY: MOD_RES
<222> LOCATION: (13)..(13)
<223> OTHER INFORMATION: Q or K
<220> FEATURE:
<221> NAME/KEY: MOD_RES
<222> LOCATION: (15)..(15)
<223> OTHER INFORMATION: G or E
<220> FEATURE:
<221> NAME/KEY: MOD_RES
<222> LOCATION: (16)..(16)
<223> OTHER INFORMATION: G or A
<220> FEATURE:
<221> NAME/KEY: MOD_RES
<222> LOCATION: (18)..(18)
<223> OTHER INFORMATION: L or V
<220> FEATURE:
<221> NAME/KEY: MOD_RES
<222> LOCATION: (19)..(19)
<223> OTHER INFORMATION: R, K or S
<220> FEATURE:
<221> NAME/KEY: MOD_RES
<222> LOCATION: (20)..(20)
<223> OTHER INFORMATION: L or I
<220> FEATURE:
<221> NAME/KEY: MOD_RES
<222> LOCATION: (21)..(21)
<223> OTHER INFORMATION: T, F or S
<220> FEATURE:
<221> NAME/KEY: MOD_RES
<222> LOCATION: (23)..(23)
<223> OTHER INFORMATION: A, V, M or K
<220> FEATURE:
<221> NAME/KEY: MOD_RES
<222> LOCATION: (24)..(24)
<223> OTHER INFORMATION: A or T

<400> SEQUENCE: 53

Xaa Xaa Xaa Leu Val Xaa Ser Gly Xaa Xaa Xaa Xaa Xaa Pro Xaa Xaa
```

```
1               5                   10                  15

Ser Xaa Xaa Xaa Xaa Cys Xaa Xaa Ser Gly
            20                  25

<210> SEQ ID NO 54
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Q, D or E
<220> FEATURE:
<221> NAME/KEY: MOD_RES
<222> LOCATION: (2)..(2)
<223> OTHER INFORMATION: V or E
<220> FEATURE:
<221> NAME/KEY: MOD_RES
<222> LOCATION: (3)..(3)
<223> OTHER INFORMATION: L, Q or R
<220> FEATURE:
<221> NAME/KEY: MOD_RES
<222> LOCATION: (4)..(4)
<223> OTHER INFORMATION: L or V
<220> FEATURE:
<221> NAME/KEY: MOD_RES
<222> LOCATION: (5)..(5)
<223> OTHER INFORMATION: V or M
<220> FEATURE:
<221> NAME/KEY: MOD_RES
<222> LOCATION: (6)..(6)
<223> OTHER INFORMATION: Q, E or D
<220> FEATURE:
<221> NAME/KEY: MOD_RES
<222> LOCATION: (9)..(9)
<223> OTHER INFORMATION: A or G
<220> FEATURE:
<221> NAME/KEY: MOD_RES
<222> LOCATION: (10)..(10)
<223> OTHER INFORMATION: E, D or N
<220> FEATURE:
<221> NAME/KEY: MOD_RES
<222> LOCATION: (11)..(11)
<223> OTHER INFORMATION: L, V or R
<220> FEATURE:
<221> NAME/KEY: MOD_RES
<222> LOCATION: (12)..(12)
<223> OTHER INFORMATION: V, R or K
<220> FEATURE:
<221> NAME/KEY: MOD_RES
<222> LOCATION: (13)..(13)
<223> OTHER INFORMATION: K, T, Q, E, N or R
<220> FEATURE:
<221> NAME/KEY: MOD_RES
<222> LOCATION: (14)..(14)
<223> OTHER INFORMATION: P or T
<220> FEATURE:
<221> NAME/KEY: MOD_RES
<222> LOCATION: (15)..(15)
<223> OTHER INFORMATION: G or E
<220> FEATURE:
<221> NAME/KEY: MOD_RES
<222> LOCATION: (16)..(16)
<223> OTHER INFORMATION: G, A, T or E
<220> FEATURE:
<221> NAME/KEY: MOD_RES
<222> LOCATION: (17)..(17)
<223> OTHER INFORMATION: S or A
<220> FEATURE:
<221> NAME/KEY: MOD_RES
<222> LOCATION: (18)..(18)
<223> OTHER INFORMATION: L or V
<220> FEATURE:
<221> NAME/KEY: MOD_RES
```

```
<222> LOCATION: (19)..(19)
<223> OTHER INFORMATION: R, K or E
<220> FEATURE:
<221> NAME/KEY: MOD_RES
<222> LOCATION: (20)..(20)
<223> OTHER INFORMATION: I, L or P
<220> FEATURE:
<221> NAME/KEY: MOD_RES
<222> LOCATION: (21)..(21)
<223> OTHER INFORMATION: F, T or S
<220> FEATURE:
<221> NAME/KEY: MOD_RES
<222> LOCATION: (23)..(23)
<223> OTHER INFORMATION: K, V, A or Q
<220> FEATURE:
<221> NAME/KEY: MOD_RES
<222> LOCATION: (24)..(24)
<223> OTHER INFORMATION: A, T or D
<220> FEATURE:
<221> NAME/KEY: MOD_RES
<222> LOCATION: (26)..(26)
<223> OTHER INFORMATION: G or A

<400> SEQUENCE: 54

Xaa Xaa Xaa Xaa Xaa Xaa Ser Gly Xaa Xaa Xaa Xaa Xaa Xaa Xaa Xaa
1               5                   10                  15

Xaa Xaa Xaa Xaa Xaa Cys Xaa Xaa Ser Xaa
            20                  25

<210> SEQ ID NO 55
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Val Gln Leu Lys Glu Ser Gly Pro Gly Leu Val Gln Pro Ser Gln
1               5                   10                  15

Thr Leu Ser Leu Thr Cys Thr Val Ser Gly
            20                  25

<210> SEQ ID NO 56
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Val Gln Leu Val Glu Ser Gly Gly Asp Leu Val Gln Pro Gly Gly
1               5                   10                  15

Ser Leu Arg Leu Thr Cys Ala Ala Ser Gly
            20                  25

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V, L, W, F or A
<220> FEATURE:
<221> NAME/KEY: MOD_RES
```

-continued

```
<222> LOCATION: (3)..(3)
<223> OTHER INFORMATION: R or C
<220> FEATURE:
<221> NAME/KEY: MOD_RES
<222> LOCATION: (5)..(5)
<223> OTHER INFORMATION: A, P or T
<220> FEATURE:
<221> NAME/KEY: MOD_RES
<222> LOCATION: (7)..(7)
<223> OTHER INFORMATION: G, E or A
<220> FEATURE:
<221> NAME/KEY: MOD_RES
<222> LOCATION: (8)..(8)
<223> OTHER INFORMATION: K, Q or T
<220> FEATURE:
<221> NAME/KEY: MOD_RES
<222> LOCATION: (10)..(10)
<223> OTHER INFORMATION: L or F
<220> FEATURE:
<221> NAME/KEY: MOD_RES
<222> LOCATION: (11)..(11)
<223> OTHER INFORMATION: E or Q
<220> FEATURE:
<221> NAME/KEY: MOD_RES
<222> LOCATION: (12)..(12)
<223> OTHER INFORMATION: W, E or T
<220> FEATURE:
<221> NAME/KEY: MOD_RES
<222> LOCATION: (13)..(13)
<223> OTHER INFORMATION: M, V or L
<220> FEATURE:
<221> NAME/KEY: MOD_RES
<222> LOCATION: (14)..(14)
<223> OTHER INFORMATION: G, A, T or S

<400> SEQUENCE: 57

Trp Xaa Xaa Gln Xaa Pro Xaa Xaa Gly Xaa Xaa Xaa Xaa Xaa
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V, L, F or I
<220> FEATURE:
<221> NAME/KEY: MOD_RES
<222> LOCATION: (3)..(3)
<223> OTHER INFORMATION: R, C or H
<220> FEATURE:
<221> NAME/KEY: MOD_RES
<222> LOCATION: (5)..(5)
<223> OTHER INFORMATION: A, S, V or T
<220> FEATURE:
<221> NAME/KEY: MOD_RES
<222> LOCATION: (7)..(7)
<223> OTHER INFORMATION: G, A, E or S
<220> FEATURE:
<221> NAME/KEY: MOD_RES
<222> LOCATION: (8)..(8)
<223> OTHER INFORMATION: Q, K or E
<220> FEATURE:
<221> NAME/KEY: MOD_RES
<222> LOCATION: (10)..(10)
<223> OTHER INFORMATION: L, F or P
<220> FEATURE:
<221> NAME/KEY: MOD_RES
<222> LOCATION: (11)..(11)
<223> OTHER INFORMATION: E or Q
<220> FEATURE:
<221> NAME/KEY: MOD_RES
<222> LOCATION: (12)..(12)
```

```
<223> OTHER INFORMATION: W, C or L
<220> FEATURE:
<221> NAME/KEY: MOD_RES
<222> LOCATION: (13)..(13)
<223> OTHER INFORMATION: V, M or I
<220> FEATURE:
<221> NAME/KEY: MOD_RES
<222> LOCATION: (14)..(14)
<223> OTHER INFORMATION: G, A or S

<400> SEQUENCE: 58

Trp Xaa Xaa Gln Xaa Pro Xaa Xaa Gly Xaa Xaa Xaa Xaa Xaa
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Val Arg Gln Ala Thr Gly Arg Gly Leu Glu Trp Met Gly
1               5                   10

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: L or F
<220> FEATURE:
<221> NAME/KEY: MOD_RES
<222> LOCATION: (3)..(3)
<223> OTHER INFORMATION: T or A
<220> FEATURE:
<221> NAME/KEY: MOD_RES
<222> LOCATION: (4)..(4)
<223> OTHER INFORMATION: I, L or V
<220> FEATURE:
<221> NAME/KEY: MOD_RES
<222> LOCATION: (5)..(5)
<223> OTHER INFORMATION: S or T
<220> FEATURE:
<221> NAME/KEY: MOD_RES
<222> LOCATION: (6)..(6)
<223> OTHER INFORMATION: R, A or I
<220> FEATURE:
<221> NAME/KEY: MOD_RES
<222> LOCATION: (8)..(8)
<223> OTHER INFORMATION: T, N or S
<220> FEATURE:
<221> NAME/KEY: MOD_RES
<222> LOCATION: (9)..(9)
<223> OTHER INFORMATION: A, S, G or T
<220> FEATURE:
<221> NAME/KEY: MOD_RES
<222> LOCATION: (10)..(10)
<223> OTHER INFORMATION: K, T, R, G or Q
<220> FEATURE:
<221> NAME/KEY: MOD_RES
<222> LOCATION: (11)..(11)
<223> OTHER INFORMATION: N or D
<220> FEATURE:
<221> NAME/KEY: MOD_RES
<222> LOCATION: (12)..(12)
<223> OTHER INFORMATION: T or A
<220> FEATURE:
<221> NAME/KEY: MOD_RES
```

```
<222> LOCATION: (13)..(13)
<223> OTHER INFORMATION: L or A
<220> FEATURE:
<221> NAME/KEY: MOD_RES
<222> LOCATION: (14)..(14)
<223> OTHER INFORMATION: Y, D or S
<220> FEATURE:
<221> NAME/KEY: MOD_RES
<222> LOCATION: (15)..(15)
<223> OTHER INFORMATION: L or M
<220> FEATURE:
<221> NAME/KEY: MOD_RES
<222> LOCATION: (16)..(16)
<223> OTHER INFORMATION: Q, E, L or R
<220> FEATURE:
<221> NAME/KEY: MOD_RES
<222> LOCATION: (17)..(17)
<223> OTHER INFORMATION: M, L or T
<220> FEATURE:
<221> NAME/KEY: MOD_RES
<222> LOCATION: (18)..(18)
<223> OTHER INFORMATION: N, S, D or T
<220> FEATURE:
<221> NAME/KEY: MOD_RES
<222> LOCATION: (19)..(19)
<223> OTHER INFORMATION: S, I, N, R or T
<220> FEATURE:
<221> NAME/KEY: MOD_RES
<222> LOCATION: (21)..(21)
<223> OTHER INFORMATION: K, R, G or T
<220> FEATURE:
<221> NAME/KEY: MOD_RES
<222> LOCATION: (22)..(22)
<223> OTHER INFORMATION: S, T, P or A
<220> FEATURE:
<221> NAME/KEY: MOD_RES
<222> LOCATION: (23)..(23)
<223> OTHER INFORMATION: E, T, A or D
<220> FEATURE:
<221> NAME/KEY: MOD_RES
<222> LOCATION: (25)..(25)
<223> OTHER INFORMATION: T or A
<220> FEATURE:
<221> NAME/KEY: MOD_RES
<222> LOCATION: (27)..(27)
<223> OTHER INFORMATION: T, V or M
<220> FEATURE:
<221> NAME/KEY: MOD_RES
<222> LOCATION: (29)..(29)
<223> OTHER INFORMATION: Y, C or F
<220> FEATURE:
<221> NAME/KEY: MOD_RES
<222> LOCATION: (30)..(30)
<223> OTHER INFORMATION: C or R
<220> FEATURE:
<221> NAME/KEY: MOD_RES
<222> LOCATION: (31)..(31)
<223> OTHER INFORMATION: A, G, I, T, S or V
<220> FEATURE:
<221> NAME/KEY: MOD_RES
<222> LOCATION: (32)..(32)
<223> OTHER INFORMATION: R, K, S, T, I, V, P, N or G

<400> SEQUENCE: 60

Arg Xaa Xaa Xaa Xaa Asp Xaa Xaa Xaa Xaa Xaa Xaa Xaa Xaa Xaa
1               5                   10                  15

Xaa Xaa Xaa Leu Xaa Xaa Xaa Asp Xaa Ala Xaa Tyr Xaa Xaa Xaa Xaa
                20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<220> FEATURE:
<221> NAME/KEY: MOD_RES
<222> LOCATION: (1)..(1)
<223> OTHER INFORMATION: R, Q or K
<220> FEATURE:
<221> NAME/KEY: MOD_RES
<222> LOCATION: (2)..(2)
<223> OTHER INFORMATION: L or F
<220> FEATURE:
<221> NAME/KEY: MOD_RES
<222> LOCATION: (3)..(3)
<223> OTHER INFORMATION: T or I
<220> FEATURE:
<221> NAME/KEY: MOD_RES
<222> LOCATION: (4)..(4)
<223> OTHER INFORMATION: L, I, M or V
<220> FEATURE:
<221> NAME/KEY: MOD_RES
<222> LOCATION: (5)..(5)
<223> OTHER INFORMATION: S or T
<220> FEATURE:
<221> NAME/KEY: MOD_RES
<222> LOCATION: (6)..(6)
<223> OTHER INFORMATION: R, A, T, K, G or V
<220> FEATURE:
<221> NAME/KEY: MOD_RES
<222> LOCATION: (8)..(8)
<223> OTHER INFORMATION: T, N, D, A or S
<220> FEATURE:
<221> NAME/KEY: MOD_RES
<222> LOCATION: (9)..(9)
<223> OTHER INFORMATION: S, A, D or T
<220> FEATURE:
<221> NAME/KEY: MOD_RES
<222> LOCATION: (10)..(10)
<223> OTHER INFORMATION: T, K, E, Q, N or R
<220> FEATURE:
<221> NAME/KEY: MOD_RES
<222> LOCATION: (11)..(11)
<223> OTHER INFORMATION: N, D or K
<220> FEATURE:
<221> NAME/KEY: MOD_RES
<222> LOCATION: (12)..(12)
<223> OTHER INFORMATION: T, I or A
<220> FEATURE:
<221> NAME/KEY: MOD_RES
<222> LOCATION: (13)..(13)
<223> OTHER INFORMATION: A, L, V or G
<220> FEATURE:
<221> NAME/KEY: MOD_RES
<222> LOCATION: (14)..(14)
<223> OTHER INFORMATION: Y, F, A, S, V or W
<220> FEATURE:
<221> NAME/KEY: MOD_RES
<222> LOCATION: (15)..(15)
<223> OTHER INFORMATION: L or M
<220> FEATURE:
<221> NAME/KEY: MOD_RES
<222> LOCATION: (16)..(16)
<223> OTHER INFORMATION: E, Q, D, H or V
<220> FEATURE:
<221> NAME/KEY: MOD_RES
<222> LOCATION: (17)..(17)
<223> OTHER INFORMATION: L or M
<220> FEATURE:
<221> NAME/KEY: MOD_RES
<222> LOCATION: (18)..(18)
<223> OTHER INFORMATION: N, S, T, D, G, R or H
<220> FEATURE:
<221> NAME/KEY: MOD_RES
<222> LOCATION: (19)..(19)
<223> OTHER INFORMATION: S or N
<220> FEATURE:
<221> NAME/KEY: MOD_RES
<222> LOCATION: (21)..(21)
<223> OTHER INFORMATION: R, K, Q or T
<220> FEATURE:
<221> NAME/KEY: MOD_RES
<222> LOCATION: (22)..(22)
```

```
<223> OTHER INFORMATION: S, T, I, A or V
<220> FEATURE:
<221> NAME/KEY: MOD_RES
<222> LOCATION: (23)..(23)
<223> OTHER INFORMATION: E, A, T, D, G or S
<220> FEATURE:
<221> NAME/KEY: MOD_RES
<222> LOCATION: (26)..(26)
<223> OTHER INFORMATION: A, G or S
<220> FEATURE:
<221> NAME/KEY: MOD_RES
<222> LOCATION: (27)..(27)
<223> OTHER INFORMATION: T, V, M, I or A
<220> FEATURE:
<221> NAME/KEY: MOD_RES
<222> LOCATION: (28)..(28)
<223> OTHER INFORMATION: Y or H
<220> FEATURE:
<221> NAME/KEY: MOD_RES
<222> LOCATION: (29)..(29)
<223> OTHER INFORMATION: Y, H or F
<220> FEATURE:
<221> NAME/KEY: MOD_RES
<222> LOCATION: (31)..(31)
<223> OTHER INFORMATION: A, T, V, G, L, I or M

<400> SEQUENCE: 61

Xaa Xaa Xaa Xaa Xaa Xaa Asp Xaa Xaa Xaa Xaa Xaa Xaa Xaa Xaa Xaa
1               5                   10                  15

Xaa Xaa Xaa Leu Xaa Xaa Xaa Asp Thr Xaa Xaa Xaa Xaa Cys Xaa Arg
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Arg Leu Thr Ile Thr Arg Asp Thr Ser Lys Ser Gln Val Phe Leu Lys
1               5                   10                  15

Met His Ser Leu Gln Ser Glu Asp Thr Ala Thr Tyr Tyr Cys Ala Arg
            20                  25                  30

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: W or R
<220> FEATURE:
<221> NAME/KEY: MOD_RES
<222> LOCATION: (2)..(2)
<223> OTHER INFORMATION: G or R
<220> FEATURE:
<221> NAME/KEY: MOD_RES
<222> LOCATION: (3)..(3)
<223> OTHER INFORMATION: Q, P, V, H or R
<220> FEATURE:
<221> NAME/KEY: MOD_RES
<222> LOCATION: (5)..(5)
<223> OTHER INFORMATION: T, A, V, I or S
```

```
<220> FEATURE:
<221> NAME/KEY: MOD_RES
<222> LOCATION: (6)..(6)
<223> OTHER INFORMATION: L, I or Q
<220> FEATURE:
<221> NAME/KEY: MOD_RES
<222> LOCATION: (10)..(10)
<223> OTHER INFORMATION: S or T
<220> FEATURE:
<221> NAME/KEY: MOD_RES
<222> LOCATION: (11)..(11)
<223> OTHER INFORMATION: S, Q or P

<400> SEQUENCE: 63

Xaa Xaa Xaa Gly Xaa Xaa Val Thr Val Xaa Xaa
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: W, R, C or L
<220> FEATURE:
<221> NAME/KEY: MOD_RES
<222> LOCATION: (2)..(2)
<223> OTHER INFORMATION: G or A
<220> FEATURE:
<221> NAME/KEY: MOD_RES
<222> LOCATION: (3)..(3)
<223> OTHER INFORMATION: Q, H, R, P or V
<220> FEATURE:
<221> NAME/KEY: MOD_RES
<222> LOCATION: (4)..(4)
<223> OTHER INFORMATION: G or D
<220> FEATURE:
<221> NAME/KEY: MOD_RES
<222> LOCATION: (5)..(5)
<223> OTHER INFORMATION: A, T or V
<220> FEATURE:
<221> NAME/KEY: MOD_RES
<222> LOCATION: (6)..(6)
<223> OTHER INFORMATION: L, I, Q, M, S or T
<220> FEATURE:
<221> NAME/KEY: MOD_RES
<222> LOCATION: (7)..(7)
<223> OTHER INFORMATION: V or I
<220> FEATURE:
<221> NAME/KEY: MOD_RES
<222> LOCATION: (8)..(8)
<223> OTHER INFORMATION: T, A, I or R
<220> FEATURE:
<221> NAME/KEY: MOD_RES
<222> LOCATION: (9)..(9)
<223> OTHER INFORMATION: V or G
<220> FEATURE:
<221> NAME/KEY: MOD_RES
<222> LOCATION: (10)..(10)
<223> OTHER INFORMATION: S or P
<220> FEATURE:
<221> NAME/KEY: MOD_RES
<222> LOCATION: (11)..(11)
<223> OTHER INFORMATION: S, Q or A

<400> SEQUENCE: 64

Xaa Xaa Xaa Xaa Xaa Xaa Xaa Xaa Xaa Xaa Xaa
1               5                   10
```

ANTI-NERVE GROWTH FACTOR ANTIBODIES AND METHODS OF PREPARING AND USING THE SAME

SEQUENCE LISTING

The instant application contains a Sequence Listing which has been submitted electronically in ASCII format and is hereby incorporated by reference in its entirety. Said ASCII copy, created on Dec. 11, 2015, is named 017227-0229 SL.txt and is 83,734 bytes in size.

FIELD OF THE INVENTION

The present invention relates to antibodies and fragments thereof which act as antagonists of feline nerve growth factor. The invention extends to methods of preparing same and to the therapeutic use of these antibodies and fragments in treating conditions associated with nerve growth factor such as pain, pain related disorders and conditions which result in the occurrence of pain in felines.

BACKGROUND TO THE INVENTION

Nerve growth factor (NGF) is a naturally occurring secreted protein which consists of an alpha, beta and gamma polypeptide chain. NGF is a member of the neurotrophin family and is implicated in a number of different roles. NGF promotes survival and differentiation of sensory and sympathetic neurons and signals via two membrane bound receptors, p75, a low affinity NGF receptor and TrkA, a transmembrane tyrosine kinase and a high affinity NGF receptor. The binding of NGF to TrkA or p75 results in an upregulation of neuropeptides in sensory neurons.

The use of NGF antagonists to treat pain and pain sensitivity in humans has been described (Cattaneo A., Curr. Op. Mol. Ther. 2010 12(1):94-106). For example, International Patent Application No. WO 2006/131951 describes a humanised form of the rat alphaD11 (αD11) monoclonal antibody. The αD11 antibody has binding specificity to mouse NGF, but is also known to bind to human and rat forms of NGF. Humanisation of the αD11 rat derived monoclonal antibody is required prior to administration to humans in order to minimise the production of neutralising antibodies which result from a human anti-mouse antibody (HAMA) response being mounted against rodent derived antibodies. Furthermore, the replacement of mouse constant domains with human constant domains allows downstream effector functions to be selected for.

Pain management in felines is currently provided through administration of analgesic drugs of several classes, including local and general anaesthetics, opioid analgesics, α2 agonists, non-steroidal anti-inflammatory drugs (NSAIDs) and steroids. Each of these needs to be administered frequently and also has limitations in efficacy and safety. There is accordingly a need for an infrequently dosed, long lasting and efficacious form of pain relief for felines suffering from chronic pain, such as those with neuropathic or oncologic pain.

While NGF is expressed in feline tissues, only a partial clone is available of its sequence. This partial mRNA sequence is defined in Genbank Accession number EF065101 (See ncbi.nlm.nih.gov. *Felis catus* nerve growth factor beta-like mRNA). No antagonist to feline NGF has been described, nor has the use of blocking NGF mediated signalling in felines to prevent or alleviate pain. The use in felines of known antibodies which act as anti-NGF antagonists in other species would not be feasible as it cannot be determined with certainty whether an antibody with binding specificity to nerve growth factor expressed in another species would also bind to feline nerve growth factor. Furthermore, there also exists the possibility that neutralising antibodies may be produced against any such administered antibody, as it would be recognised as foreign by the feline immune system. Any production of neutralising antibodies would limit the long term administration of the antibody to felines, this being a particularly important requirement when treating a chronic pain related condition or a cancerous condition. Further still, the administration to a feline of an anti-NGF antibody derived from another species may exhibit cross-reactivity to other target epitopes which may be present in felines, but not present in the species from which the antibody was originally derived. Accordingly, there is a serious need for binding members which act as antagonists of feline NGF and which retain high levels of binding affinity and avidity, while avoiding the production of neutralising antibodies there against, for use in pain management in felines.

SUMMARY OF THE INVENTION

Following extensive efforts, the present inventor has surprisingly produced non-immunogenic chimeric and felinised antibodies and binding fragments derived therefrom which bind specifically to feline NGF. It is demonstrated herein, quite unexpectedly, that the binding of the antibodies and binding fragments of the invention to feline NGF sequesters the biological activity of feline NGF by inhibiting the binding of feline NGF to the high affinity TrkA receptor or to the p75 receptor. This, in turn, prevents the upregulation of neuropeptides in sensory neurons with the resulting effect that the sensation of pain will be reduced or removed. The antibodies have been produced using recombinant DNA methods such that they are substantially non-immunogenic, that is, neutralising antibodies are not raised against them when administered to a feline subject. Such a finding is entirely surprising and unexpected, as the antibodies were not produced using standard methodologies, such as CDR grafting, or the like.

According to a first aspect of the invention there is provided a method of preparing an antibody suitable for use in a feline comprising or consisting essentially of the steps of:

providing a donor antibody from a species other than a feline, wherein the donor antibody has binding specificity for a target antigen present in felines;

comparing each amino acid residue of the amino acid sequence of framework regions of the donor antibody with each amino acid residue present at a corresponding position in the amino acid sequence of framework regions of one or more feline antibodies to identify one or more amino acid residues within the amino acid sequence of the framework regions of the donor antibody that differ from one or more amino acid residues at the corresponding position within the amino acid sequence of framework regions of the one or more feline antibodies; and substituting the one or more identified amino acid residues in the donor antibody with the one or more amino acid residues present at the corresponding position in the one or more feline antibodies.

The method of the present invention modifies a donor antibody for use in a feline in such a way that the modified antibody does not contain any amino acid in any position within the framework regions which would be foreign at that position in felines. The modified antibody therefore retains the specificity and affinity of the donor antibody for the target antigen, but importantly is modified such that no potentially foreign epitopes are created. The modified antibody is therefore not seen as foreign in felines and hence does not induce an immune response in felines which could lead to a neutralisation of the efficacy of the antibody, especially following long term administration.

In certain embodiments, the step of substituting the one or more identified amino acid residues comprises substituting the one or more identified amino acid residues with the one or more amino acid residues present at the corresponding position which have the highest homology to the one or more substituted amino acid residues.

In certain embodiments, the method further comprises the step of replacing constant domains of the heavy chain and/or light chain of the donor antibody with constant domains of a heavy and/or light chain from a feline antibody. Typically, the constant domain of the heavy chain is replaced with a HC2 type feline constant domain.

In certain embodiments, the target epitope is nerve growth factor (NGF).

The method of the first aspect of the invention does not comprise CDR grafting. Antibodies prepared according to the method of the first aspect of the invention comprise CDRs of the donor antibody, felinised framework regions prepared according to the method of the first aspect of the invention and feline constant domains.

According to a second aspect of the present invention there is provided a chimeric antibody or a binding fragment thereof which specifically binds to feline neuronal growth factor (NGF), said chimeric antibody comprising light and/or heavy chain variable domains derived from an antibody which binds nerve growth factor in a species other than felines, and light and heavy chain constant domains obtained from feline derived antibodies. Typically, the chimeric antibody or binding fragment derived therefrom binds to feline NGF at a binding epitope which, when bound, results in neutralisation of the biological function of feline NGF. That is, the binding of the chimeric antibody or binding fragment to feline NGF sequesters the ability of feline NGF to bind to the TrkA receptor or to the p75 receptor. In certain embodiments, the chimeric antibody, or binding fragment thereof, binds to feline NGF with a binding affinity ($K_D$) of $1\times10^{-8}$ or less.

In one embodiment of the present invention, there is provided an anti-feline NGF chimeric antibody or a binding fragment thereof which binds to feline NGF and which neutralises the ability of feline NGF to bind to the p75 or the TrkA feline NGF receptors, the chimeric antibody comprising a light chain comprising the amino acid sequence of SEQ ID NO:1 or an amino acid sequence which has a sequence identity of at least 85, 90, 95 or 99% thereto and/or a heavy chain comprising the amino acid sequence of SEQ ID NO:2 or a sequence which has an amino acid identity of at least 85, 90, 95 or 99% thereto. The heavy chain constant domains of SEQ ID NO:2 are derived from the antibody derived from Felis catus which is deposited under Genbank accession number BAA32229.1 (SEQ ID NO:34). In a further embodiment, the heavy chain has the amino acid sequence of SEQ ID NO:16, that is a constant domain conjoined to heavy chain constant domains derived from the antibody derived from *Felis catus* which is deposited under Genbank accession number BAA32230.1 (SEQ ID NO:34).

Typically, the constant domains of the anti-feline NGF chimeric antibody of the invention do not mediate downstream effector functions associated with the antibody constant regions, such as complement fixation, ADCC, Fc receptor binding, or the like. In certain embodiments, residues of the constant domains of the heavy chain may be substituted to residues which cannot be glycosylated. In certain embodiments, the aglycosylated heavy chain has the amino acid sequence of SEQ ID NO:19 or a sequence which has an amino acid identity of at least 85, 90, 95 or 99% thereto.

The present invention extends to antibodies prepared according to the first aspect of the present invention. Accordingly, in certain further aspects the present invention extends to a felinised anti-feline NGF neutralising antibody. The felinised antibody retains the binding specificity of an antibody which binds to non-feline NGF at a binding epitope which the inventor predicts is conserved between feline NGF and NGF of other species, while reducing the immunogenicity of the antibody by providing feline derived constant domains, and, significantly, modifying selected residues of the variable region framework regions (FRs) in order that the binding specificity of the CDR regions is unaltered, but that the T cell epitopes which may be present in the framework regions interposed between the CDR regions are removed by substitutions of specific residues in the donor antibody framework regions with feline derived amino acids. Importantly, the framework residues are not replaced in their entirety by framework regions derived from antibodies of feline origin. Rather, the substitution of framework residues is considered and specific.

According to a further or related aspect of the invention there is provided a felinised antibody or binding fragment thereof which binds specifically to feline neuronal growth factor (NGF). Typically, the felinised antibody or binding fragment thereof neutralises feline NGF biological function, when bound thereto. That is, the binding of the felinised antibody or binding fragment to feline NGF sequesters the ability of feline NGF to bind to the TrkA NGF receptor or to the p75 NGF receptor. In certain embodiments, the felinised antibody, or binding fragment thereof, binds to NGF with a binding affinity $K_D$ of $1\times10^{-8}$ or less. Typically, the felinised antibody is not immunogenic in felines.

In certain embodiments, the felinised antibody is prepared according to the method of preparing an antibody of the first aspect of the invention.

In a further or related aspect of the invention there is provided a neutralising antibody, or an antigen binding fragment thereof, which is capable of specifically binding to feline nerve growth factor (NGF), the antibody or antibody binding fragment comprising, consisting of or consisting essentially of a light chain variable domain comprising the amino acid sequence of SEQ ID NO:23 or a sequence which has an amino acid identity of at least 85, 90, 95 or 99% thereto. In certain embodiments said identity is over a length of at least about 15 amino acids, preferably about 20 amino acids, more preferably about 25 amino acids.

In some embodiments the neutralising antibody is a monoclonal antibody. In some embodiments, the antibody is a chimeric antibody. In some embodiments, the antibody is a felinised antibody, that is, an antibody which has an amino acid sequence which has been de-immunised such that neutralising antibodies will not be produced there against when administered to a feline subject. In certain embodiments, the felinised antibody is prepared according to the method of preparing an antibody of the first aspect of the invention. Typically the heavy chain constant domains of the antibody are selected or modified by way of amino acid substitution or deletion such that the constant domains do not mediate downstream effector functions.

In certain embodiments, the felinised antibody or antibody binding fragment thereof comprises, consists of, or consists essentially of a light chain comprising the amino acid sequence of SEQ ID NO:25 or an amino acid sequence which has at least 85, 90, 95 or 99% sequence identity thereto. In certain embodiments said identity is over a length of at least about 15 amino acids, preferably about 20 amino acids, more preferably about 25 amino acids.

In a further or related aspect, there is provided a neutralising felinised antibody, or an antigen binding fragment thereof, which is capable of specifically binding to feline nerve growth factor (NGF), the felinised antibody or antibody binding fragment comprising, consisting of or consisting essentially of a heavy chain variable domain comprising the amino acid sequence of SEQ ID NO:22 or an amino acid sequence which has a sequence identity of at least 85, 90, 95 or 99% thereto. In certain embodiments said identity is over a length of at least about 15 amino acids, preferably about 20 amino acids, more preferably about 25 amino acids.

Typically, the variable region of the heavy chain (VH) is conjoined to a heavy chain constant region which comprises at least one immunoglobulin constant domain. Typically, a heavy chain constant region is comprised of 3 tandem (i.e. in line) constant domains, with a hinge region being provided between 2 of the domains to provide structural flexibility. Constant regions of different isotypes may comprise more or less than 3 constant domains. In certain embodiments, the heavy chain constant region is derived from a feline derived antibody. Two different feline constant domains are known (represented by Genbank accession numbers BAA32229.1 and BAA32230.1), with the same hinge region and eight amino acid sequence differences between their CH3 domains. Typically, said constant domains comprise CH1, CH2 and CH3 along with a suitable linker (or "hinge") located between said CH1 and CH2 domains. Typically, the anti-feline NGF antibody of the invention comprises a heavy chain variable domain conjoined to a constant domain, wherein the constant domain does not result in antibody Fc region mediated downstream effector functions such as complement fixation, ADCC, Fc receptor binding, or the like.

In certain embodiments, the antibody or antibody binding fragment comprises, consists of, or consists essentially of a heavy chain comprising the amino acid sequence of: SEQ ID NO:24 or a sequence which has an amino acid identity of at least 85, 90, 95 or 99% thereto.

In particular embodiments, the felinised antibody or binding fragment derived therefrom may comprise a heavy chain wherein at least one residue in a constant domain has been substituted or deleted in order to prevent the glycosylation of that residue. In certain embodiments, the heavy chain subtype is derived from a feline antibody of subtype IgG2. In certain further embodiments, the constant domains are derived from the antibody derived from Felis catus which is deposited under Genbank accession number BAA32230.1.

In a yet further or related aspect, the present invention extends to a felinised antibody, or an antigen binding fragment thereof, which specifically binds to feline nerve growth factor (NGF) and neutralises its biological function in binding to the TrkA NGF receptor and the p75 NGF receptor, the felinised antibody or antibody binding fragment thereof comprising a light chain and a heavy chain, wherein the variable domain of the light chain (VL) comprises, consists or consists essentially of an amino acid sequence which is identical or substantially homologous to the amino acid sequence of SEQ ID NO:23 or a sequence which has an amino acid identity of at least 85, 90, 95 or 99% thereto, and wherein the variable domain of the heavy chain (VH) comprises, consists or consists essentially of an amino acid sequence which is identical or substantially homologous to the amino acid sequence of SEQ ID NO:22 or a sequence which has an amino acid identity of at least 85, 90, 95 or 98% thereto. In certain embodiments said identity is over a length of at least about 15 amino acids, preferably about 20 amino acids, more preferably about 25 amino acids.

In certain embodiments, the felinised antibody or binding member comprises a light chain which comprises, consists of or consists essentially of the amino acid sequence of SEQ ID NO:25 or a sequence having an amino acid identity of at least 85%, more preferably of 95% and most preferably at least 98% identity thereto. In certain embodiments said identity is over a length of at least about 15 amino acids, preferably about 20 amino acids, more preferably about 25 amino acids.

In certain embodiments, the felinised antibody or binding member comprises a heavy chain which comprises, consists of or consists essentially of an amino acid sequence of SEQ ID NO:24 or a polypeptide having an amino acid sequence with an identity of at least 85%, more preferably of 95% and most preferably at least 98% identity thereto. In certain embodiments said identity is over a length of at least about 15 amino acids, preferably about 20 amino acids, more preferably about 25 amino acids.

In certain embodiments, the antibody may be conjugated to at least one reporter molecule. In certain further embodiments at least one residue in at least one of the constant domains can be substituted or deleted in order to prevent the glycosylation of that residue.

In a further or related aspect of the invention there is provided a neutralising antibody, or an antigen binding fragment thereof, which is capable of specifically binding to feline nerve growth factor (NGF), the antibody or antibody binding fragment comprising, consisting of or consisting essentially of a light chain variable domain comprising the amino acid sequence of SEQ ID NO:3 or a sequence which has an amino acid identity of at least 85, 90, 95 or 99% thereto. In certain embodiments said identity is over a length of at least about 15 amino acids, preferably about 20 amino acids, more preferably about 25 amino acids.

In some embodiments the neutralising antibody is a monoclonal antibody. In some embodiments, the antibody is a chimeric antibody. In some embodiments, the antibody is a felinised antibody, that is, an antibody which has an amino acid sequence which has been de-immunised such that neutralising antibodies will not be produced there against when administered to a feline subject. In certain embodiments, the antibody is prepared according to the first aspect of the invention. Typically the heavy chain constant domains of the antibody are selected or modified by way of amino acid substitution or deletion such that the constant domains do not mediate downstream effector functions.

In certain embodiments, the felinised antibody or antibody binding fragment thereof comprises, consists of, or consists essentially of a light chain comprising the amino acid sequence of SEQ ID NO:5 or an amino acid sequence which has at least 85, 90, 95 or 99% sequence identity thereto. In certain embodiments said identity is over a length of at least about 15 amino acids, preferably about 20 amino acids, more preferably about 25 amino acids.

In a further or related aspect, there is provided a neutralising felinised antibody, or an antigen binding fragment thereof, which is capable of specifically binding to feline nerve growth factor (NGF), the felinised antibody or antibody binding fragment comprising, consisting of or consisting essentially of a heavy chain variable domain comprising the amino acid sequence of SEQ ID NO:4 or an amino acid sequence which has a sequence identity of at least 85, 90, 95 or 99% thereto. In certain embodiments said identity is over a length of at least about 15 amino acids, preferably about 20 amino acids, more preferably about 25 amino acids.

Typically, the variable region of the heavy chain (VH) is conjoined to a heavy chain constant region which comprises at least one immunoglobulin constant domain. In certain embodiments, the heavy chain constant region is derived from a feline derived antibody, e.g. those represented by Genbank accession numbers BAA32229.1 and BAA32230.1. Typically, said constant domains comprise CH1, CH2 and CH3 along with a suitable linker (or "hinge") located between said CH1 and CH2 domains. Typically, the anti-feline NGF antibody of the invention comprises a heavy chain variable domain conjoined to a constant domain, wherein the constant domain does not result in antibody Fc region mediated downstream effector functions such as complement fixation, ADCC, Fc receptor binding, or the like.

In certain embodiments, the antibody or antibody binding fragment comprises, consists of, or consists essentially of a heavy chain comprising the amino acid sequence of: SEQ ID NO:6 or a sequence which has an amino acid identity of at least 85, 90, 95 or 99% thereto. In said embodiment, the constant domains are derived from the antibody derived from *Felis catus* which is deposited under Genbank accession number BAA32229.1.

In particular embodiments, the felinised antibody or binding fragment derived therefrom may comprise a heavy chain wherein at least one residue in a constant domain has been substituted or deleted in order to prevent the glycosylation of that residue. Accordingly, in certain further embodiments, the antibody or antibody binding fragment comprises, consists of, or consists essentially of a heavy chain comprising the amino acid of SEQ ID NO:7 or a sequence which has an amino acid identity of at least 85, 90, 95 or 99% thereto. In certain embodiments said identity is over a length of at least about 15 amino acids, preferably about 20 amino acids, more preferably about 25 amino acids. In certain embodiments, the heavy chain subtype is derived from a feline antibody of subtype IgG2.

In certain further embodiments, the constant domains are derived from the antibody derived from *Felis catus* which is deposited under Genbank accession number BAA32230.1. Accordingly, in certain further embodiments, the heavy chain of a further felinised antibody according to the present invention comprises a heavy chain derived from the antibody derived from *Felis catus* which is deposited under Genbank accession number BAA32230.1. Said antibody comprises the amino acid sequence of SEQ ID NO:17. In certain further embodiments, the heavy chain sequence of SEQ ID NO:17 may be modified to substitute any amino acid residues which may be subject to glycosylation. Accordingly, a yet further embodiment of the invention provides a felinised antibody with a heavy chain comprising the amino acid sequence of SEQ ID NO:18 or an amino acid sequence which has a sequence identity of at least 85, 90, 95 or 99% thereto. In certain embodiments said identity is over a length of at least about 15 amino acids, preferably about 20 amino acids, more preferably about 25 amino acids.

In a yet further or related aspect, the present invention extends to a felinised antibody, or an antigen binding fragment thereof, which specifically binds to feline nerve growth factor (NGF) and neutralises its biological function in binding to the TrkA NGF receptor and the p75 NGF receptor, the felinised antibody or antibody binding fragment thereof comprising a light chain and a heavy chain, wherein the variable domain of the light chain (VL) comprises, consists or consists essentially of an amino acid sequence which is identical or substantially homologous to the amino acid sequence of SEQ ID NO:3 or a sequence which has an amino acid identity of at least 85, 90, 95 or 99% thereto, and wherein the variable domain of the heavy chain (VH) comprises, consists or consists essentially of an amino acid sequence which is identical or substantially homologous to the amino acid sequence of SEQ ID NO:4 or a sequence which has an amino acid identity of at least 85, 90, 95 or 98% thereto. In certain embodiments said identity is over a length of at least about 15 amino acids, preferably about 20 amino acids, more preferably about 25 amino acids.

In certain embodiments, the felinised antibody or binding member comprises a light chain which comprises, consists of or consists essentially of the amino acid sequence of SEQ ID NO:5 or a sequence having an amino acid identity of at least 85%, more preferably of 95% and most preferably at least 98% identity thereto. In certain embodiments said identity is over a length of at least about 15 amino acids, preferably about 20 amino acids, more preferably about 25 amino acids.

In certain embodiments, the felinised antibody or binding member comprises a heavy chain which comprises, consists of or consists essentially of an amino acid sequence of SEQ ID NO:6 or SEQ ID NO:17 or a polypeptide having an amino acid sequence with an identity of at least 85%, more preferably of 95% and most preferably at least 98% identity thereto. In certain embodiments said identity is over a length of at least about 15 amino acids, preferably about 20 amino acids, more preferably about 25 amino acids.

In certain embodiments, the antibody may be conjugated to at least one reporter molecule.

In certain further embodiments at least one residue in at least one of the constant domains can be substituted or deleted in order to prevent the glycosylation of that residue. Accordingly, in certain further embodiments, the felinised antibody or antibody binding fragment comprises, consists of, or consists essentially of a heavy chain comprising the amino acid sequence of SEQ ID NO:7 or SEQ ID NO:18 or an amino acid sequence with an identity of at least 95% and more preferably at least 98% identity thereto. In certain embodiments said identity is over a length of at least about 15 amino acids, preferably about 20 amino acids, more preferably about 25 amino acids.

The inventor has further defined a series of framework regions (FR) which can be combined with complementarity determining regions (CDRs) to form felinised heavy and light chain variable domains. Each of the heavy and light chain domains has 4 framework regions, designated FR1, FR2, FR3 and FR4.

An antibody molecule may comprise a heavy chain variable domain comprising CDR1, CDR2 and CDR3 regions and associated interposed framework regions. The heavy chain variable domain (VH) CDRs are known as HCDRs, with these CDRs being found at the following positions according to the Kabat numbering system: HCDR1—Kabat residues 31-35, HCDR2—Kabat residues 50-65, HCDR3—Kabat residues 95-102 (Kabat E A et al. (1991) Sequences of proteins of immunological interest, 5$^{th}$ edition. Bethesda: US Department of Health and Human Services).

Furthermore, an antibody further comprises a light chain variable domain comprising CDR1, CDR2 and CDR3 regions and associated interposed framework regions. The light chain variable domain (VL) CDRs are known as LCDRs, with these CDRs being found at the following positions according to the Kabat numbering system: LCDR1—Kabat residues 24-34, LCDR2—Kabat residues 50-56, LCDR3—Kabat residues 89-97.

A light or heavy chain variable domain comprises four framework regions, FR1, FR2, FR3 and FR4, interposed with CDRs in the following arrangement: FR1-CDR1-FR2-CDR2-FR3-CDR3-FR4.

In a yet further aspect, the present invention extends to an anti-NGF antibody, or an NGF antigen binding fragment thereof, the antibody or antibody binding fragment comprising a light chain variable region comprising at least one of:
- an FR1 framework region consisting or comprising of the amino acid sequence of SEQ ID NO:26,
- an FR2 framework region consisting or comprising of the amino acid sequence of SEQ ID NO:27,
- an FR3 framework region consisting or comprising of the amino acid sequence of SEQ ID NO:28, and
- an FR4 framework region consisting or comprising of the amino acid sequence of SEQ ID NO:29, and/or a heavy chain variable region comprising at least one of:
- an FR1 framework region consisting or comprising of the amino acid sequence of SEQ ID NO:30,
- an FR2 framework region consisting or comprising of the amino acid sequence of SEQ ID NO:31,
- an FR3 framework region consisting or comprising of the amino acid sequence of SEQ ID NO:32, and
- an FR4 framework region consisting or comprising of the amino acid sequence of SEQ ID NO:33.

Typically the light and heavy chain CDRs are derived from an antibody which has binding specificity to NGF, preferably feline NGF.

In certain embodiments, the light chain variable domain comprising said at least one framework region described above is conjoined to a feline derived light chain constant domain, typically a light chain kappa constant domain, but optionally a light chain lambda constant domain. In certain embodiments, said light chain comprises an FR1 region having an amino acid sequence of SEQ ID NO:26, an FR2 region with an amino acid sequence of SEQ ID NO:27, an FR3 region with an amino acid sequence of SEQ ID NO:28 and an FR4 region with an amino acid sequence of SEQ ID NO:29 or a framework region with an amino acid sequence which has a sequence identity of at least 85, 90, 95 or 98% to the foregoing. In certain embodiments said identity is over a length of at least about 5 amino acids, preferably about 10 amino acids.

In certain further embodiments, the heavy chain variable region comprising at least one of the framework regions described above is conjoined to at least one feline derived heavy chain constant domain. In certain embodiments, the amino acid sequence of the constant domain lacks any post-translational modifications, or may be modified to remove any or all residues which may be subject to N-linked or O-linked glycosylation, such that the constant domains are aglycosylated. In certain embodiments the heavy chain comprises an FR1 region with an amino acid sequence of SEQ ID NO:30, an FR2 region with an amino acid sequence of SEQ ID NO:31, an FR3 region with an amino acid sequence of SEQ ID NO:32 and an FR4 region with an amino acid sequence of SEQ ID NO:33 or a framework region with an amino acid sequence which has a sequence identity of at least 85, 90, 95 or 98% to the foregoing. In certain embodiments said identity is over a length of at least about 5 amino acids, preferably about 10 amino acids.

In certain further embodiments, modifications may be made to the framework regions described herein. That is, the inventor has identified that for some residues in each framework region, there is a choice of amino acids for a given position. Importantly, these framework region modifications do not result in a conformational change to the associated complementarity determining regions, as this may alter the binding specificity and/or affinity of the resulting antibody. In certain embodiments, the invention extends to introducing 2 or more amino acid substitutions into the amino acid residues of framework regions of the light chain variable region and/or heavy chain variable region.

Accordingly, in certain embodiments, the invention extends to polypeptides, such as an antibody, or antigen binding fragment thereof, which comprises a light chain variable domain having an FR1 region comprising the amino acid sequence of SEQ ID NO:26 which has been modified by one or more of the amino acid substitutions selected from the group consisting of D1 is E or N, I2 is V, P or T, E3 is V or M, M4 is L or I, S7 is T, S10 is F, S12 is P or A, T14 is I or A, E17 is D, S18 is P or A, V19 is A, I21 is F and S22 is F.

In certain embodiments, the light chain FR2 region having the amino acid sequence of SEQ ID NO:27 may be modified by one or more of the amino acid substitutions selected from the group consisting of Y2 is F, L3 is F or R, K5 is R, R8 is Q, L12 is R, I14 is M and Y15 is H or A.

In certain embodiments, the light chain FR3 region having the amino acid sequence of SEQ ID NO:28 may be modified by one or more of the amino acid substitutions selected from the group consisting of G1 is R, F6 is I, S7 is T, T13 is A or S, T16 is I or A, K18 is R or T, S20 is A, G or T, R21 is G, V22 is M, Q23 is E, T24 is A, V or P, E25 is D, V29 is I, H or L and F31 is Y.

In certain embodiments, the light chain FR4 region having the amino acid sequence of SEQ ID NO:29 may be modified by one or more of the amino acid substitutions selected from the group consisting of F1 is S, Q3 is P, K6 is H, Q, E, S or T, E8 is D, L9 is V, I or M and K10 is R, D or T.

In certain embodiments, the heavy chain FR1 region having the amino acid sequence of SEQ ID NO:30 may be modified by one or more of the amino acid substitutions selected from the group consisting of Q1 is D or E, V2 is E, Q3 is L or R, L4 is V, V5 is M, E6 is Q or D, A9 is G, E10 is D or N, L11 is V or R, V12 is R or K, Q13 is K, T, E, N or P, P14 is T, G15 is E, E16 is G, A or T, S17 is A, L18 is V, R19 is K or E, L20 is I or P, T21 is F or S, A23 is K, V or Q, A24 is T or D and G26 is A.

In certain further embodiments, the heavy chain FR2 region having the amino acid sequence of SEQ ID NO:31 may be modified by one or more of the amino acid substitutions selected from the group consisting of V2 is L, F or I, R3 is C or H, A5 is S, V or T, G7 is A, E or S, K8 is Q or E, L10 is F or P, E11 is Q, W12 is C or L, M13 is V or I and G14 is A or S.

In certain further embodiments, the heavy chain FR3 region having the amino acid sequence of SEQ ID NO:32 may be modified by one or more of the amino acid substitutions selected from the group consisting of R1 is Q or K, L2 is F, T3 is I, I4 is L, M or V, T5 is S, R6 is A, T, K, G or V, T8 is N, D, A or S, S9 is A, D or T, K10 is T, E, Q, N or R, N11 is D or K, T12 is I or A, V13 is A, L or G, F14 is Y, V, A, S or W, L15 is M, Q16 is E, D, H or V, M17 is L, H18 is N, S, T, D, G or R, S19 is N, Q21 is R, K or T, S22 is T, I, A or V, E23 is A, T, D, G or S, A26 is G or S, T27 is V, M, I or A, Y28 is H, Y29 is H or F and A31 is T, V, G, L, I or M.

In certain further embodiments, the heavy chain FR4 region having the amino acid sequence of SEQ ID NO:33 may be modified by one or more of the amino acid substitutions selected from the group consisting of W1 is R, C or L, G2 is A, Q3 is H, R, P or V, G4 is D, T5 is A or V, T6 is L, I, Q, M or S, V7 is I, T8 is A, I or R, V9 is G, S10 is P and A11 is S or Q.

In certain embodiments, the antibody is a monoclonal antibody. Typically the antibody is a felinised antibody.

In a yet further aspect, the present invention extends to an anti-NGF antibody, or an NGF antigen binding fragment thereof, the antibody or antibody binding fragment comprising a light chain variable region comprising at least one of:
- an FR1 framework region consisting of or comprising of the amino acid sequence of SEQ ID NO:8,
- an FR2 framework region consisting of or comprising of the amino acid sequence of SEQ ID NO:9,
- an FR3 framework region consisting of or comprising of the amino acid sequence of SEQ ID NO:10, and
- an FR4 framework region consisting of or comprising of the amino acid sequence of SEQ ID NO:11, and/or a heavy chain variable region comprising at least one of:
- an FR1 framework region consisting of or comprising of the amino acid sequence of SEQ ID NO:12,
- an FR2 framework region consisting of or comprising of the amino acid sequence of SEQ ID NO:13,
- an FR3 framework region consisting of or comprising of the amino acid sequence of SEQ ID NO:14, and
- an FR4 framework region consisting of or comprising of the amino acid sequence of SEQ ID NO:15.

Typically the light and heavy chain CDRs are derived from an antibody which has binding specificity to NGF, preferably feline NGF.

Typically, the production of the felinised anti-feline NGF antibodies of the invention does not require back mutations to be introduced into the framework regions of the light or heavy chain variable domains.

In certain embodiments, the light chain variable domain comprising said at least one framework region described above is conjoined to a feline derived light chain constant domain, typically a light chain kappa constant domain, but optionally a light chain lambda constant domain. In certain embodiments, said light chain comprises an FR1 region having an amino acid sequence of SEQ ID NO:8, an FR2 region with an amino acid sequence of SEQ ID NO:9, an FR3 region with an amino acid sequence of SEQ ID NO:10 and an FR4 region with an amino acid sequence of SEQ ID NO:11 or a framework region with an amino acid sequence which has a sequence identity of at least 85, 90, 95 or 98% to the foregoing. In certain embodiments said identity is over a length of at least about 5 amino acids, preferably about 10 amino acids.

In certain further embodiments, the heavy chain variable region comprising at least one of the framework regions described above is conjoined to at least one feline derived heavy chain constant domain. In certain embodiments, the amino acid sequence of the constant domain lacks any post-translational modifications, or may be modified to remove any or all residues which may be subject to N-linked or O-linked glycosylation, such that the constant domains are aglycosylated. In certain embodiments the heavy chain comprises an FR1 region with an amino acid sequence of SEQ ID NO:12, an FR2 region with an amino acid sequence of SEQ ID NO:13, an FR3 region with an amino acid sequence of SEQ ID NO:14 and an FR4 region with an amino acid sequence of SEQ ID NO:15 or a framework region with an amino acid sequence which has a sequence identity of at least 85, 90, 95 or 98% to the foregoing. In certain embodiments said identity is over a length of at least about 5 amino acids, preferably about 10 amino acids.

In certain further embodiments, modifications may be made to the framework regions described herein. That is, the inventor has identified that for some residues in each framework region, there is a choice of amino acids for a given position. Importantly, these framework region modifications do not result in a conformational change to the associated complementarity determining regions, as this may alter the binding specificity and/or affinity of the resulting antibody. In certain embodiments, the invention extends to introducing 2 or more amino acid substitutions into the amino acid residues of framework regions of the light chain variable region and/or heavy chain variable region.

Accordingly, in certain further embodiments, the invention extends to polypeptides, such as an antibody, or antigen binding fragment thereof, which comprises a light chain variable domain having an FR1 region comprising the amino acid sequence of SEQ ID NO:8 which has been modified by substituting the amino acid residue I at position 21 (I21) with the amino acid residue A.

In certain further embodiments, the light chain FR3 region having the amino acid sequence of SEQ ID NO:10 may be modified by substituting the amino acid residue F at position 31 (F31) with the amino acid residue Y.

In certain further embodiments, the heavy chain FR1 region having the amino acid sequence of SEQ ID NO:12 may be modified by one or more of the following amino acid substitutions (where the amino acids are denoted by their single letter code): G9 can be A, D10 can be E, G15 can be E, G16 can be A, R19 can be K, A23 can be V or M. Furthermore, Q1 can be D or H, V2 can be E, Q3 can be L, E6 can be Q, G9 can be R, L11 can be V, V12 can be R or S, Q13 can be K, L18 can be V, R19 can be S, L20 can be I, T21 can be F or S, A23 can be K, A24 can be T, F27 can be Y or L, S28 can be T or N, L29 can be F or V and T30 can be S, G or R.

In certain further embodiments, the heavy chain FR2 region having the amino acid sequence of SEQ ID NO:13 may be modified by one or more of the following amino acid substitutions: V2 is L, W, F or A, R3 is C, A5 is P or T, G7 is E or A, K8 is Q or T, L10 is F, E11 is Q, W12 is E or T, M13 is V or L and G14 is A, T or S.

In certain further embodiments, the heavy chain FR3 region having the amino acid sequence of SEQ ID NO:14 may be modified by one or more of the following amino acid substitutions: F2 is L, S5 is T, N8 is T, A9 is S, N11 is D, L13 is A, K21 is R and T22 is S. Furthermore, T3 is A, 14 is L or V, R6 is A or I, N8 is S, A9 is G or T, K10 is T, R, G or Q, T12 is A, Y14 is D or S, L15 is M, Q16 is E, L or R, M17 is L or T, N18 is S, D or T, S19 is I, N, R or T, K21 is G or T, T22 is P or A, E23 is T, A or D, T25 is A, T27 is V or M, Y29 is C or F, C30 is R, A31 is G, I, T, S or V and R32 is K, S, T, I, V, P, N or G.

In certain further embodiments, the heavy chain FR4 region having the amino acid sequence of SEQ ID NO:15 may be modified by one or more of the following amino acid substitutions: L6 is I. Furthermore, W1 can be R, G2 can be R, Q3 can be P, V, H or R, T5 can be A, V, I or S, L6 can be Q, S10 can be T and S11 can be Q, A or P.

In certain embodiments of the above aspects of the invention, the antibody is a monoclonal antibody. Typically the antibody is a felinised antibody.

In certain further embodiments of the above aspects of the invention, the felinised NGF neutralising antibody of the invention, or the binding fragment derived therefrom specifically binds to feline NGF (nerve growth factor) with a binding affinity having an equilibrium dissociation constant ($K_D$) of $1\times10^{-8}$ or less. Furthermore, it is preferred that the felinised antibodies of the invention are not cross-reactive to any other binding epitopes present in felines (other than NGF), and further that neutralising antibodies are not generated against the antibodies of the invention when they are administered to a feline. Furthermore, it is preferred that the constant domains of the antibodies do not mediate any downstream effector functions including, but not limited to: complement fixation and activation, ADCC and Fc receptor binding and activation.

In certain further embodiments, modifications to the amino acid sequence of the constant regions of the heavy chain may be made to the antibodies of the invention. Said modification may involve the addition, substitution or deletion of one or more amino acid residues. Said amino acid changes are typically performed in order to modify the functional characteristics of the antibody. For example, amino acid modification may be performed to prevent downstream effector functions mediated by the antibody constant domains, for example by preventing the ability of the antibody to bind to Fc receptors, activate complement or induce ADCC. Furthermore, modifications may be made to the hinge region of the heavy chain constant domain in order to modify the circulatory half life of an antibody when it is administered to a feline.

In certain embodiments, the antibody, or antigen binding fragment thereof, does not mediate downstream effector functions. Typically the antibody or binding fragment has a feline heavy chain subtype HC2.

In certain embodiments, the felinised antibody is prepared according to the method of preparing an antibody of the first aspect of the invention.

The present invention extends to antibody fragments which bind to feline NGF and sequester its ability to bind to the p75 or TrkA receptors.

In certain embodiments the antibody binding fragment may comprise a heavy chain and light chain sequence of the invention connected by a flexible linker to form a single chain antibody.

A single chain Fv (scFv) comprises a VH and VL domain. The VH and VL domains associate to form a target binding site. These 2 domains are covalently linked by a peptide linker. An scFv molecule can have the form of VL-linker-VH, in cases where the light chain variable domain is required at the N-terminal, or as VH-linker-VL in cases where the VH domain is required at the N-terminal. Accordingly, in certain further embodiments, the antigen binding fragment is a single chain Fv (scFv) antibody fragment. In certain further embodiments, the antibody binding fragment is selected from the group consisting of, but not limited to, a Fab antibody fragment, a Fab' antibody fragment, a F(ab')$_2$ antibody fragment, an Fv antibody fragment and a scFV antibody fragment, and the like.

In certain further embodiments, the invention provides multispecific or multivalent antibodies comprising an anti-feline NGF antibody or binding fragment derived therefrom according to the invention coupled or conjoined to further antibodies with different binding specificities, for use in combination therapy. A multispecific antibody comprises at least one felinised or chimeric antibody or a binding fragment derived therefrom which binds specifically to a first feline NGF epitope, and at least one binding site specific to another epitope present on feline NGF, or to a different antigen. A multivalent antibody comprises antibodies or antibody binding fragments which have binding specificity to the same feline NGF epitope. Accordingly, in certain embodiments, the invention extends to an antibody fusion protein comprising four or more Fv regions or Fab regions of the felinised or chimeric antibodies of the present invention. A yet further embodiment extends to an antibody fusion protein comprising one or more Fab region derived from an antibody of the present invention along with one or more Fab or Fv regions from antibodies specific for feline NGF. In certain further embodiments, the invention extends to a bispecific antibody, wherein an antibody or binding fragment thereof according to the present invention is linked to a secondary antibody or fragment thereof which has binding specific for a secondary target, said target not being feline NGF. Preferably said secondary target assists in preventing NGF mediated signalling through the p75 or TrkA receptors. Such multivalent, bispecific or multispecific antibodies can be made by a variety or recombinant methods which would be well known to the person skilled in the art.

A yet further aspect of the invention provides a felinised anti-neurotrophin neutralising antibody comprising:
(i) a light chain variable domain having the amino acid sequence of SEQ ID NO:3 or SEQ ID NO:23 or a sequence which has at least 85% identity thereto and/or a heavy chain variable domain having the amino acid sequence of SEQ ID NO:4 or SEQ ID NO:22 or a sequence which has at least 85% identity thereto, or
(ii) a chimeric antibody having a light chain having the amino acid sequence of SEQ ID NO:1 and/or a heavy chain having the amino acid sequence of SEQ ID NO:2.

In certain embodiments, the felinised antibody has a light chain having the amino acid sequence of SEQ ID NO:5 or SEQ ID NO:25 and/or a heavy chain having the amino acid sequence of SEQ ID NO:6 or SEQ ID NO:24. In certain embodiments, the neurotrophin is feline nerve growth factor (NGF).

A yet further aspect of the invention provides a method for treating, inhibiting or ameliorating pain in a feline, the method comprising the steps of:
providing a therapeutically effective amount of an anti-feline NGF antibody, or antigen binding fragment thereof, wherein the antibody is a felinised or chimeric antibody according to the present invention, or a binding fragment of the same, and
administering the same to a feline in need thereof.

In certain embodiments, the felinised antibody comprises a light chain variable domain comprising the amino acid sequence of SEQ ID NO:3 or SEQ ID NO:23 or a sequence which has at least 85% identity thereto and/or a heavy chain variable domain comprising the amino acid sequence of SEQ ID NO:4 or SEQ ID NO:22 or an amino acid sequence having at least 85% sequence homology thereto. In certain further embodiments, the felinised antibody comprises a light chain having the amino acid sequence of SEQ ID NO:5 or SEQ ID NO 25 or a sequence having a sequence identity of at least 85% thereto and/or a heavy chain which comprises, consists of or consists essentially of an amino acid of SEQ ID NO:6 or SEQ ID NO 24 or a sequence having an amino acid identity of at least 85% and more preferably at least 98% identity thereto.

In certain embodiments, the felinised antibody or antigen binding fragment thereof is any of those provided by the foregoing aspects of the invention.

In certain embodiments, the chimeric antibody comprises a light chain having the amino acid sequence of SEQ ID NO:1 and/or a heavy chain having the amino acid sequence of SEQ ID NO:2.

In certain embodiments, the pain is neuropathic pain. In particular, the pain may be post-operative or post-surgical pain. Post-operative pain may result following any operating procedure which in felines may include, but is not limited to, orthopaedic surgery, soft tissue surgery, ovariohysterectomy procedures, castration procedures and the like. In certain further embodiments, the pain is chronic pain associated with cancer or a cancerous condition (oncologic pain). In certain further embodiments, the pain is associated with, or resulting from, arthritis, including immune mediated polyarthritis, inflammation, pruritis, rheumatoid arthritis or osteoarthritis.

According to a yet further aspect of the present invention there is provided a method for the treatment of arthritis in a feline subject, said method comprising the steps of:

providing a therapeutically effective amount of an anti-feline NGF antibody according to the invention or antigen binding fragment thereof, and administering the same to a feline in need thereof.

In one embodiment, the anti-feline NGF antibody is a chimeric antibody, wherein the light chain has the amino acid of SEQ ID NO:1 and/or the heavy chain has the amino acid sequence of SEQ ID NO:2.

In certain embodiments, the antibody is a felinised antibody. In certain embodiments, the felinised antibody comprises a light chain variable domain comprising the amino acid sequence of SEQ ID NO:3 or SEQ ID NO 23 or a sequence which has at least 85% identity thereto and/or a heavy chain variable domain comprising the amino acid sequence of SEQ ID NO:4 or SEQ ID NO 22 or an amino acid sequence having at least 85% sequence homology thereto.

In certain embodiments, arthritis includes the conditions selected from the group consisting of immune mediated polyarthritis, rheumatoid arthritis, osteoarthritis and related conditions.

Typically, the treatment of arthritis comprises ameliorating, inhibiting, reducing, suppressing or delaying the onset of pain associated with, or attributable to the arthritic condition.

A further aspect of the present invention provides a method for the treatment of a condition caused by, associated with or resulting in increased expression of feline NGF or increased sensitivity to NGF in a feline subject, said method comprising the steps of:

providing a therapeutically effective amount of an anti-feline NGF antibody according to the invention or antigen binding fragment thereof, and administering the same to a feline in need thereof.

According to a yet further aspect of the present invention there is provided a method for the treatment of a tumour induced to proliferate by NGF in a feline and conditions associated therewith, said method comprising the steps of:

providing a therapeutically effective amount of an anti-feline NGF antibody according to the invention or antigen binding fragment thereof, and administering the same to a feline in need thereof.

In certain embodiments, the tumour is an osteosarcoma. In certain embodiments, the tumour is induced to proliferate by autocrine or paracrine NGF.

In certain embodiments, the foregoing methods of the invention further comprise the step of co-administering at least one further agent which may enhance and/or complement the therapeutic effect of the anti-NGF antibody of the invention. For example, the antibody or antigen binding fragment thereof may be co-administered along with at least one analgesic, NSAID, opioid, corticosteroid or steroid.

Examples of suitable analgesics include, but are not limited to, butorphanol, buprenorphine, fentanyl, flunixin meglumine, merpidine, morphine, nalbuphine and derivatives thereof. Suitable NSAIDS include, but are not limited to, acetaminophen, acetylsalicylic acid, carprofen, etodolac, ketoprofen, meloxicam, firocoxib, robenacoxib, deracoxib and the like.

In certain further embodiments, the at least one further agent may be a therapeutically active agent which may be one or more of the group selected from antibiotic, antifungal, antiprotozoal, antiviral or similar therapeutic agents. Furthermore the at least one further agent may be an inhibitor of mediator(s) of inflammation such as a PGE-receptor antagonist, an immunosuppressive agent, such as cyclosporine, or an anti-inflammatory glucocorticoid. In certain further aspects the at least one further agent may be an agent which is used for the treatment of cognitive dysfunction or impairment, such as memory loss or related conditions which may become increasingly prevalent in older felines. Further still, the at least one further agent may be an anti-hypertensive or other compound used for the treatment of cardiovascular dysfunction, for example to treat hypertension, myocardial ischemia, congestive heart failure and the like. Further still, the at least one further agent may be selected from the group consisting of a diuretic, vasodilator, beta-adrenergic receptor antagonist, angiotensin-II converting enzyme inhibitor, calcium channel blocker and HMG-CoA reductase inhibitor.

In certain embodiments, the antibody or antigen binding fragment of the invention is administered to the feline in need thereof as part of the foregoing methods at a dose ranging from about 0.01 mg/kg of body weight to about 10 mg/kg of body weight, in particular from 0.03 mg/kg of body weight to about 3 mg/kg of body weight.

In various further aspects, the present invention extends to a composition comprising an antibody or binding fragment thereof according to any foregoing aspect of the invention. In certain embodiments, the composition further comprises at least one pharmaceutically acceptable carrier.

A yet further aspect of the invention provides a pharmaceutical composition for treating pain, or a condition resulting in or caused by chronic pain in a feline, comprising a pharmaceutically effective amount of an anti-feline NGF felinised antibody according to the present invention, along with at least one pharmaceutically acceptable carrier, excipient or diluent.

In certain embodiments, the composition further comprises at least one analgesic, NSAID, opioid, corticosteroid or steroid.

In various further aspects, the present invention extends to an isolated nucleic acid which encodes the antibody or antibody binding fragments of the invention.

Accordingly, a yet further aspect of the invention provides an isolated nucleic acid that encodes an antibody or antigen binding fragment according to any of the foregoing aspects of the invention.

In certain embodiments, the polynucleotide encodes a light chain variable domain of an anti-feline NGF felinised antibody or antibody fragment having the amino acid sequence of SEQ ID NO:3 or SEQ ID NO:23, or a complete light chain having the amino acid sequence of SEQ ID NO:5 or SEQ ID NO; 25. In certain further embodiments the polynucleotide encodes a heavy chain variable domain of an anti-feline NGF felinised antibody or antibody fragment having the amino acid sequence of SEQ ID NO:4 or SEQ ID NO;22 or a heavy chain having the amino acid sequence of SEQ ID NO:6, SEQ ID NO:7, SEQ ID NO:17, SEQ ID NO:18 or SEQ ID NO:24.

In certain embodiments, the isolated nucleic acid further encodes one or more regulatory sequences operably linked thereto.

In a further aspect there is provided an expression vector comprising a polynucleotide encoding a heavy and/or light chain variable domain or a heavy and/or light chain constant domain of the invention. In certain embodiments the expression vector further comprises one or more regulatory sequences. In certain embodiments the vector is a plasmid or a retroviral vector.

A yet further aspect provides a host cell incorporating the expression vector of the foregoing aspect of the invention. A further aspect of the invention provides a host cell which produces the antibody of any of the foregoing aspects of the invention.

A yet further aspect of the invention provides a method for producing a felinised anti-feline NGF neutralising antibody, the method comprising the step of culturing the host cell of the foregoing aspect of the invention to allow the cell to express the felinised anti-feline NGF neutralising antibody.

A yet further aspect of the present invention provides a method of producing an anti-feline NGF felinised antibody according to the invention comprising the steps of expressing one or more of the polynucleotides/nucleic acids or vectors of the foregoing aspects of the invention which express the light and/or heavy chains of the antibodies of the invention in a suitable host cell, recovering the expressed polypeptides, which may be expressed together in a host cell, or separately in different host cells, and isolating the antibodies.

A yet further aspect of the invention provides a method for treating, ameliorating or inhibiting pain in a feline, the method comprising the step of administering to the feline an effective amount of a polynucleotide according to any of the foregoing aspects of the invention.

A yet further aspect of the invention provides an antibody or antibody binding fragment according to any of the foregoing aspects of the invention, or a pharmaceutical composition according to the foregoing aspects of the invention, or a nucleic acid, or vector comprising the same according to any of the foregoing aspects of the invention for use in the treatment, amelioration or prevention of pain in a feline.

In certain embodiments the pain is acute pain. In certain embodiments, the pain is chronic pain. Furthermore, the pain may be post-operative pain, or pain resulting from any operating procedure which in felines may include, but is not limited to, orthopaedic surgery, soft tissue surgery, ovariohysterectomy procedures, castration procedures and the like. In certain further embodiments, the pain is chronic pain associated with cancer or a cancerous condition. In certain further embodiments, the pain is associated with, or results from, arthritis or an arthritic condition which includes polyarthritis, inflammation, pruritis, rheumatoid arthritis and osteoarthritis.

A yet further aspect of the invention provides an antibody or antibody binding fragment according to any of the foregoing aspects of the invention, or a pharmaceutical composition according to the foregoing aspects of the invention, or a nucleic acid or vector comprising the same according to any of the foregoing aspects of the invention for use in the treatment or osteoarthritis and/or rheumatoid arthritis.

A yet further aspect of the invention provides an antibody or antibody binding fragment according to any of the foregoing aspects of the invention, or a pharmaceutical composition according to the foregoing aspects of the invention, or a nucleic acid or vector comprising the same according to any of the foregoing aspects of the invention for use in the treatment of a tumour induced to proliferate by NGF in a feline subject and conditions associated therewith, in particular osteosarcoma. In certain embodiments, the tumour is induced to proliferate by autocrine or paracrine NGF.

A yet further aspect of the invention provides use of an antibody or antibody binding fragment according to any of the foregoing aspects of the invention, or a pharmaceutical composition according to the foregoing aspects of the invention, or a nucleic acid or vector comprising the same according to any of the foregoing aspects of the invention in the preparation of a medicament for the treatment or prevention of pain in a feline.

In certain embodiments, the pain is acute pain. In further embodiments the pain is chronic pain. Furthermore, the pain may be post-operative pain, or pain resulting from any operating procedure which in felines may include, but is not limited to, orthopaedic surgery, soft tissue surgery, ovariohysterectomy procedures, castration procedures and the like. In certain further embodiments, the pain is chronic pain associated with cancer or a cancerous condition. In certain further embodiments, the pain is associated with, or results from, inflammation, pruritis, rheumatoid arthritis or osteoarthritis.

A yet further aspect of the invention provides use of an antibody or antibody binding fragment according to any of the foregoing aspects of the invention, or a pharmaceutical composition according to the foregoing aspects of the invention, or a nucleic acid or vector comprising the same according to any of the foregoing aspects of the invention in the preparation of a medicament for the treatment, inhibition amelioration or prevention of rheumatoid arthritis or osteoarthritis in a feline.

A yet further aspect of the invention provides use of an antibody or antibody binding fragment according to any of the foregoing aspects of the invention, or a pharmaceutical composition according to the foregoing aspects of the invention, or a nucleic acid or vector comprising the same according to any of the foregoing aspects of the invention in the preparation of a medicament for the treatment of a tumour induced to proliferate by NGF in a feline and conditions associated therewith, in particular osteosarcoma. In certain embodiments, the tumour is induced to proliferate by autocrine or paracrine NGF.

In a yet further aspect there is provided a cell line, or a derivative or progeny cell thereof that produces anti-feline NGF neutralising monoclonal antibodies, or fragments thereof according to the invention. The antibodies may be felinised or chimeric antibodies.

A yet further aspect of the present invention provides a kit for the treatment of pain in felines, or for the treatment of a condition associated with pain, or for the treatment, amelioration or inhibition of pain associated osteoarthritis, rheumatoid arthritis or polyarthritis comprising an anti-feline NGF antibody or binding fragment according to any of the foregoing aspects of the invention and instructions for use of the same.

A yet further aspect of the present invention provides a diagnostic kit for the detection of an anti-feline NGF monoclonal antibody in fluids in vitro, ex vivo and in vivo, for use in determining the concentration of said antibody. The kit may comprise any of the antibodies of the invention or a binding fragment thereof. The kit may comprise instructions for use of same.

BRIEF DESCRIPTION OF THE FIGURES

FIG. 4A shows that the felinised antibody can be purified using protein A. FIG. 4B shows a gel with banding indicating both heavy and light chains of the felinised antibody.

FIG. 7 shows the amino acid sequence of the light chain of the chimeric feline-rat antibody of the invention, including a leader sequence and a double stop codon at the end of the sequence (SEQ ID NO:20). The rat derived variable domain residues are shown in bold.

FIG. 8 shows the amino acid sequence of the heavy chain of the chimeric feline-rat antibody of the invention, including a leader sequence and a double stop codon at the end of the sequence (SEQ ID NO:21). The rat derived variable domain residues are shown in bold.

FIG. 9 shows the amino acid residues of the light chain variable domain (SEQ ID NO:3) of a felinised antibody of the invention. The residues comprising the 3 CDR residues (CDR1, CDR2 and CDR3) are underlined. Asterisks indicate differences in a residue with the equivalent residue in the rat alphaD11 anti-mouse NGF antibody. The residue numbering is according to Kabat.

FIG. 10 shows the amino acid residues of the heavy chain variable domain (SEQ ID NO:4) of a felinised antibody of the invention. The residues comprising the 3 CDR residues (CDR1, CDR2 and CDR3) are underlined. Asterisks indicate differences in a residue with the equivalent residue in the rat alphaD11 anti-mouse NGF antibody. The residue numbering is according to Kabat.

FIG. 11 shows the amino acid sequence of the light chain of the felinised antibody of the invention (SEQ ID NO:5) wherein the residues in bold are the amino acid residues of the variable domain and the subsequent residues are a light chain kappa constant domain.

FIG. 12 shows the amino acid sequence of the heavy chain of a felinised antibody of the invention (SEQ ID NO:6) wherein the residues in bold are the amino acid residues of the variable domain and the subsequent residues are the residues of the constant domains.

FIG. 13 shows the amino acid sequence of a heavy chain of an alternative felinised antibody of the invention (SEQ ID NO:22—feN2-VH).

FIG. 14 shows the amino acid sequence of a light chain of an alternative felinised antibody of the invention having a light chain kappa constant domain (SEQ ID NO:23—feN2-Vk).

FIG. 15 shows the amino acid sequence of a complete heavy chain of an alternative felinised antibody of the invention (SEQ ID NO:24—feN2-HC2).

FIG. 16 shows the amino acid sequence of a light chain of an alternative felinised antibody of the invention having a light chain kappa constant domain (SEQ ID NO:25—feN2-lLC).

DETAILED DESCRIPTION OF THE INVENTION

Figure 1:
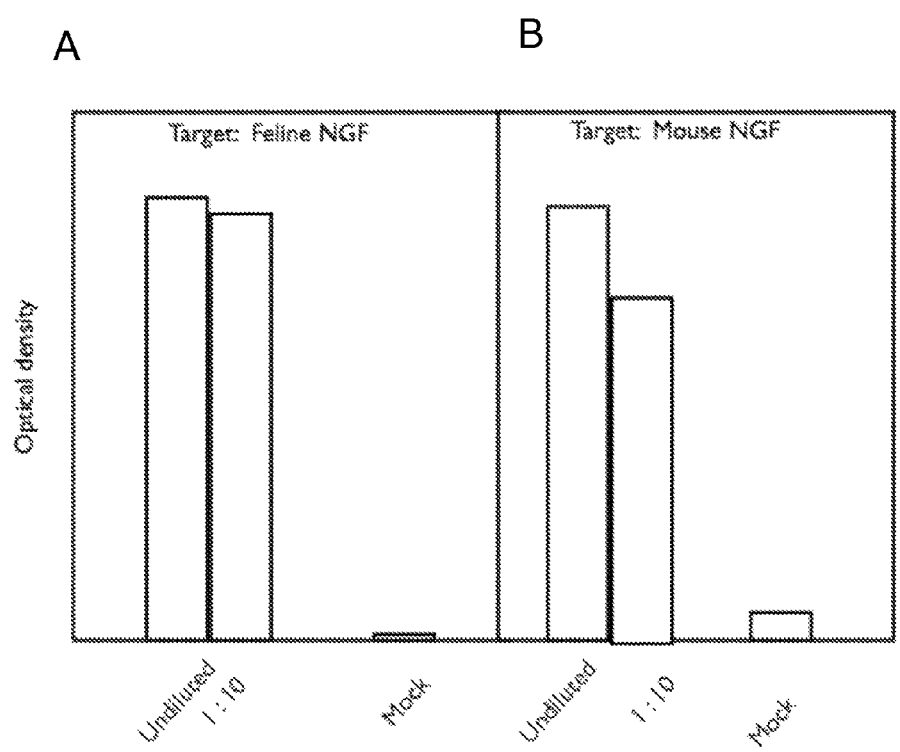
FIG. 1A is a graph showing the binding of chimeric feline-rat antibody to feline NGF.
FIG. 1B shows a graph indicating binding of the chimeric feline-rat antibody to murine NGF.

Following extensive experimentation, the inventor has taken the rat anti-mouse NGF monoclonal antibody (MAb) αD11 amino acid sequence and used this to produce non-immunogenic chimeric and felinised anti-NGF antibodies. The chimeric antibody comprises the heavy and light chain variable domains derived from the alphaD11 rat anti-mouse NGF antibody conjoined to feline antibody derived heavy and light chain constant domains. Even more surprisingly, the felinised antibody, which is not produced using standard CDR grafting techniques, is shown to exhibit high affinity binding to feline NGF. Surprisingly, both the chimeric and felinised antibodies neutralise feline NGF biological function, most specifically by inhibiting the binding of feline NGF to cell based NGF receptors TrkA and p75. Furthermore, it has also been discovered, unexpectedly, that when administered to a feline, neutralising antibodies are not produced there against. Accordingly, both the felinised and chimeric antibodies of the invention are suitable for long term chronic pain relief in cats.

The process of generating the heavy and light chain variable domains for the antibodies of the invention which has been employed by the inventor results in the replacement of specific rat (donor) amino acid residues which are present within the framework regions of the light and heavy chain variable domains with residues which, based on the inventor's analysis, will retain the conformation of the CDR regions and therefore maintain binding specificity and avidity, while reducing the presence of immunogenic epitopes which may result in neutralising antibodies being generated against the antibody, if it were to be administered to felines in an unaltered form. Specifically, the method of preparing antibodies of the invention (known as PETisation) comprises assessing the sequence of the framework regions of a donor (e.g. rat) antibody for suitability for administering to a feline by comparing the sequence of the framework regions of the donor antibody with the sequence of an antibody or a pool of antibodies derived from felines. Although the comparison may be between the donor sequence and a single member of the target sequence, it will be obvious that comparison with a pool of target sequences is preferred because this will expand the number of natural options at each Kabat position in the target species. Not only will this increase the chance of a "match" between the donor and the target, but it will also expand the options for replacement where a match does not exist. As a result, a replacement with characteristics as close as possible to the donor will be able to be chosen. Where the donor sequence and the feline sequence differ at any Kabat number or corresponding position, the donor sequence is modified to substitute the amino acid residue in question with an amino acid residue which is known to be natural at that position in felines.

Where substitution of an amino acid residue present in a donor immunoglobulin framework region is required, typically this is undertaken using the principle of conservative substitution wherein an amino acid residue is replaced with an amino acid residue which is natural at that Kabat position in a feline and is as closely related as possible in size, charge and hydrophobicity to the amino acid being substituted in the donor sequence. The intention is to choose a replacement which would cause no, or at least only minimum, perturbation or disruption to the three-dimensional structure of the donor antibody. In certain situations, there will be no clear option and each choice will have benefits and downsides. A final decision may require three-dimensional modelling or even expression of various alternative sequences. However, generally, a clear preference will be available. As a result of this procedure, a change in the donor sequence is only made when that residue would be foreign in the target and the replacement amino acid is as closely related as possible to that which it replaces. Thus, the creation of foreign epitopes is avoided, but the overall three-dimensional structure is preserved and as a result, affinity and specificity are also preserved.

The light and heavy chain constant regions are derived from feline (target) derived antibodies. The heavy chain constant domains are selected or modified such that they do not mediate downstream effector functions. As it has been found, quite surprisingly, that no or minimal neutralising antibodies are produced against the antibodies produced according to the invention, the antibodies have surprisingly been found to have the associated benefit of long circulatory half life and the option for repeat dosing. Furthermore, as the substitution of the framework residues is performed in such a manner that it does not affect the three dimensional conformation of the CDR regions, there will be no variation in binding specificity.

There are four major IgG isotypes in man and mouse and while nomenclature is similar they differ in behaviour and function including affinity for bacterial products such as Protein A and Protein G, their ability to activate the complement dependent cytolysis (CDC) and their ability to induce killing of target cells through antibody dependent cellular cytotoxity (ADCC). The selection of IgG isotypes with CDC and ADCC active or "armed" constant domains is considered to be of clinical benefit when antibodies are designed to eliminate target cells bearing their cognate antigen, such as in oncology or infection control (e.g. in human medical use human IgG1 isotypes are preferred for the above purposes). By contrast, the activation of the immune system is considered undesirable in other settings such as in the relief of inflammation, pain or autoimmunity and so human IgG isotypes with minimal CDC and ADCC activity are preferred (e.g. in such human medical use, IgG4 isotypes are often preferred). The selection of IgG isotypes with CDC and ADCC active constant domains is considered to be of benefit when antibodies are designed to eliminate target cells bearing the cognate antigen, such as in oncology or infection control, e.g. in human medical use human IgG1 isotypes are preferred. By contrast, the activation of the immune system is considered undesirable in other settings such as in the relief of inflammation, pain or autoimmunity and so human IgG isotypes with minimal or "disarmed" CDC and ADCC activity are preferred, e.g. in human medical use, IgG4 isotypes would be selected. While it is not known whether feline MAb isotypes will have a similar or different spectrum of activities, the selection of armed or disarmed heavy chains is presumed to be of similar value.

Both the felinised and chimeric antibodies of the invention comprise feline derived heavy and light chain constant domains. Furthermore, in both the felinised and chimeric antibodies, the complementarity determining regions (CDRs) are derived from the rat alphaD11 anti-mouse NGF antibody. The αD11 antibody was first described by Cattaneo et al. (Cattaneo A, Rapposelli B, Calissano P. (1988) "Three distinct types of monoclonal antibodies after long-term immunization of rats with mouse nerve growth factor". J Neurochem 50(4):1003-1010). The alphaD11 antibody was subsequently cloned by Ruberti et al. (Ruberti, F. et al. (1993) "Cloning and Expression of an Anti-Nerve Growth Factor (NGF) Antibody for Studies Using the Neuroantibody Approach". Cellular and Molecular Neurobiology. 13(5):559-568).

In the chimeric antibodies of the invention, the heavy and light chain variable domains are the complete variable domains derived from the αD11 antibody.

In the felinised antibodies of the invention, the CDR regions derived from the αD11 antibody are combined with framework region sequences which, although based on the framework regions present in the αD11 antibody, have been modified by way of substituting specific amino acid residues. This process results in the removal of epitopes which may be targeted by T cells following the administration of the antibody to a feline. Furthermore, the framework residue modifications are selected in such a way that the tertiary structure of the CDR regions is preserved, while preventing neutralising antibodies being raised there against, when the antibody is administered to a feline.

Each of the light and heavy chain variable regions contains four framework regions, referred to as FR1-FR4. For each of these framework regions, the inventor has identified a preferred amino residue (a so called preferred residue) for each specific position, and furthermore alternative amino acid residues which could also be provided at that position. Tables 1 to 8 below illustrate the 4 framework regions for each of the heavy and light chains. The tables provide the amino acid position relative to that specific framework region and further according to the Kabat numbering system used to identify the position of a particular residue along the length of the complete heavy or light chain variable domain. The residue or residues shown as group 1 residues are the preferred residues, while the group 2 residues are alternative residues. However these would generally not be preferable to the residues shown in group 1 relating to that specific position. The amino acid residues are identified using the single letter system.

TABLE 1

Light chain variable domain FR1 residues

| Light chain FR1 position | Kabat light chain numbering position | Group 1 amino acid residues (SEQ ID NO: 35) | Group 2 amino acid residues (SEQ ID NO: 8) |
|---|---|---|---|
| 1 | 1 | D | |
| 2 | 2 | I | |
| 3 | 3 | V | |
| 4 | 4 | M | |
| 5 | 5 | T | |
| 6 | 6 | Q | |
| 7 | 7 | T | |
| 8 | 8 | P | |
| 9 | 9 | L | |
| 10 | 10 | S | |
| 11 | 11 | L | |
| 12 | 12 | S | |
| 13 | 13 | V | |
| 14 | 14 | T | |
| 15 | 15 | P | |
| 16 | 16 | G | |
| 17 | 17 | E | |
| 18 | 18 | P | |
| 19 | 19 | A | |
| 20 | 20 | S | |
| 21 | 21 | A | I |
| 22 | 22 | S | |
| 23 | 23 | C | |

TABLE 2

Light chain variable domain FR2 residues

| Light chain FR2 position | Kabat light chain numbering position | Group 1 amino acid residues (SEQ ID NO: 9) | Group 2 amino acid residues (SEQ ID NO: 9) |
|---|---|---|---|
| 1 | 35 | W | |
| 2 | 36 | Y | |
| 3 | 37 | L | |
| 4 | 38 | Q | |
| 5 | 39 | K | |
| 6 | 40 | P | |
| 7 | 41 | G | |
| 8 | 42 | Q | |
| 9 | 43 | S | |
| 10 | 44 | P | |
| 11 | 45 | R | |
| 12 | 46 | R | |
| 13 | 47 | L | |
| 14 | 48 | I | |
| 15 | 49 | Y | |

TABLE 3

Light chain variable domain FR3 residues

| Light chain FR3 position | Kabat light chain numbering position | Group 1 amino acid residues (SEQ ID NO: 36) | Group 2 amino acid residues (SEQ ID NO: 37) |
|---|---|---|---|
| 1 | 57 | G | |
| 2 | 58 | V | |
| 3 | 59 | P | |
| 4 | 60 | D | |
| 5 | 61 | R | |
| 6 | 62 | F | |
| 7 | 63 | S | |
| 8 | 64 | G | |
| 9 | 65 | S | |
| 10 | 66 | G | |
| 11 | 67 | S | |
| 12 | 68 | G | |
| 13 | 69 | T | |
| 14 | 70 | D | |
| 15 | 71 | F | |
| 16 | 72 | T | |
| 17 | 73 | L | |
| 18 | 74 | R | |
| 19 | 75 | I | |
| 20 | 76 | S | |
| 21 | 77 | R | |
| 22 | 78 | V | |
| 23 | 79 | E | |
| 24 | 80 | A | |
| 25 | 81 | D | |
| 26 | 82 | D | |
| 27 | 82A | V | |
| 28 | 82B | G | |
| 29 | 82C | V | |
| 30 | 83 | Y | |
| 31 | 84 | F | Y |
| 32 | 85 | C | |

TABLE 4

Light chain variable domain FR4 residues

| Light chain FR4 position | Kabat light chain numbering position | Group 1 amino acid residues (SEQ ID NO: 11) | Group 2 amino acid residues (SEQ ID NO: 11) |
|---|---|---|---|
| 1 | 95 | F | |
| 2 | 96 | G | |
| 3 | 97 | P | |
| 4 | 98 | G | |
| 5 | 99 | T | |
| 6 | 100 | K | |
| 7 | 101 | L | |
| 8 | 102 | E | |
| 9 | 103 | I | |
| 10 | 104 | K | |

TABLE 5

Heavy chain variable domain FR1 residues

| Heavy chain FR1 position | Kabat heavy chain numbering position | Group 1 amino acid residues (SEQ ID NO: 38) | Group 2 amino acid residues (SEQ ID NO: 39) |
|---|---|---|---|
| 1 | 1 | Q | D, H |
| 2 | 2 | V | E |
| 3 | 3 | Q | L |
| 4 | 4 | L | |
| 5 | 5 | V | |
| 6 | 6 | E | Q |
| 7 | 7 | S | |
| 8 | 8 | G | |
| 9 | 9 | G, A | R |
| 10 | 10 | D, E | |
| 11 | 11 | L | V |
| 12 | 12 | V | R, S |
| 13 | 13 | Q | K |
| 14 | 14 | P | |
| 15 | 15 | G, E | |
| 16 | 16 | G, A | |
| 17 | 17 | S | |
| 18 | 18 | L | V |
| 19 | 19 | R, K | S |
| 20 | 20 | L | I |
| 21 | 21 | T | F, S |
| 22 | 22 | C | |
| 23 | 23 | A, V, M | K |
| 24 | 24 | A | T |
| 25 | 25 | S | |
| 26 | 26 | G | |
| 27 | 27 | F | Y, L |
| 28 | 28 | S | T, N |
| 29 | 29 | L | F, V |
| 30 | 30 | T | S, G, R |

TABLE 6

Heavy chain variable domain FR2 residues

| Heavy Chain FR2 position | Kabat heavy chain numbering position | Group 1 amino acid residues (SEQ ID NO: 13) | Group 2 amino acid residues (SEQ ID NO: 40) |
|---|---|---|---|
| 1 | 36 | W | |
| 2 | 37 | V | L, W, F, A |
| 3 | 38 | R | C |
| 4 | 39 | Q | |
| 5 | 40 | A | P, T |
| 6 | 41 | P | |
| 7 | 42 | G | E, A |
| 8 | 43 | K | Q, T |
| 9 | 44 | G | |
| 10 | 45 | L | F |
| 11 | 46 | E | Q |
| 12 | 47 | W | E, T |
| 13 | 48 | M | V, L |
| 14 | 49 | G | A, T, S |

TABLE 7

Heavy chain variable domain FR3 residues

| Heavy chain FR3 position | Kabat heavy chain numbering position | Group 1 amino acid residues (SEQ ID NO: 41) | Group 2 amino acid residues (SEQ ID NO: 42) |
|---|---|---|---|
| 1 | 66 | R | |
| 2 | 67 | L, F | |
| 3 | 68 | T | A |
| 4 | 69 | I | L, V |
| 5 | 70 | S, T | |
| 6 | 71 | R | A, I |
| 7 | 72 | D | |
| 8 | 73 | T, N | S |
| 9 | 74 | A, S | G, T |
| 10 | 75 | K | T, R, G, Q |
| 11 | 76 | N, D | |
| 12 | 77 | T | A |
| 13 | 78 | L, A | |
| 14 | 79 | Y | D, S |
| 15 | 80 | L | M |
| 16 | 81 | Q | E, L, R |

TABLE 7-continued

Heavy chain variable domain FR3 residues

| Heavy chain FR3 position | Kabat heavy chain numbering position | Group 1 amino acid residues (SEQ ID NO: 41) | Group 2 amino acid residues (SEQ ID NO: 42) |
|---|---|---|---|
| 17 | 82  | M | L, T |
| 18 | 82A | N | S, D, T |
| 19 | 82B | S | I, N, R, T |
| 20 | 82C | L |  |
| 21 | 83  | K, R | G, T |
| 22 | 84  | S, T | P, A |
| 23 | 85  | E | T, A, D |
| 24 | 86  | D |  |
| 25 | 87  | T | A |
| 26 | 88  | A |  |
| 27 | 89  | T | V, M |
| 28 | 90  | Y |  |
| 29 | 91  | Y | C, F |
| 30 | 92  | C | R |
| 31 | 93  | A | G, I, T, S, V |
| 32 | 94  | R | K, S, T, I, V, P, N, G |

TABLE 8

Heavy chain variable domain FR4 residues

| Heavy Chain FR4 position | Kabat heavy chain numbering position | Group 1 amino acid residues (SEQ ID NO: 43) | Group 2 amino acid residues (SEQ ID NO: 44) |
|---|---|---|---|
| 1  | 103 | W | R |
| 2  | 104 | G | R |
| 3  | 105 | Q | P, V, H, R |
| 4  | 106 | G |  |
| 5  | 107 | T | A, V, I, S |
| 6  | 108 | L, I | Q |
| 7  | 109 | V |  |
| 8  | 110 | T |  |
| 9  | 111 | V |  |
| 10 | 112 | S | T |
| 11 | 113 | S | Q, A, P |

The felinised antibody of the invention therefore differs from the chimeric monoclonal antibody of the invention which comprises a complete variable domain derived from a first species (rat alphaD11 anti-mouse NGF antibody) and constant domains derived from a second species (feline derived antibodies), or from a CDR-grafted felinised antibody, where the complementarity determining regions (CDRs) of the heavy and light chain variable regions comprise amino acid residues derived from a donor antibody and introduced into framework regions (FR) and constant regions (CR) derived from a target antibody or from feline germline sequences.

It is preferred that the felinised antibody substantially retains the binding properties of the parent (donor) antibody from which the CDRs are derived. That means that the felinised antibody will exhibit the same or substantially the same antigen-binding affinity and avidity as the donor antibody from which the CDRs are derived, in this instance, the rat derived alphaD11 anti-mouse NGF antibody. Ideally, the affinity of the felinised antibody will not be less than 10% of the donor antibody affinity for the target epitope, more preferably not less than about 30%, and most preferably the affinity will not be less than 50% of the parent antibody. Methods for assaying antigen-binding affinity are well known in the art and include half-maximal binding assays, competition assays, and Scatchard analysis.

As defined hereinbefore, the present invention extends to binding members or antigen binding fragments derived from the chimeric or felinised antibodies of the invention. Such antigen binding fragments refer to one or more fragments of an antibody that retain the ability to specifically bind to feline NGF. It has been shown that the antigen binding function of an antibody can be performed by fragments of a full length antibody. In certain embodiments, the binding members or antigen binding fragments may be isolated binding members. A binding member or antigen binding fragment of the invention may comprise a fragment of the antibodies of the present invention, e.g. a fragment of a fully felinised antibody molecule, such as the heavy or light chain only, or, for example, the variable domain of the heavy and/or light chain. In certain embodiments, a binding member may typically comprise, consist, or consist essentially of an antibody VH and/or VL domain. VH domains of binding members are also provided as part of the invention. Within each of the VH and VL domains are 3 complementarity determining regions ("CDRs"), along with 4 associated framework regions ("FRs"). A VH domain typically comprises 3 HCDRs (heavy chain complementarity determining regions), and a VL domain typically comprises 3 LCDRs (light chain complementarity regions). Accordingly, a binding member may comprise a VH domain comprising, in sequence, VH CDR1 (or HCDR1), CDR2 (HCDR2) and CDR3 (HCDR3) regions along with a plurality of associated framework regions. A binding member may additionally or alternatively comprise a VL domain comprising VL CDR1, CDR2 and CDR3 domains along with associated framework regions. The VH or VL domains typically comprise four framework regions, FR1, FR2, FR3 and FR4, interposed with the 3 complementarity determining regions in the following arrangement: FR1-CDR1-FR2-CDR2-FR3-CDR3-FR4.

FIG. 9 shows the amino acid sequence of a light chain variable domain of an anti-NGF antibody according to the invention. The CDR1, CDR2 and CDR3 regions are underlined. Further, FIG. 10 shows the amino acid sequence of a heavy chain variable domain of an anti-NGF antibody according to the invention. The CDR1, CDR2 and CDR3 regions are underlined.

In FIGS. 9 and 10, the residues of the light chain variable domain (FIG. 9) and heavy chain variable domain (FIG. 10) are conventionally numbered according to the numbering system devised by Kabat et al. (Kabat, E. A., Wu, T. T., Perry, H., Gottesman, K. and Foeller, C. (1991) Sequences of Proteins of Immunological Interest, Fifth Edition. NIH Publication No. 91-3242). The Kabat numbering system is generally used when referring to a residue in the variable domain (approximately residues 1-104 of the light chain and residues 1-113 of the heavy chain). This numbering system is used in the present specification, where stated. The Kabat amino acid residue designations do not always correspond directly with the linear sequential numbering of the amino acid residues of the heavy and light chain variable regions of the present invention provided in the sequence listed in the corresponding SEQ ID NO for that sequence. In particular, the actual linear amino acid sequence may contain fewer or additional amino acids than in the strict Kabat numbering corresponding to a shortening of, or an insertion into, a structural component, whether a framework region or complementarity determining region (CDR), of the basic variable domain structure of the heavy or light chain. The correct Kabat numbering of residues may be determined for any given antibody by alignment of residues in the sequence of the antibody with a standard sequence to which the Kabat numbering has been applied.

FIG. 10 shows a heavy chain variable domain amino acid sequence of a felinised anti-feline NGF antibody of the invention. This is also shown in SEQ ID NO:4. However, in FIG. 10, the numbering used (Kabat) takes account of amino acid residues 80, 80A, 80B, and 80C, whereas in SEQ ID NO:4, the numbering continues sequentially, that is residues 80, 81, 82 and 83. The same is true for Kabat residues 100, 100A, 100B, 100C, 100D, 100E and 100F in FIG. 10.

As described hereinbefore, an antibody binding fragment may be selected from the group comprising, but not limited to, a Fab fragment, a Fab' fragment and a scFv (single chain variable fragment), or from a peptidomimetic, a diabody, or a related multivalent derivative.

In certain embodiments the antibody binding fragment is a Fab or F(ab')2 fragment, which consists of the VL, VH, CL and CH1 domains of an antibody. In certain embodiments, the VL domain has an amino acid sequence of SEQ ID NO:3, and the VH domain has an amino acid sequence of SEQ ID NO:4. In certain embodiments, the CL and CH1 domains are based on the amino acid sequence of a CL and CH1 domain of a feline immunoglobulin.

Techniques used for the recombinant production of Fab, Fab' and F(ab')2 fragments are well known to the person skilled in the art and include those disclosed in International PCT Patent Publication WO 92/22324, and in Sawai et al., "Direct Production of the Fab Fragment Derived From the Sperm Immobilizing Antibody Using Polymerase Chain Reaction and cDNA Expression Vectors", 1995, AJRI 34:26-34. Examples of techniques which can be used to produce scFv (single chain Fv fragments) are disclosed in Huston et al., "Protein Engineering of Single-Chain Fv Analogs and Fusion Proteins", Methods in Enzymology, vol. 203:46-88 (1991), the contents of which are incorporated by reference.

In certain embodiments, antibody fragments can be derived from full length antibodies by proteolytic digestion according to the method of Morimoto (Morimoto et al., "Single-step purification of F(ab')2 fragments of mouse monoclonal antibodies (immunoglobulins G1) by hydrophobic interaction high performance liquid chromatography using TSKgel Phenyl-5PW" Journal of Biochemical and Biophysical Methods 24:107-117 (1992)). Antibody fragments can also be produced directly by host cells (Carter et al., "High level *Escherichia coli* expression and production of a bivalent humanized antibody fragment" Bio/Technology 10:163-167 (1992)).

In addition to providing chimeric and felinised monoclonal antibodies which have binding specificity to feline NGF and which antagonise feline NGF function, the present invention further extends to binding members other than antibodies, comprising a pair of binding domains based on the amino acid sequence of a VL (light chain variable) region as defined in SEQ ID NO:3 and an amino acid sequence of a VH (heavy chain variable) region as defined in SEQ ID NO:4. In particular, the invention extends to single binding domains which are based on either the VL or VH region of the felinised antibodies of the antibodies of the invention.

Accordingly, in certain further embodiments of the present invention, there is provided a binding member comprising, consisting of or consisting essentially of a single binding domain derived from the felinised antibody of the invention. In certain embodiments, the single binding domain is derived from the amino acid sequence of the VH (heavy chain variable domain) as defined in SEQ ID NO:4. Such a binding domain may be used as a targeting agent to feline NGF.

In certain embodiments, further engineering techniques can be used to modify the antibodies of the present invention, for example by including modifications of the Fc region which can alter serum half life, complement fixation, Fc receptor binding and/or antigen dependent cellular cytotoxicity. Further, in certain embodiments, antibodies or antibody fragments can be produced which have altered glycosylation patterns. In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The inventor has provided the amino acid sequence of an aglycosylated feline heavy chain constant region, this being defined in SEQ ID NO:7.

In certain further embodiments, the chimeric and felinised anti-feline NGF antibodies of the invention can be PEGylated by reacting the antibody with a plyethylene glycol (PEG) derivative. In certain embodiments, the felinised or chimeric antibody is defucosylated and therefore lacks fucose residues.

In certain embodiments, modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (A. L. Lehninger, in Biochemistry, $2^{nd}$ Ed., 73-75, Worth Publishers, New York (1975)): (1) non-polar residues: Ala (A), Val (V), Leu (L), Ile (I), Pro (P), Phe (F), Trp (W), Met (M); (2) uncharged polar residues: Gly (G), Ser (S), Thr (T), Cys (C), Tyr (Y), Asn (N), Gln (O); (3) acidic residues: Asp (D), Glu (E); (4) basic: Lys (K), Arg (R), His (H). Alternatively, naturally occurring residues may be divided into groups based on common side-chain properties: (1) hydrophobic residues: Norleucine, Met, Ala, Val, Leu, Ile; (2) neutral hydrophilic residues: Cys, Ser, Thr, Asn, Gln; (3) acidic: Asp, Glu; (4) basic residues: His, Lys, Arg; (5) residues that influence chain orientation: Gly, Pro; (6) aromatic residues: Trp, Tyr, Phe. Non-conservative substitutions will entail exchanging a member of one of these classes for a residue derived from another class. Such substituted residues may be introduced into the conservative substitution sites or, into the remaining (e.g. non-conserved) sites.

In various further aspects, the present invention extends to an immunoconjugate comprising an anti-feline NGF antibody of the invention, or an antigen binding portion thereof linked to a partner molecule. In certain embodiments, such an antibody-partner molecule conjugate is conjugated by means of a chemical linker, such as a peptidyl linker, a hydrazine linker or a disulphide linker. In certain embodiments, the coupling partner is an effector molecule, label, drug, or carrier molecule. Suitable techniques for coupling the antibodies of the invention to both peptidyl and non-peptidyl coupling partners will be well known to persons skilled in the art. Examples of suitable labels include detectable labels, such as a radiolabel, or an enzymatic label, such as horse radish peroxidase, or chemical moieties, such as biotin. Alternatively, the label may be a functional label, for example, ricin, or pro-drugs which are capable of converting prodrugs into active drugs at the site of antibody binding.

In various further aspects, the present invention extends to polynucleotides, and in particular isolated polynucleotides, which encode the chimeric and felinised antibodies of the invention or to the antibody fragments and binding members of the present invention. As defined herein, a "polynucleotide" includes any polyribonucleotide or polydeoxyribonucleotide, which may be unmodified RNA or DNA, or modified RNA or DNA, including without limitation, single and double stranded RNA, and RNA which is a mixture of single and double stranded regions. A polynucleotide of the invention, e.g. a polynucleotide which encodes a polypeptide or polypeptides of the invention includes allelic variants thereof and/or their complements including a polynucleotide that hybridises to such nucleotide sequences under conditions of moderate or high stringency.

The present invention further extends to antibody mimetics, such as domain antibodies, nanobodies, unibodies, versabodies, and duocalins which are based on the chimeric and felinised anti-feline NGF antibodies of the present invention. A wide variety of antibody mimetic technologies are known to the person skilled in the art. For example, so called, domain antibodies (Domantis, UK) are small functional binding units of antibodies which correspond to the variable regions of either the light or heavy chains of human antibodies. Directions for the production of such domain antibodies can be found in U.S. Pat. No. 6,291,158, U.S. Pat. No. 6,582,915 and U.S. Pat. No. 6,593,081. Nanobodies are antibody-derived therapeutic proteins which contain unique structural and functional properties of naturally occurring heavy chain antibodies found in camelids. Unibodies are a further antibody fragment technology, based upon the removal of the hinge region of IgG4 antibodies. The deletion of the hinge region results in a molecule which is approximately half the size of a traditional IgG4 antibody and which has a univalent binding region. Unibodies preserve the property of IgG4 antibodies of being inert and therefore not inducing immune responses.

Further binding molecules include affibody molecules (U.S. Pat. No. 5,831,012), DARPins (designed ankyrin repeat proteins) (International PCT Patent Application Publication WO 02/20565) and anticalins (U.S. Pat. No. 7,250,297 and WO 99/16873). Verabodies are a further antibody mimetic technology. Versabodies (Amunix, US Patent Application Publication No. 2007/0191272) are small proteins, referred to as microproteins, of 3-5 kDa with greater than 15% cysteine residues, which form a high disulphide bond density scaffold which replaces the hydrophobic core which protein typically exhibit Avimers are another type of antibody mimetic. Avimers originate from the recombination of families of human serum proteins. They are single protein chains composed of modular binding domains, each of which is designed to bind to a particular target site. The avimers can bind simultaneously to sites on a single protein target and/or sites on multiple protein targets. Known as multi-point attachment or avidity, this binding mechanism mimics the way cells and molecules interact in the body, supports the generation of antagonists and agonists, and results in drugs with multiple functions and potent activity. Avimers libraries can be produced according to WO 2004/044011 incorporated herein by reference. Avimers libraries are also available commercially from Avidia Inc, Mountain View, Calif., USA.

Antibody Production

The antibodies and binding members of the invention may be produced wholly or partly by chemical synthesis. For example, the antibodies and binding members of the invention can be prepared by techniques which are well known to the person skilled in the art, such as standard liquid peptide synthesis, or by solid-phase peptide synthesis methods. Alternatively, the antibodies and binding members may be prepared in solution using liquid phase peptide synthesis techniques, or further by a combination of solid-phase, liquid phase and solution chemistry.

The present invention further extends to the production of the antibodies or binding members of the invention by expression of a nucleic acid which encodes at least one amino acid which comprises an antibody of the invention in a suitable expression system, such that a desired peptide or polypeptide can be encoded. For example, a nucleic acid encoding the amino acid light chain and a second nucleic acid encoding an amino acid heavy chain can be expressed to provide an antibody of the present invention.

Accordingly, in certain further aspects of the invention, there is provided nucleic acids encoding amino acid sequences which form the antibodies or binding members of the present invention.

Typically, nucleic acids encoding the amino acid sequences which form antibodies or binding members of the present invention can be provided in an isolated or purified form, or provided in a form which is substantially free of material which can be naturally associated with it, with the exception of one or more regulatory sequences. Nucleic acid which expresses an antibody or binding member of the invention may be wholly or partially synthetic and may include, but is not limited to DNA, cDNA and RNA.

Nucleic acid sequences encoding the antibodies or binding members of the invention can be readily prepared by the skilled person using techniques which are well known to those skilled in the art, such as those described in Sambrook et al. "Molecular Cloning", A laboratory manual, cold Spring Harbor Laboratory Press, Volumes 1-3, 2001 (ISBN-0879695773), and Ausubel et al. Short Protocols in Molecular Biology. John Wiley and Sons, $4^{th}$ Edition, 1999 (ISBN-0471250929). Said techniques include (i) the use of the polymerase chain reaction (PCR) to amplify samples of nucleic acid, (ii) chemical synthesis, or (iii) preparation of cDNA sequences. DNA encoding antibodies or binding members of the invention may be generated and used in any suitable way known to those skilled in the art, including taking encoding DNA, identifying suitable restriction enzyme recognition sites either side of the portion to be expressed, and cutting out said portion from the DNA. The excised portion may then be operably linked to a suitable promoter and expressed in a suitable expression system, such as a commercially available expression system. Alternatively, the relevant portions of DNA can be amplified by using suitable PCR primers. Modifications to the DNA sequences can be made by using site directed mutagenesis.

Nucleic acid sequences encoding the antibodies or binding members of the invention may be provided as constructs in the form of a plasmid, vector, transcription or expression cassette which comprises at least one nucleic acid as described above. The construct may be comprised within a recombinant host cell which comprises one or more constructs as above. Expression may conveniently be achieved by culturing, under appropriate conditions, recombinant host cells containing suitable nucleic acid sequences. Following expression, the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells and NS0 mouse myeloma cells. A common, preferred bacterial host is *E. coli*. The expression of antibodies and antibody fragments in prokaryotic cells such as *E. coli* is well established in the art. Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor. Techniques for the preparation of recombinant antibody molecules are described in the above references and also in, for example, European Patent Number 0,368,684.

In certain embodiments of the invention, recombinant nucleic acids comprising an insert coding for a heavy chain variable domain and/or for a light chain variable domain of antibodies or binding members are employed. By definition, such nucleic acids comprise encode single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

The antibodies of the invention may be produced by recombinant means, not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e. cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, Ipp, or heat-stable enterotoxin II leaders.

The term "isolated", when used in reference to the felinised antibodies of the invention, or to binding members derived therefrom, or polypeptides which encode the same, refers to the state in which said antibodies, binding members or nucleic acids (polynucleotides) are provided in an isolated and/or purified form, that is they have been separated, isolated or purified from their natural environment, and are provided in a substantially pure or homogeneous form, or, in the case of nucleic acid, free or substantially free of nucleic acid or genes of origin other than the sequence encoding a polypeptide with the required function. Accordingly, such isolated antibodies, binding members and isolated nucleic acids will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo.

Antibodies, binding members and nucleic acids may be formulated with diluents or adjuvants and still, for practical purposes, be considered as being provided in an isolated form. For example the antibodies and binding members can be mixed with gelatin or other carriers if used to coat microtitre plates for use in immunoassays, or will be mixed with pharmaceutically acceptable carriers or diluents when used in diagnosis or therapy. The antibodies or binding members may be glycosylated, either naturally or by systems of heterologous eukaryotic cells (e.g. CHO or NS0 cells, or they may be (for example if produced by expression in a prokaryotic cell) unglycosylated.

Heterogeneous preparations comprising anti-feline NGF felinised antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

Pharmaceutical Compositions

Typically the pharmaceutical compositions of the invention are formulated in a liquid formulation, a lyophilized formulation, a lyophilized formulation that is reconstituted as a liquid, or as an aerosol formulation. In certain embodiments, the antibody in the formulation is at a concentration of: about 0.5 mg/ml to about 250 mg/ml, about 0.5 mg/ml to about 45 mg/ml, about 0.5 mg/ml to about 100 mg/ml, about 100 mg/ml to about 200 mg/ml, or about 50 mg/ml to about 250 mg/ml.

In certain embodiments, the formulation further comprises a buffer. Typically the pH of the formulation is from about pH 5.5 to about pH 6.5. In certain embodiments, the buffer may comprise from about 4 mM to about 60 mM histidine buffer, about 5 mM to about 25 mM succinate buffer, or about 5 mM to 25 mM acetate buffer. In certain embodiments, the buffer comprises sodium chloride at a concentration of from about 10 mM to 300 mM, typically at around 125 mM concentration and sodium citrate at a concentration of from about 5 mM to 50 mM, typically 25 mM. In certain embodiments the formulation can further comprise a surfactant at a concentration of just above 0% to about 0.2%. In certain embodiments the surfactant is selected from the group consisting of, but not limited to: polysorbate-20, polysorbate-40, polysorbate-60, polysorbate-65, polysorbate-80, polysorbate-85, and combinations thereof. In a preferred embodiment, the surfactant is polysorbate-20 and may further comprise sodium chloride at a concentration of about 125 mM and sodium citrate at a concentration of about 25 mM.

Administration

The antibodies or binding members of the present invention may be administered alone but will preferably be administered as a pharmaceutical composition which will generally comprise a suitable pharmaceutically acceptable excipient, diluent or carrier selected depending on the intended route of administration. Examples of suitable pharmaceutical carriers include; water, glycerol, ethanol and the like.

The monoclonal antibody or binding member of the present invention may be administered to a feline patient in need of treatment via any suitable route. Typically, the composition can be administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal. Routes of administration may further include topical and enteral, for example, mucosal (including pulmonary), oral, nasal, rectal.

In embodiments where the composition is delivered as an injectable composition, for example in intravenous, intradermal or subcutaneous application, the active ingredient can be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The antibodies and compositions of the invention are typically administered to a subject in a "therapeutically effective amount", this being an amount sufficient to show benefit to the subject to whom the composition is administered. The actual dose administered, and rate and time-course of administration, will depend on, and can be determined with due reference to, the nature and severity of the condition which is being treated, as well as factors such as the age, sex and weight of the subject being treated, as well as the route of administration. Further due consideration should be given to the properties of the composition, for example, its binding activity and in-vivo plasma life, the concentration of the antibody or binding member in the formulation, as well as the route, site and rate of delivery.

Dosage regimens can include a single administration of the antibody or composition of the invention, or multiple administrative doses of the antibody or composition. The antibody or antibody containing compositions can further be administered sequentially or separately with other therapeutics and medicaments which are used for the treatment of the condition for which the antibody or binding member of the present invention is being administered to treat.

Examples of dosage regimens which can be administered to a subject can be selected from the group comprising, but not limited to; 1 µg/kg/day through to 20 mg/kg/day, 1 µg/kg/day through to 10 mg/kg/day, 10 µg/kg/day through to 1 mg/kg/day. In certain embodiments, the dosage will be such that a plasma concentration of from 1 µg/ml to 100 µg/ml of the antibody is obtained. However, the actual dose of the composition administered, and rate and time-course of administration, will depend on the nature and severity of the condition being treated. Prescription of treatment, e.g. decisions on dosage etc, is ultimately within the responsibility and at the discretion of veterinary practitioners and other veterinary doctors, and typically takes account of the disorder to be treated, the condition of the individual patient, the site of delivery, the method of administration and other factors known to practitioners.

Definitions

Unless otherwise defined, all technical and scientific terms used herein have the meaning commonly understood by a person who is skilled in the art in the field of the present invention.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

As herein defined, the term "pain" means an unpleasant sensory and emotional experience associated with actual or potential tissue damage, or described in terms of such damage.

In relation to operative or post-operative pain, the US Animal Welfare Act (Animal Welfare Act 2002. AWA regulations, CFR, Title 9 (Animals and Animal Products), Chapter 1 (Animal and Plant Health Inspection Service, Department of Agriculture). Subchapter A (Animal Welfare), Parts 1-4) defines a painful procedure as any procedure that would reasonably be expected to cause more than slight or momentary pain or distress in a human being to which that procedure was applied, that is, pain in excess of that caused by injections or other minor procedures. Therefore, if a feline undergoes a painful surgical procedure, the animal should receive postoperative analgesics.

In further instance, a feline may be experiencing significant or chronic pain as a result of an associated medical condition such as arthritis, for example rheumatoid arthritis, inflammation, osteoarthritis or a cancerous or malignant condition.

The term "nociception" refers to the perception of noxious stimuli. As herein defined 'neuropathic pain' (also known as 'neuralgia') is a pain that comes from problems with signals from the nerves. It may arise as a consequence of a lesion or disease affecting the somatosensory system. There are causes of neuropathic pain and it may be associated with abnormal sensations called dysesthesia, which occur spontaneously. Alternatively, it may be associated with allodynia which results when the pain comes on, or gets worse, with a touch or stimulus that would not normally cause pain. For example, a slight touch on the face may trigger pain if you have trigeminal neuralgia, or the pressure of the bedclothes may trigger pain if you have diabetic neuropathy. Neuropathic pain may also result from allodynia, where the pain comes on, or gets worse, with a touch or stimulus that would not normally cause pain. For example, a slight touch to the face may trigger pain if a subject has trigeminal neuralgia. Neuropathic pain relating to hyperalgesia means that severe pain results from a stimulus or touch that would normally cause only slight discomfort, while paresthesia means that uncomfortable or painful feelings occur even when there is nothing in contact with the area causing the pain, for example pins and needles. Other forms of neuropathic pain involve pruritis or itch, which can be associated with allergic or inflammatory responses in the skin and inflammatory pain resulting from tissue damage and repair processes.

As defined herein, the term "NGF neutralising antibody" or similar describes an antibody that is capable of neutralising the biological activation and signalling of NGF. The neutralising antibody, which may also be referred to as an antagonistic antibody, or a blocking antibody, specifically and preferably selectively, binds to NGF and inhibits one or more biological activities of NGF. For example, the neutralising antibody may inhibit the binding of a NGF to its target ligand, such as the cell membrane bound TrkA or p75 receptors.

The term "complementarity determining region (CDR)", as used herein, refers to amino acid sequences which together define the binding affinity and specificity of the natural Fv region of a native immunoglobulin binding site as delineated by Kabat et al. (Kabat, E. A., Wu, T. T., Perry, H., Gottesman, K. and Foeller, C. (1991) Sequences of Proteins of Immunological Interest, Fifth Edition. NIH Publication No. 91-3242). The term "framework region (FR)", as used herein, refers to amino acid sequences interposed between CDRs. These portions of the antibody serve to hold the CDRs in appropriate orientation (allows for CDRs to bind antigen).

The term "constant region (CR)" as used herein, refers to the portion of the antibody molecule which confers effector functions. In the present invention, constant regions typically mean feline constant regions, that is that the constant regions of the subject felinised antibodies are derived from feline immunoglobulins. The heavy chain constant region can be selected from any feline heavy chain constant domain isotype.

The term "chimeric antibody" as used herein refers to an antibody containing sequences derived from two different antibodies, which typically are of different species. Typically chimeric antibodies comprise variable domains derived from a donor specifies which bind specifically to a target epitope and constant domains derived from antibodies obtained from the target species to whom the antibody is to be administered. The chimeric antibodies of the present invention comprise heavy and light chain variable domains derived from a rat antibody and light and heavy chain constant domains derived from feline antibodies.

The term "immunogenicity" as used herein refers to a measure of the ability of a targeting protein or therapeutic moiety to elicit an immune response (humoral or cellular) when administered to a recipient. The present invention is concerned with the immunogenicity of the subject felinised antibodies. Preferably the antibodies of the present invention have no immunogenicity, that is that no neutralising antibodies will be raised against them when administered to a feline, and further, no effector functions are mediated by the Fc regions of the antibody.

The term "identity" or "sequence identity" as used herein, means that at any particular amino acid residue position in an aligned sequence, the amino acid residue is identical between the aligned sequences. The term "similarity" or "sequence similarity" as used herein, indicates that, at any particular position in the aligned sequences, the amino acid residue is of a similar type between the sequences. For example, leucine may be substituted for an isoleucine or valine residue. This may be referred to as conservative substitution. Preferably when the amino acid sequences of the invention are modified by way of conservative substitution of any of the amino acid residues contained therein, these changes have no effect on the binding specificity or functional activity of the resulting antibody when compared to the unmodified antibody.

Sequence identity with respect to a (native) polypeptide of the invention and its functional derivative relates to the percentage of amino acid residues in the candidate sequence which are identical with the residues of the corresponding native polypeptide, after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology. Methods and computer programs for performing an alignment of two or more amino acid sequences and determining their sequence identity or homology are well known to the person skilled in the art. For example, the percentage of identity or similarity of 2 amino acid sequences can be readily calculated using algorithms e.g. BLAST (Altschul et al. 1990), FASTA (Pearson & Lipman 1988), or the Smith-Waterman algorithm (Smith & Waterman 1981).

As used herein, reference to an amino acid residue having the "highest homology" to a second amino acid residue refers to the amino acid residue which has the most characteristics or properties in common with the second amino acid residue. In determining whether an amino acid residue has the highest homology to a second amino acid residue, an assessment may typically be made of factors such as, but not limited to, charge, polarity, hydrophobicity, side arm mass and side arm dimension.

The term "corresponding position" as used herein to refer to an amino acid residue that is present in a second sequence at a position corresponding to a specified amino acid residue in a first sequence is intended to refer to the position in the second sequence which is the same position as the position in the first sequence when the two sequences are aligned to allow for maximum sequence identity between the two sequences. Amino acid residues at corresponding positions have the same Kabat numbering.

The term "consists essentially of" or "consisting essentially of" as used herein means that a polypeptide may have additional features or elements beyond those described provided that such additional features or elements do not materially affect the ability of the antibody or antibody fragment to have binding specificity to feline NGF. That is, the antibody or antibody fragments comprising the polypeptides may have additional features or elements that do not interfere with the ability of the antibody or antibody fragments to bind to feline NGF and antagonise feline NGF functional activity. Such modifications may be introduced into the amino acid sequence in order to reduce the immunogenicity of the antibody. For example, a polypeptide consisting essentially of a specified sequence may contain one, two, three, four, five or more additional, deleted or substituted amino acids, at either end or at both ends of the sequence provided that these amino acids do not interfere with, inhibit, block or interrupt the role of the antibody or fragment in binding to feline NGF and sequestering its biological function. Similarly, a polypeptide molecule which contributes to the feline NGF antagonistic antibodies of the invention may be chemically modified with one or more functional groups provided that such functional groups do not interfere with the ability of the antibody or antibody fragment to bind to feline NGF and antagonise its function.

As used herein, the term "effective amount" or "therapeutically effective amount" means the amount of an agent, binding compound, small molecule or fusion protein of the invention which is required to suppress feline NGF binding to the p75 and/or TrkA receptors.

The terms "polypeptide", "peptide", or "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide.

As herein defined an "antibody" encompasses antigen-binding proteins which specifically bind to a target antigen of interest, in this case feline nerve growth factor, having one or more polypeptides that can be recombinantly prepared or which are genetically encodable by immunoglobulin genes, or fragments of immunoglobulin genes. The term "antibody" encompasses monoclonal and chimeric antibodies, in particular equinised antibodies, and further encompasses polyclonal antibodies or antibodies of any class or subtype. An "antibody" further extends to hybrid antibodies, bispecific antibodies, heteroantibodies and to functional fragments thereof which retain antigen binding.

The phrase "specifically binds to" refers to the binding of an antibody to a specific protein or target which is present amongst a heterogeneous population of proteins. Hence, when present in specific immunoassay conditions, the antibodies bind to a particular protein, in this case feline NGF, and do not bind in a significant amount to other proteins present in the sample.

As defined herein, a "feline" may also be referred to as a cat. Felines can be categorised as belonging to the subspecies with the binomial name *Felis catus*, which includes *Felis catus* domestica and *Felis silvestris catus*. Felines include any domesticated cat and include domestic breeds and housecat varieties, these also being referred to as pets or companion animals.

The present invention will now be described with reference to the following examples which are provided for the purpose of illustration and are not intended to be construed as being limiting on the present invention.

EXAMPLES

Example 1

Production of Chimeric Antibody and Characterisation of the Same

Light chain (SEQ ID NO:1 (feN-chi-LC1) and heavy chain (SEQ ID NO:2 (feN-chi-HC2) sequences were co-expressed from pcDNA3.1 vectors in CHO cells and the supernatant tested (undiluted or at 1:10) for binding to feline and murine NGF by ELISA using a secondary anti-feline IgG polyclonal antibody-HRP conjugate. Mock pcDNA3.1 vector only transfected CHO cell supernatant was used as a control (Mock).

Figure 2:
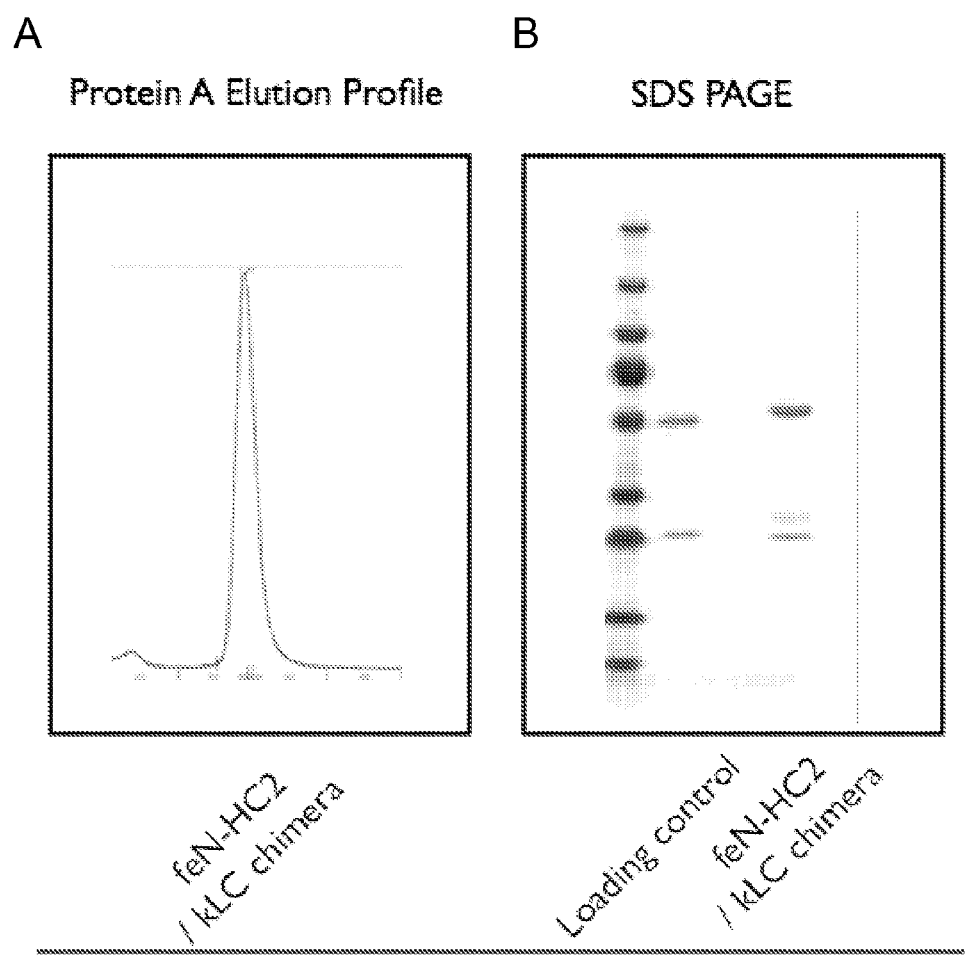
FIG. 2A shows that the feline-rat chimeric antibody can be purified using protein A.
FIG. 2B shows a gel with banding indicating both heavy and light chains of the chimeric antibody.

The results are shown in FIG. 1 (1A—binding to feline NGF, 1B—binding to murine NGF). The results show that a clear signal was detected for binding of the chimeric anti-NGF monoclonal antibody (Mab) to both feline and mouse NGFs The supernatant was purified using a Protein A affinity column and the eluted peak identified by UV absorption and analysed by SDS-PAGE. The results are shown in FIG. 2. FIG. 2A shows that the chimeric antibody can be purified on Protein A. FIG. 2B shows the chimeric feline MAb was identified by the presence of both heavy and light chains in the stained gel.

Example 2

Production of Felinised Antibodies

Whole antibody sequences were produced by combining felinised variable domain sequences with C-terminal feline constant heavy or constant light chain sequences.

The combined amino acid sequences were converted to expressible form in mammalian cells by the optimal selection of codons and full chemical gene synthesis and cloning into a mammalian cell expression vector pcDNA3.1+.

The resultant cDNAs were transfected into CHO cells and the supernatants analysed as detailed in the following examples.

Example 3

Determination of Binding of Felinised Antibodies to NGF

Combinations of felinised heavy (SEQ ID NO:6) and light chain (SEQ ID NO:5) cDNAs were transfected into CHO cells, the supernatants harvested and reacted in ELISA format with either feline or murine NGF. Following incubation and wash steps, the bound felinised antibody was detected by reactivity with a goat-anti feline IgG specific polyclonal antibody linked to horseradish peroxidase (HRP) and developed using TMB. The optical density of the resulting product was measured at 450 nm and compared with that from mock empty vector transfected supernatant (denoted as "Mock" in FIG. 1).

Figure 3:
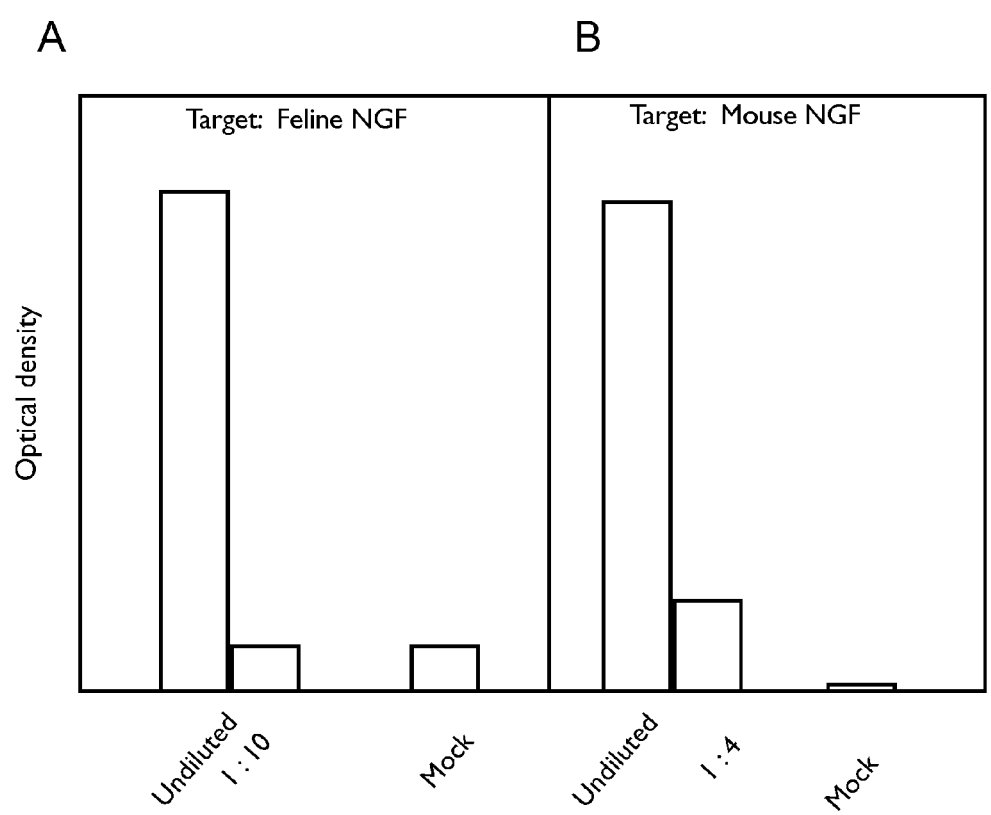
FIG. 3A is a graph showing the binding of felinised antibody to feline NGF.
FIG. 3B shows a graph indicating binding of felinised antibody to murine NGF.

The results are shown in FIG. 3. FIG. 3A shows that the felinised antibody binds to feline NGF. FIG. 3B shows that the felinised antibody binds to murine NGF with the same affinity as binding to feline NGF.

Example 4

Analysis of Purified Felinised Antibodies Using SDS-PAGE

Transfected CHO cell supernatants of felinised anti-NGF MAb from Example 3 was purified using a Protein A affinity column and the eluted peak identified by UV absorption and analysed by SDS-PAGE. (LHS) Purification profile of MAb from CHO cells co-transfected feN-HC2 and feN-kLC1 expression constructs by Protein A affinity chromatography. (RHS) Coomassie blue stained SDS-PAGE of peak fraction. Some minor degradation of the light chain was observed.

The results are shown in FIG. 4. FIG. 4A shows that the felinised antibody can be purified by Protein A. FIG. 4B shows a gel with bands representing the heavy and light chains of the felinised antibody (feN-chi-HC2 (IgG2 heavy chain) and feN-chi-kLC (light chain)).

Example 5

Inhibition of NGF Induced Proliferation of TF-1 Cells by Felinised Antibodies

Serial dilutions of CHO cell transfectant supernatants from Example 4 ('antagonis') were incubated with TF-1 cells in the presence of 0.3 ng/mL NGF. The resultant proliferation was measured by thymidine incorporation.

Figure 5:
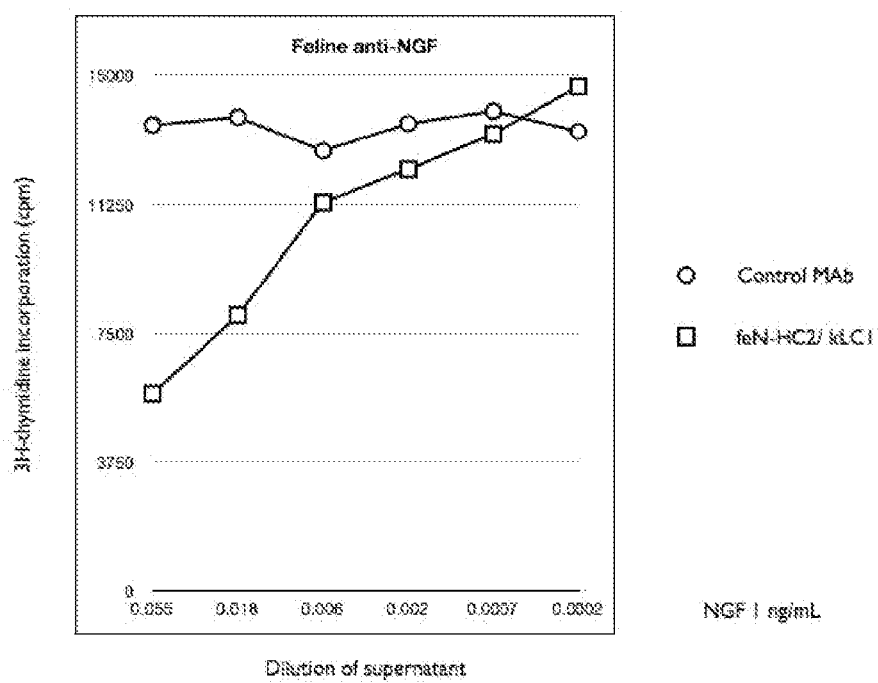
FIG. 5 is graph showing the inhibition of NGF induced proliferation of TF-1 cells by anti-feline NGF felinised antibody.

The results, shown in FIG. 5, demonstrate clear inhibition of NGF induced proliferation by the supernatant of CHO cells transfected with the felinised anti-NGF MAb.

Example 6

Complement Deposition Induced by Antigen-Captured Felinised Antibodies

CHO cell transfectant supernatants from Example 4 were incubated with plates coated with 0.1 ng/mL NGF to capture the antibodies. The plates were washed and then incubated with human serum and bound complement C1q was measured by binding of anti-human C1q polyclonal antibody HRP and developed as above.

Complement Binding Method:

Plates were coated with 100 μl/well of 5 μg/ml mouse NGF and blocked with 5% BSA/PBS. Coated wells were incubated for 1 hour at room temperature with cell culture supernatants, containing recombinant felinised anti-NGF IgG, diluted in PBS/1% BSA (100 μl/well). The plates were washed and incubated for 1 hour at room temperature with 100 μl/well of human serum diluted 1/100 in veronal buffered saline containing 0.5 mM MgCl$_2$, 2 mM CaCl$_2$, 0.05% Tween-20, 0.1% gelatin and 0.5% BSA. After washing, plates were incubated with 100 μl of a 1/800 dilution of sheep anti-C1q-HRP (Serotec) in PBS/1% BSA. After washing, plates were developed by the addition of 100 μl TMB substrate (Thermo Scientific). Development was stopped by the addition of 100 μl of 2NH$_2$SO$_4$ and absorbance read at 450 nm.

Figure 6:
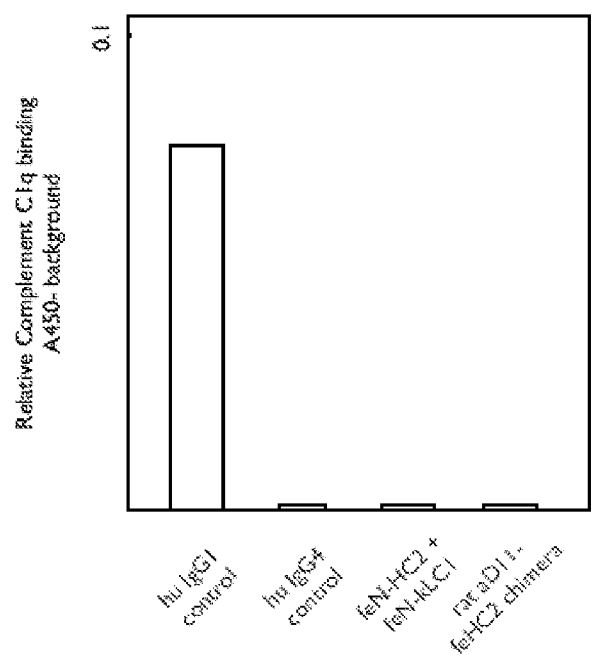
FIG. 6 shows a graph showing complement deposition induced by antigen-captured felinised antibodies.

The results are shown in FIG. 6. The results surprisingly show that felinised antibodies having the feN-chi-HC2 (IgG2) heavy chain are inactive at complement fixation. Accordingly, it is demonstrated herein, quite surprisingly, that where an antibody of the invention has a feline derived heavy chain of the HC2 subtype, the binding of the antibody to feline NGF does not result in complement activation or other downstream effector functions, such as ADCC. Hence, said antibodies, in antagonising the biological functional activity of feline NGF by preventing binding of feline NGF to the membrane bound TrkA or p75 receptors, inhibit the associated downstream intracellular signalling cascade. Furthermore, as NGF expression frequently occurs in the proximity of nerves and the like, the ability of the NGF antagonising or neutralising antibodies of the invention, which have the feline derived HC2 (IgG2) heavy chain to sequester feline NGF biological activity without recruiting a wider immune response is highly desirable, yet unexpected.

Example 7

Additional Variant Forms of Anti-Feline NGF Monoclonal Antibodies

Tables 1 through 8 illustrate that fully feline versions of anti-NGF antibodies can be generated by PETisation by comparison to a limited set of feline immunoglobulin sequences (especially feline light chains, in which case a single light chain was used for comparison). By direct sequencing and database mining, additional feline immunoglobulin kappa light and heavy chain cDNAs were derived and used for comparison to the αD11 antibody sequences. Tables 9-16 show that the addition of these comparator sequences increases the number of homologous matches between rat αD11 and feline IgG and so reduces the number of changes necessary to convert αD11 variable framework sequences to felinised variants. Tables 9-16 include the sequence variants from Tables 1-8 as "set 1" sequences and additional sequences from de novo cDNA sequencing and database mining as "set 2" sequences. The preferred felinised anti-NGF framework sequences from Tables 1-8 are annotated as "feN" and the preferred felinised anti-NGF framework sequences by comparison with "set 2" feline sequences are annotated as "feN2". Alternative feline anti-NGF immunoglobulin heavy (feN2-VH) and kappa light chain (feN2-Vk) protein sequences are shown in FIGS. 13, 14, 15 and 16 (SEQ ID NO:22-25).

TABLE 9

Light chain variable domain FR1 residues

| Vkappa FR1 Residue number | Kabat number | Feline Vk FR1 Set 1 (SEQ ID NO: 35) | Feline Vk FR1 Set 2 (SEQ ID NO: 45) | Rat aD11 (SEQ ID NO: 46) | feN-kLC (SEQ ID NO: 8) | feN2-kLC (SEQ ID NO: 26) |
|---|---|---|---|---|---|---|
| 1 | 1 | D | D, E, N | D | D | D |
| 2 | 2 | I | V, I, P, T | I | I | I |
| 3 | 3 | V | V, E, M | Q | V | E |
| 4 | 4 | M | M, L, I | M | M | M |
| 5 | 5 | T | T | T | T | T |
| 6 | 6 | Q | Q | Q | Q | Q |
| 7 | 7 | T | T, S | S | T | S |
| 8 | 8 | P | P | P | P | P |
| 9 | 9 | L | L | A | L | L |
| 10 | 10 | S | S, F | S | S | S |
| 11 | 11 | L | L | L | L | L |
| 12 | 12 | S | S, P, A | S | S | S |
| 13 | 13 | V | V | A | V | V |
| 14 | 14 | T | T, I, A | S | T | T |
| 15 | 15 | P | P | L | P | P |
| 16 | 16 | G | G | G | G | G |
| 17 | 17 | E | E, D | E | E | E |
| 18 | 18 | P | P, S, A | T | P | S |
| 19 | 19 | A | A, V | V | A | V |
| 20 | 20 | S | S | T | S | S |
| 21 | 21 | A | I, F | I | I | I |
| 22 | 22 | S | S, F | E | S | S |
| 23 | 23 | C | C | C | C | C |

TABLE 10

Light chain variable domain FR2 residues

| VKFR2 Residue number | Kabat number | Feline Vk FR2 Set 1 (SEQ ID NO: 9) | Feline Vk FR2 Set 2 (SEQ ID NO: 47) | Rat aD11 (SEQ ID NO: 48) | feN-kLC (SEQ ID NO: 9) | feN2-kLC (SEQ ID NO: 27) |
|---|---|---|---|---|---|---|
| 1 | 36 | W | W | W | W | W |
| 2 | 37 | Y | Y, F | Y | Y | Y |
| 3 | 38 | L | L, F, R | Q | L | L |
| 4 | 39 | Q | Q | Q | Q | Q |
| 5 | 40 | K | K, R | K | K | K |
| 6 | 41 | P | P | P | P | P |
| 7 | 42 | G | G | G | G | G |
| 8 | 43 | Q | Q, R | K | Q | R |
| 9 | 44 | S | S | S | S | S |
| 10 | 45 | P | P | P | P | P |
| 11 | 46 | R | R | Q | R | R |
| 12 | 47 | R | R, L | L | R | L |
| 13 | 48 | L | L | L | L | L |
| 14 | 49 | I | I, M | I | I | I |
| 15 | 50 | Y | Y, H, A | Y | Y | Y |

TABLE 11

Light chain variable domain FR3 residues

| VKFR3 Residue number | Kabat number | Feline Vk FR3 Set 1 (SEQ ID NO: 36) | Feline Vk FR3 Set 2 (SEQ ID NO: 49) | Rat aD11 (SEQ ID NO: 50) | feN-kLC (SEQ ID NO: 36) | feN2-kLC (SEQ ID NO: 28) |
|---|---|---|---|---|---|---|
| 1 | 66 | G | G, R | G | G | G |
| 2 | 67 | V | V | V | V | V |
| 3 | 68 | P | P | P | P | P |
| 4 | 69 | D | D | S | D | D |
| 5 | 70 | R | R | R | R | R |
| 6 | 71 | F | F, I | F | F | F |
| 7 | 72 | S | S, T | S | S | S |
| 8 | 73 | G | G | G | G | G |
| 9 | 74 | S | S | S | S | S |
| 10 | 75 | G | G | G | G | G |
| 11 | 76 | S | S | S | S | S |
| 12 | 77 | G | G | G | G | G |
| 13 | 78 | T | T, A, S | T | T | T |
| 14 | 79 | D | D | Q | D | D |
| 15 | 80 | F | F | Y | F | F |
| 16 | 81 | T | T, I, A | S | T | T |
| 17 | 82 | L | L | L | L | L |
| 18 | 82A | R | R, T, K | K | R | K |
| 19 | 82B | I | I | I | I | I |
| 20 | 82C | S | S, A, G, T | N | S | S |
| 21 | 83 | R | R, G | S | R | R |
| 22 | 84 | V | V, M | L | V | V |
| 23 | 85 | E | E, Q | Q | E | Q |
| 24 | 86 | A | A, V, P, T | S | A | T |
| 25 | 87 | D | DE | E | D | E |
| 26 | 88 | D | D | D | D | D |
| 27 | 89 | V | V | V | V | V |
| 28 | 90 | G | G | A | G | G |
| 29 | 91 | V | V, I, H, L | S | V | V |
| 30 | 92 | Y | Y | Y | Y | Y |
| 31 | 93 | F | Y, F | F | F | F |
| 32 | 94 | C | C | C | C | C |

TABLE 12

Light chain variable domain FR4 residues

| VKFR4 Residue number | Kabat number | Feline Vk FR4 Set 1 (SEQ ID NO: 11) | Feline Vk FR4 Set 2 (SEQ ID NO: 51) | Rat aD11 (SEQ ID NO: 52) | feN-kLC (SEQ ID NO: 11) | feN2-kLC (SEQ ID NO: 29) |
|---|---|---|---|---|---|---|
| 1 | 103 | F | F, S | F | F | F |
| 2 | 104 | G | G | G | G | G |
| 3 | 105 | P | Q, P | G | P | Q |
| 4 | 106 | G | G | G | G | G |
| 5 | 107 | T | T | T | T | T |
| 6 | 108 | K | K, H, Q, E, S, T | K | K | K |
| 7 | 109 | L | L | L | L | L |
| 8 | 110 | E | E, D | E | E | E |
| 9 | 111 | I | I, V, M, L | L | I | L |
| 10 | 112 | K | K, R, D, T | K | K | K |

TABLE 13

Heavy chain variable domain FR1 residues

| VHFR1 Residue number | Kabat number | Feline VH FR1 Set 1 (SEQ ID NO: 53) | Feline VH FR1 Set 2 (SEQ ID NO: 54) | Rat aD11 VH (SEQ ID NO: 55) | feN-VH (SEQ ID NO: 56) | feN2-VH (SEQ ID NO: 30) |
|---|---|---|---|---|---|---|
| 1 | 1 | Q, D, H | Q, D, E | Q | Q | Q |
| 2 | 2 | V, E | V, E | V | V | V |
| 3 | 3 | Q, L | L, Q, R | Q | Q | Q |
| 4 | 4 | L | L, V | L | L | L |
| 5 | 5 | V | V, M | K | V | V |
| 6 | 6 | E, Q | Q, E, D | E | E | E |
| 7 | 7 | S | S | S | S | S |
| 8 | 8 | G | G | G | G | G |
| 9 | 9 | G, A, R | A, G | P | G | A |
| 10 | 10 | D, E | E, D, N | G | D | E |
| 11 | 11 | L, V | L, V, R | L | L | L |
| 12 | 12 | V, R, S | V, R, K | V | V | V |
| 13 | 13 | Q, K | K, T, Q, E, N, R | Q | Q | Q |
| 14 | 14 | P | P, T | P | P | P |
| 15 | 15 | G, E | G, E | S | G | G |
| 16 | 16 | G, A | G, A, T, E | Q | G | E |
| 17 | 17 | S | S, A | T | S | S |
| 18 | 18 | L, V | L, V | L | L | L |
| 19 | 19 | R, K, S | R, K, E | S | R | R |
| 20 | 20 | L, I | I, L, P | L | L | L |
| 21 | 21 | T, F, S | F, T, S | T | T | T |
| 22 | 22 | C | C | C | C | C |
| 23 | 23 | A, V, M, K | K, V, A, Q | T | A | A |
| 24 | 24 | A, T | A, T, D | V | A | A |
| 25 | 25 | S | S | S | S | S |
| 26 | 26 | G | G, A | G | G | G |

TABLE 14

Heavy chain variable domain FR2 residues

| VHFR2 Residue number | Kabat number | Feline VH FR2 Set 1 (SEQ ID NO: 57) | Feline VH FR2 Set 2 (SEQ ID NO: 58) | Rat aD11 VH (SEQ ID NO: 59) | feN-VH (SEQ ID NO: 13) | feN2-VH (SEQ ID NO: 13) |
|---|---|---|---|---|---|---|
| 1 | 36 | W | W | W | W | W |
| 2 | 37 | V, L, W, F, A | V, L, F, I | V | V | V |
| 3 | 38 | R, C | R, C, H | R | R | R |
| 4 | 39 | Q | Q | Q | Q | Q |
| 5 | 40 | A, P, T | A, S, V, T | A | A | A |
| 6 | 41 | P | P | T | P | P |
| 7 | 42 | G, E, A | G, A, E, S | G | G | G |
| 8 | 43 | K, Q, T | Q, K, E | R | K | K |
| 9 | 44 | G | G | G | G | G |
| 10 | 45 | L, F | L, F, P | L | L | L |
| 11 | 46 | E, Q | E, Q | E | E | E |
| 12 | 47 | W, E, T | W, C, L | W | W | W |
| 13 | 48 | M, V, L | V, M, I | M | M | M |
| 14 | 49 | G, A, T, S | G, A, S | G | G | G |

TABLE 15

Heavy chain variable domain FR3 residues

| VHFR3 Residue number | Kabat number | Feline VH FR3 Set 1 (SEQ ID NO: 60) | Feline VH FR3 Set 2 (SEQ ID NO: 61) | Rat aD11 VH (SEQ ID NO: 62) | feN-VH (SEQ ID NO: 14) | feN2-VH (SEQ ID NO: 32) |
|---|---|---|---|---|---|---|
| 1 | 66 | R | R, Q, K | R | R | R |
| 2 | 67 | L, F | L, F | L | F | L |
| 3 | 68 | T, A | T, I | T | T | T |
| 4 | 69 | I, L, V | L, I, M, V | I | I | I |
| 5 | 70 | S, T | S, T | T | S | T |
| 6 | 71 | R, A, I | R, A, T, K, G, V | R | R | R |
| 7 | 72 | D | D | D | D | D |
| 8 | 73 | T, N, S | T, N, D, A, S | T | N | T |
| 9 | 74 | A, S, G, T | S, A, D, T | S | A | S |
| 10 | 75 | K, T, R, G, Q | T, K, E, Q, N, R | K | K | K |
| 11 | 76 | N, D | N, D, K | S | N | N |
| 12 | 77 | T, A | T, I, A | Q | T | T |
| 13 | 78 | L, A | A, L, V, G | V | L | V |
| 14 | 79 | Y, D, S | Y, F, A, S, V, W | F | Y | F |
| 15 | 80 | L, M | L, M | L | L | L |
| 16 | 81 | Q, E, L, R | E, Q, D, H, V | K | Q | Q |
| 17 | 82 | M, L, T | L, M | M | M | M |
| 18 | 82A | N, S, D, T | N, S, T, D, G, R, H | H | N | H |
| 19 | 82B | S, I, N, R, T | S, N | S | S | S |
| 20 | 82C | L | L | L | L | L |
| 21 | 83 | K, R, G, T | R, K, Q, T | Q | K | Q |
| 22 | 84 | S, T, P, A | S, T, I, A, V | S | T | S |
| 23 | 85 | E, T, A, D | E, A, T, D, G, S | E | E | E |
| 24 | 86 | D | D | D | D | D |
| 25 | 87 | T, A | T | T | T | T |
| 26 | 88 | A | A, G, S | A | A | A |
| 27 | 89 | T, V, M | T, V, M, I, A | T | T | T |
| 28 | 90 | Y | Y, H | Y | Y | Y |
| 29 | 91 | Y, C, F | Y, H, F | Y | Y | Y |
| 30 | 92 | C, R | C | C | C | C |
| 31 | 93 | A, G, I, T, S, V | A, T, V, G, L, I, M | A | A | A |
| 32 | 94 | R, K, S, T, I, V, P, N, G | R | R | R | R |

TABLE 16

Heavy chain variable domain FR4 residues

| VHFR4 Residue number | Kabat number | Feline VH FR4 Set 1 (SEQ ID NO: 63) | Feline VH FR4 Set 2 (SEQ ID NO: 64) | Rat aD11 VH (SEQ ID NO: 33) | feN-VH (SEQ ID NO: 15) | feN2-VH (SEQ ID NO: 33) |
|---|---|---|---|---|---|---|
| 1 | 103 | W, R | W, R, C, L | W | W | W |
| 2 | 104 | G, R | G, A | G | G | G |
| 3 | 105 | Q, P, V, H, R | Q, H, R, P, V | Q | Q | Q |
| 4 | 106 | G | G, D | G | G | G |
| 5 | 107 | T, A, V, I, S | A, T, V | T | T | T |
| 6 | 108 | L, I, Q | L, I, Q, M, S, T | T | L | T |
| 7 | 109 | V | V, I | V | V | V |
| 8 | 110 | T | T, A, I, R | T | T | T |
| 9 | 111 | V | V, G | V | V | V |
| 10 | 112 | S, T | S, P | S | S | S |
| 11 | 113 | S, Q, P | S, Q, A | A | S | A |

Example 8

Anti-Feline NGF Monoclonal Antibodies—Safety and Pyrexia

Anti-feline NGF monoclonal antibodies of the invention are expressed in CHO cells and purified by a combination of Protein A chromatography and/or size exclusion chromatography and are buffer exchanged into phosphate buffered saline. The antibodies are injected intravenously into cats at 0.01-10 mg/kg body weight and assessed for signs of toxicity by visual inspection by a veterinarian, change in body weight, body temperature and plasma biochemistry. No changes are expected to be observed in these or any plasma biochemistry analytes.

Example 9

Plasma Pharmacokinetics of Anti-Feline NGF Monoclonal Antibodies in vivo—Serum Half-Life and Immunogenicity The anti-feline NGF monoclonal antibodies of the invention are expressed in CHO cells and purified by a combination of Protein A chromatography and/or size exclusion chromatography and buffer exchanged into phosphate buffered saline. The antibodies are injected intravenously into cats in the range 0.01-10 mg/kg body weight and plasma samples are taken at various times over the next 2 weeks. Diluted plasma samples are assessed for anti-feline NGF antibody concentration by ELISA using NGF as the target and anti-feline polyclonal antibody-horseradish peroxidase secondary reagent. The plasma concentrations measured are consistent with two-phase kinetics, with a tissue distribution (alpha) phase and an elimination phase (beta) phase of several days.

The absence of a sharp decline in plasma concentration of anti-feline NGF antibody concentration between 100 and 300 hours is expected. This would demonstrate that there is neither pre-existing neutralising antibodies to recombinant anti-NGF monoclonal antibodies in cat blood nor are any such neutralising antibodies generated following infusion.

Example 10

Anti-Feline NGF Monoclonal Antibodies Reduce Inflammatory Pain in vivo

Feline Model of Inflammation:

Cats are injected (=day −1) with a pro-inflammatory agent (e.g. kaolin) into the footpad of one leg in order to generate a self-resolving inflammation beginning approximately 24 hours later and which causes the cats to become temporarily lame. In this model, once the initial inflammation response to kaolin recedes, the cats become steadily less lame over the period of approximately 1-2 weeks and then recover.

Groups of cats are injected intravenously with either anti-feline NGF monoclonal antibodies of this patent at 0.01-10 mg/kg body weight or phosphate buffered saline as vehicle control (=day 0). The cats are assessed for lameness over 4-14 days by a visual scoring method (e.g. score 0, no lameness (full weight bearing); score 1, slight lameness (not full weight bearing but walking well); score 2, moderate lameness (slightly weight bearing and not walking well), score 3, severe lameness (not weight bearing)). Observers are blinded to which cats receive which injection.

Lameness scores are expected to be reduced in the cats receiving anti-feline NGF monoclonal antibodies by day 2-4 post-injection compared with vehicle control, indicating that the anti-feline NGF monoclonal antibodies will have an effect in reducing the pain in the cats over that seen with vehicle alone.

Example 11

Comparison Example Showing the Effect of Anti-Canine NGF Monoclonal Antibodies in Reducing Inflammatory Pain in vivo Antibody Therapy:

The method of preparing antibodies of the present invention was applied to produce a caninised antibody suitable for use in canines. A caninised αD11 VL domain was combined with a canine kappa light chain constant domain and a caninised αD11 VH domain was combined with a canine heavy chain isotype. Anti-canine NGF monoclonal antibodies derived from expression vectors expressing the heavy and light chains were expressed in CHO cells and purified by a combination of ion exchange chromatography, hydrophobic interaction chromatography and size exclusion chromatography and buffer exchanged into phosphate buffered saline.

Canine Model of Inflammation:

All experiments were carried out with prior approval of the Institutional Ethics Committee (CRL, Ireland). Beagle dogs were injected (=day −1) with kaolin into the footpad of one hind leg in order to generate a self-resolving inflammation beginning approximately 24 hours later and which causes the dogs to become temporarily lame. In this model, once the initial inflammation response to kaolin recedes, the dogs become steadily less lame over the period of approximately 1-2 weeks and then make a full recovery.

Groups of 3 dogs were injected intravenously with either anti-canine NGF monoclonal antibodies at 200 μg/kg body weight or phosphate buffered saline as vehicle control (=day 0). The dogs were assessed for lameness over 7 days by a visual scoring method (score 0, no lameness (full weight bearing); score 1, slight lameness (not full weight bearing but walking well); score 2, moderate lameness (slightly weight bearing and not walking well), score 3, severe lameness (not weight bearing)). Observers were blinded to which dogs received which injection.

Figure 17:
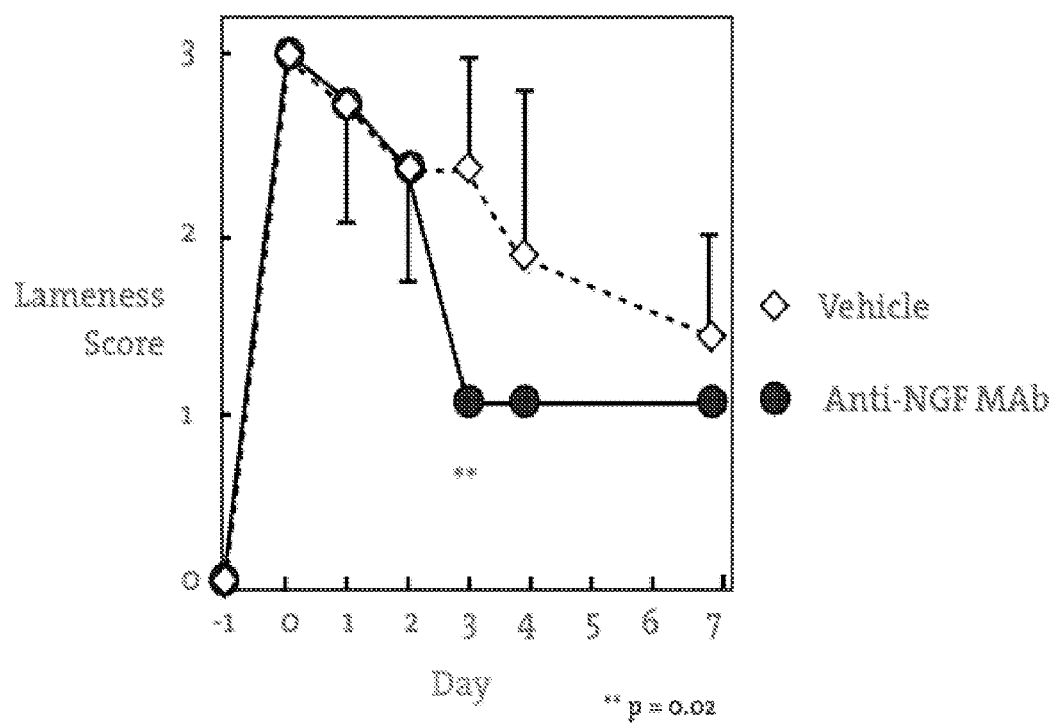
FIG. 17 shows that anti-canine NGF monoclonal antibodies prepared by a method corresponding to the method of the present invention reduce inflammatory pain in dogs.

The results are shown in FIG. 17. Lameness scores were reduced in the dogs receiving anti-NGF monoclonal antibodies by day 3 post-injection compared with vehicle control, indicating that the anti-NGF monoclonal antibodies had an effect in reducing the pain in the dogs over that seen with vehicle alone. The delayed activity is consistent with the plasma pharmacokinetics of anti-canine NGF monoclonal antibodies which demonstrated a slow tissue distribution (alpha) phase of approximately 30 hours and the relatively poor vascularisation of the footpad area. The results shown in FIG. 17 show that the anti-canine NGF antibodies prepared by a method corresponding to the method of the present invention reduce inflammatory pain in dogs with a consequent reduction in lameness.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

---

The invention claimed is:

1. An antibody or an antigen binding fragment thereof which is capable of specifically binding to feline neuronal growth factor (NGF) and inhibiting the ability of feline NGF to bind to the p75 feline NGF receptor and/or the TrkA feline NGF receptor, wherein the antibody or antigen binding fragment comprises:
   a light chain variable region comprising the amino acid sequence selected from the group consisting of SEQ ID NO:3 and SEQ ID NO:23 and amino acid sequences having a sequence identity of at least 85% thereto, wherein the light chain variable region comprises a CDR1 sequence comprising RASEDIYNALA (residues 24-34 of SEQ ID NOs 3 and 23), a CDR2 sequence comprising NTDTLHT (residues 50-56 of SEQ ID NOs 3 and 23), and a CDR3 sequence comprising HYFHYPRT (residues 90-97 of SEQ ID NOs 3 and 23), and
   a heavy chain variable region comprising the amino acid sequence selected from the group consisting of SEQ ID NO:4 and SEQ ID NO:22 and sequences having an amino acid identity of at least 85% thereto, wherein the heavy chain variable region comprises a CDR1 sequence comprising NNNVN (residues 31-35 of SEQ ID NOs 4 and 22), a CDR2 sequence comprising GVWAGGATDYNSALK (residues 50-64 of SEQ ID NOs 4 and 22), and a CDR3 sequence comprising DGGYSSSTLYAMDA (residues 98-111 of SEQ ID NOs 4 and 22), and
   wherein the antibody or antigen binding fragment thereof does not contain any amino acid in any position within the framework regions which would be foreign at the corresponding position in a feline antibody.

2. The antibody or antigen binding fragment thereof as claimed in claim 1, wherein the light chain variable region comprises the amino acid sequence of SEQ ID NO:3 and the heavy chain variable region comprises the amino acid sequence of SEQ ID NO:4.

3. The antibody or antigen binding fragment thereof as claimed in claim 1, wherein the light chain comprises the amino acid sequence of SEQ ID NO:5 or an amino acid sequence which has an identity of at least 85% thereto and wherein the heavy chain comprises the amino acid sequence of SEQ ID NO:6 or an amino acid sequence which has an identity of at least 85% thereto.

4. The antibody or antigen binding fragment thereof as claimed in claim 3, wherein the light chain comprises the amino acid sequence of SEQ ID NO:5 and wherein the heavy chain comprises the amino acid sequence of SEQ ID NO:6.

5. The antibody or antigen binding fragment thereof as claimed in claim 1, wherein the light chain comprises the amino acid sequence of SEQ ID NO:25 or an amino acid sequence which has an identity of at least 85% thereto and wherein the heavy chain comprises the amino acid sequence of SEQ IDNO:24 or an amino acid sequence which has an identity of at least 85% thereto.

6. The antibody or antigen binding fragment thereof as claimed in claim 1, wherein the light chain variable region comprises the amino acid sequence of SEQ ID NO:23 or an amino acid sequence which has an identity of at least 85% thereto and the heavy chain variable region comprises the amino acid sequence of SEQ ID NO:22 or an amino acid sequence which has an identity of at least 85% thereto.

7. The antibody or antigen binding fragment thereof as claimed in claim 1, wherein the light chain variable region comprises the amino acid sequence of SEQ ID NO:23 and the heavy chain variable region comprises the amino acid sequence of SEQ ID NO:22.

8. The antibody or antigen binding fragment thereof as claimed in claim 1, comprising a heavy chain constant domain selected or modified by way of amino acid substitution or deletion such that said constant domain does not mediate effector functions.

9. The antibody or antigen binding fragment thereof as claimed in claim 8, wherein the antibody has a feline heavy chain constant domain as shown in Genbank Accession No. BAA32229.1 (SEQ ID NO:34).

10. The antibody or antigen binding fragment thereof as claimed in claim 9, wherein the heavy chain comprises the amino acid sequence selected from the group consisting of SEQ ID NO:6, SEQ ID NO:7, SEQ ID NO:17 and SEQ ID NO:18, or an amino acid sequence which has a sequence identity of at least 85% thereto.

11. A pharmaceutical composition comprising the antibody or antigen binding fragment thereof as claimed in claim 1, together with at least one pharmaceutically acceptable carrier, excipient or diluent.

12. A kit for the treatment of pain in felines, or for the treatment of a condition associated with pain, or for the treatment, amelioration or inhibition of pain associated with osteoarthritis, inflammation, pruritis, immune mediated polyarthritis or rheumatoid arthritis comprising an anti-feline NGF antibody or fragment according to claim 1 and instructions for use of the same.

13. An antibody or antigen binding fragment thereof which is capable of specifically binding to feline neuronal growth factor (NGF) and inhibiting the ability of feline NGF to bind to the p75 feline NGF receptor and/or the TrkA feline NGF receptor, the antibody or antigen binding fragment thereof comprising
   a light chain variable region comprising:
   a CDR1 sequence comprising RASEDIYNALA (residues 24-34 of SEQ ID NO:23), a CDR2 sequence comprising NTDTLHT (residues 50-56 of SEQ ID NO:23), and a CDR3 sequence comprising HYFHYPRT (residues 90-97 of SEQ ID NO:23);
   an FR1 framework region comprising the amino acid sequence of SEQ ID NO:26 or an amino acid sequence which has a sequence identity of at least 85% thereto;
   an FR2 framework region comprising the amino acid sequence of SEQ ID NO:27 or an amino acid sequence which has a sequence identity of at least 85% thereto;
   an FR3 framework region comprising the amino acid sequence of SEQ ID NO:28 or an amino acid sequence which has a sequence identity of at least 85% thereto; and
   an FR4 framework region comprising the amino acid sequence of SEQ ID NO:29 or an amino acid sequence which has a sequence identity of at least 85% thereto;
   and a heavy chain variable region comprising:
   a CDR1 sequence comprising NNNVN (residues 31-35 of SEQ ID NO:22), a CDR2 sequence comprising GVWAGGATDYNSALK (residues 50-64 of SEQ ID NO:22), and a CDR3 sequence comprising DGGYSSSTLYAMDA (residues 98-111 of SEQ ID NO:22);
   an FR1 framework region comprising the amino acid sequence of SEQ ID NO:30 or an amino acid sequence which has a sequence identity of at least 85% thereto;
   an FR2 framework region comprising the amino acid sequence of SEQ ID NO:31 or an amino acid sequence which has a sequence identity of at least 85% thereto;

an FR3 framework region comprising the amino acid sequence of SEQ ID NO:32 or an amino acid sequence which has a sequence identity of at least 85% thereto; and an FR4 framework region comprising the amino acid sequence of SEQ ID NO:33 or an amino acid sequence which has a sequence identity of at least 85% thereto.

14. The antibody or antigen binding fragment thereof as claimed in claim 13 comprising a light chain variable region comprising:
an FR1 framework region comprising the amino acid sequence of SEQ ID NO:26;
an FR2 framework region comprising the amino acid sequence of SEQ ID NO:27;
an FR3 framework region comprising the amino acid sequence of SEQ ID NO:28; and
an FR4 framework region comprising the amino acid sequence of SEQ ID NO:29;
and a heavy chain variable region comprising:
an FR1 framework region comprising the amino acid sequence of SEQ ID NO:30;
an FR2 framework region comprising the amino acid sequence of SEQ ID NO:31;
an FR3 framework region comprising the amino acid sequence of SEQ ID NO:32; and
an FR4 framework region comprising the amino acid sequence of SEQ ID NO:33.

15. The antibody or antigen binding fragment thereof as claimed in claim 13, comprising a heavy chain constant domain selected or modified by way of amino acid substitution or deletion such that said constant domain does not mediate effector functions.

16. The antibody or antigen binding fragment thereof as claimed in claim 15, wherein the antibody has a feline heavy chain constant domain as shown in Genbank Accession No. BAA32229.1 (SEQ ID NO:34).

17. The antibody or antigen binding fragment thereof as claimed in claim 16, wherein the heavy chain comprises the amino acid sequence selected from the group consisting of SEQ ID NO:6, SEQ ID NO:7, SEQ ID NO:17 and SEQ ID NO:18, or an amino acid sequence which has a sequence identity of at least 85% thereto.

18. A pharmaceutical composition comprising the antibody or antigen binding fragment thereof as claimed in claim 13, together with at least one pharmaceutically acceptable carrier, excipient or diluent.

19. A kit for the treatment of pain in felines, or for the treatment of a condition associated with pain, or for the treatment, amelioration or inhibition of pain associated with osteoarthritis, inflammation, pruritis, immune mediated polyarthritis or rheumatoid arthritis comprising an anti-feline NGF antibody or fragment according to claim 13 and instructions for use of the same.

* * * * *